US006906076B2

(12) United States Patent
Bukrinsky et al.

(10) Patent No.: US 6,906,076 B2
(45) Date of Patent: Jun. 14, 2005

(54) COMPOUNDS AND METHODS OF USE TO TREAT INFECTIOUS DISEASES

(75) Inventors: Michael I. Bukrinsky, Potomac, MD (US); Anthony Cerami, Sleepy Hollow, NY (US); Peter Ulrich, Portland, OR (US); Bradley Berger, Medicine Hat (CA)

(73) Assignee: Cytokine Pharmasciences, Inc., King of Prussia, PA (US)

( * ) Notice: Subject to any disclaimer, the term of this patent is extended or adjusted under 35 U.S.C. 154(b) by 0 days.

(21) Appl. No.: 10/660,748

(22) Filed: Sep. 12, 2003

(65) Prior Publication Data

US 2004/0053815 A1 Mar. 18, 2004

Related U.S. Application Data

(63) Continuation of application No. 09/887,020, filed on Jun. 25, 2001, now Pat. No. 6,649,797, which is a continuation of application No. 08/732,653, filed on Oct. 15, 1996, now Pat. No. 6,297,253.

(51) Int. Cl.[7] ..................... A61K 31/505; C07D 239/28

(52) U.S. Cl. ....................... 514/256; 514/269; 514/634; 514/637; 514/689; 436/86; 436/111; 436/128; 544/264; 544/276; 544/277; 544/319; 544/321; 544/323; 544/326; 544/332; 544/335; 564/237; 564/244; 564/305; 568/42; 568/43; 568/308; 568/329; 568/331; 568/335; 568/337

(58) Field of Search ........................... 436/86, 111, 128; 564/305; 568/42, 43, 308, 329, 331, 335, 337; 544/321, 335; 514/256, 269, 689

(56) References Cited

U.S. PATENT DOCUMENTS

| | | | | |
|---|---|---|---|---|
| 5,574,040 A | | 11/1996 | Bukrinsky et al. | 514/275 |
| 5,620,983 A | | 4/1997 | Bukrinsky et al. | 514/261 |
| 5,703,086 A | | 12/1997 | Bukrinsky et al. | 514/275 |
| 5,733,932 A | | 3/1998 | Bukrinsky et al. | 514/634 |
| 5,808,068 A | | 9/1998 | Pan et al. | 544/315 |
| 5,840,305 A | | 11/1998 | Bukrinsky et al. | 424/152.1 |
| 5,840,839 A | | 11/1998 | Wang et al. | 544/329 |
| 5,840,893 A | | 11/1998 | Bukrinsky et al. | 544/329 |
| 5,849,793 A | | 12/1998 | Pan et al. | 514/456 |
| 6,297,253 B1 | | 10/2001 | Bukrinsky et al. | 514/275 |
| 6,649,797 B2 | * | 11/2003 | Bukrinsky et al. | 564/305 |

OTHER PUBLICATIONS

Kalderon, et al., "A Short Amino Acid Sequence Able to Specify Nuclear Location", Cell, 39, 499–509 (1984—Part 2).

Dingwall, et al., "The Nucleoplasmin Nuclear Location Sequence is Larger and More Complex than that of SV–40 Large T Antigen", J. Cell Biol., 107, 841–849 (1988).

Yeh, et al., "The Arginine–Rich Domain of Hepatitis B Virus Precore and Core Proteins Contains a Signal for Nuclear Transport", J. Virol., 64, 12, 6141–6147 (1990).

Zacksenhaus, et al., "A Bipartite Nuclear Localization Signal in the Retinoblastoma Gene Product and Its Importance for Biological Activity", Mol. Cell. Biol., 13, 8, 4588–4599 (1993).

Bukrinsky, et al., "A Nuclear Localization Signal Within HIV–1 Matrix Protein that Governs Infection of Non–Dividing Cells", Nature, 365, 666–669 (1993).

Goldfarb, et al., "Synthetic Peptides as Nuclear Localization Signals", Nature, 322, 641–644 (1986).

Lanford, "Induction of Nuclear Transport with a Synthetic Peptide Homologous to the SV40 T Antigen Transport Signal", Cell, 46, 575–582 (1986).

Adam, et al., "Identification of Specific Binding Proteins for a Nuclear Location Sequence", Nature, 337, 276–279 (1989).

Robbins, et al., "Two Interdependent Basic Domains in Nucleoplasmin Nuclear Targeting Sequence: Identification of a Class of Bipartite Nuclear Target Sequence", Cell, 64, 615–623 (1991).

Görlich, et al., "Two Different Subunits of Importin Cooperate to Recognize Nuclear Localization Signals and Bind Them to the Nuclear Envelope", Curr. Biol., 5, 4, 383–392 (1995).

Radu, et al., "Identification of a Protein Complex that is Required for Nuclear Protein Import and Mediates Docking of Import Substrate to Distinct Nucleoporines", Proc. Natl. Acad. Sci., 92, 1769–1773 (1995).

Adam, et al., "Cytoslic Proteins that Specifically Bins Nuclear Location Signals are Receptors for Nuclear Import", Cell, 66, 837–847 (1992).

Rexach, et al., "Protein Import Into Nuclei: Association and Dissociation Reactions Involving Transport Substrate, Transport Factors, and Nucleoporins", Cell, 83, 683–692 (1995).

Moore, et al., "Purification of a Ran–Interacting Protein that is Required for Protein Import into the Nucleus", Proc. Natl. Acad. Sci., 91, 10212–10216 (1994).

Nerhbass, et al., "Role of the Nuclear Transport Factor p10 in Nuclear Import", Science, 272, 120–122 (1996).

Dabauvalle, et al., "Inhibition of Nuclear Accumulation of Karyophilic Proteins in Living Cells by Microinjection of the Lectin Wheat Germ Agglutinin", Exp. Cell Res., 174, 291–296 (1988).

(Continued)

*Primary Examiner*—Richard L. Raymond

(74) *Attorney, Agent, or Firm*—Steven B. Kelber; DLA Piper Rudnick; Gray Cary US LLP

(57) ABSTRACT

The present invention concerns alkyl aryl carbonyl compounds that possess anti-infective activity. The compounds of the invention can be used to target specific nuclear localization signal, thereby blocking importation of specific proteins or molecular complex into the nucleus of a cell. The invention encompasses methods of use of such compounds for treatment or prevention of infectious diseases, such as parasitic and viral diseases, including, for example, malaria and acquired immunodeficiency syndrome. The use of the compounds to detect certain specific protein structures which are present in nuclear localization sequences is also taught.

31 Claims, 26 Drawing Sheets

OTHER PUBLICATIONS

Figure 1A:
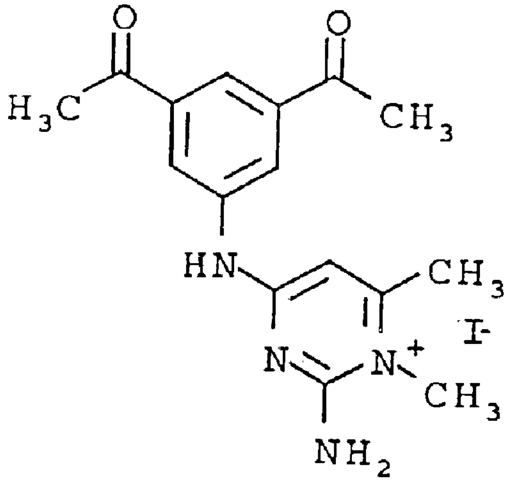

Sterne–Marr, et al., "O–Linked Glycoproteins of the Nuclear Pore Complex Interact with a Cytosolic Factor Required for Nuclear Protein Import", J. Cell Biol, 116, 2, 271–280 (1992).

Melchior, et al., "Inhibition of Nuclear Protein Import by Nonhydrolyzable Analogues of GTP and Identification of the Small GTPase Ran/TC4 as an Essential Transport Factor", J. Cell Biol., 123, 6, Part 2, 1649–1656 (1993).

Weinberg, et al., "Productive Human Immunodeficiency Virus Type 1 (HIV–1) Infection of Nonproliferating Human Monocytes", J. Exp. Med., 174, 1477–1482 (1991).

Humphries, et al., "Requirement for Cell Division for Initiation of Transcription of Rous Sarcoma Virus RNA", J. Virol., 14, 3, 531–546 (1974).

Stevenson, et al., "HIV–1 Replication is Controlled at the Level of T Cell Activation and Proviral Integration", EMBO J., 9, 5, 1551–1560 (1990).

Bukrinsky, et al., "Quiescent T Lymphocytes as an Inducible Virus Reservoir in HIV–1 Infection", Science, 254, 423, Science (1991).

Zack, et al., "Incompletely Reverse–Transcribed Human Immunodeficiency Virus Type 1 Genomes in Quiescent Cells Can Function as Intermediates in the Retroviral Life Cycle", J. Virol., 66, 3, 1717–1725 (1992).

Schnittman, et al., "The Reservoir for HIV–1 in Human Peripheral Blood is a T Cell That Maintains Express of CD4", Science, 245, 305–308 (1989).

Brinchmann, et al., "Few Infected $CD4^+$ T Cells but a High Proportion of Replication–Competent Provirus Copies in Asymptomatic Human Immunodeficiency Virus Type 1 Infection", J. Virol., 65, 4, 2019–2023 (1991).

Chapel, et al., "Differential Human Immunodeficiency Virus Expression in $CD4^+$ Cloned Lymphoscytes: From Viral Latency to Replication", J. Virol., 66, 6, 3966–3970 (1992).

Keonig, et al., "Detection of AIDS Virus in Marcrophages in Brain Tissue from AIDS Patients with Encephalopathy", Science, 233, 1089–1093 (1986).

Wiley, et al., "Cellular Localization of Human Immunodeficiency Virus Infection Within the Brains of Acquired Immune Deficiency Syndrome Patients", Proc. Natl. Acad. Sci., 83, 7089–7093 (1986).

Price, et al., "The Brain in AIDS: Central Nervous System HIV–1 Infection and AIDS Dementia Complex", Science, 239, 586–592 (1988).

Giulian, et al., "Secretion of Neurotoxins by Mononuclear Phagocytes Infected with HIV–1", Science, 250, 1593–1596 (1990).

Fauci, et al., "Immunopathogenic Mechanisms in Human Immunodeficiency Virus (HIV) Infection", Ann. Int. Med., 114, 8, 678–693 (1991).

Pantaleo, et al., "HIV Infection is Active and Progressive in Lymphoid Tissue During the Clinically Latent Stage of Disease", Nature, 362, 355–358 (1993).

Zack, "HIV–1 Entry Into Quiescent Primary Lymphocytes: Molecular Analysis Reveals a Labile, Latent Viral Structure", Cell, 61, 213–222 (1990).

Spina, et al., "The Importance of nef in the Induction of Human Immunodeficiency Virus Type 1 Replication from Primary Quiescent CD4 Lymphocytes", J. Exp. Med., 179, 115–113 (1994).

Miller, et al., "The Human Immunodeficiency Virus–1 nef Gene Product: A Positive Factor for Viral Infection and Replication in Primary Lymphocytes and Macrophages", J. Exp. Med., 101–113 (1994).

von Schwedler, et al., "The Nuclear Localization Signal of the Matrix Protein of Human Immunodeficiency Virus Type 1 Allows the Establishment of Infection in Macrophages and Quiescent T Lymphocytes", Proc. Natl. Acad. Sci., 91, 6992–6996 (1994).

Brown, et al., "Correct Integration of Retroviral DNA in Vitro", Cell, 49, 347–356 (1987).

Emerman, et al., "HIV–1 Infection of Non–Dividing Cells", Nature, 369, 107–108 (1994).

Heinzinger, et al., "The Vpr Protein of Human Immunodeficiency Virus Type 1 Influences Nuclear Localization of Viral Nucleic Acids in Nondividing Host Cells", Proc. Natl. Acad. Sci., 91, 7311–7315 (1994).

Gulizia, et al., "Reduced Nuclear Import of Human Immunodeficiency Virus Type 1 Preintegration Complexes in the Presence of a Prototypic Nuclear Targeting Signal", J. Virol. 68, 3, 2021–2025 (1994).

"Malaria", Tropical Diseases, Progress in Research 1989–1990, World Health Organization, pp. 29–40 (1991).

Nosten, et al., "New Antimalarials, A Risk–Benefit Analysis", Drug Safety, 12, 4, 264–273 (1995).

Rabjohn, "Selenium Dioxide Oxidation", Org. React., Chapter 4, 261–415 (1976).

March, Advanced Organic Chemistry, $4^{th}$ ed., Wiley Interscience, New York, 491–493 (1992).

Fenton, et al., "Metal Complexes of 1,1,–[1,3–Phenylene] bis–1,3–Butanedione", Inorg. Chim. Acta, 44, L105–L106 (1980).

Gordon, et al., "Applications of Combinatorial Technologies to Drug Discovery. 2. Combinatorial Organic Synthesis, Library Screening Strategies, and Future Directions", J. Med. Chem., 37, 10, 1385–1401 (1994).

Chen, et al., "'Analogous' Organic Synthesis of Small-Compound Libraries: Validation of Combinatorial Chemistry in Small–Molecule Synthesis", J. Amer. Chem. Soc., 116, 2661–2662 (1994).

Cho, et al., "An Unnatural Bioploymer", Science, 261, 1303–1305 (1993).

Bukrinsky, et al., "Active Nuclear Import of Human Immunodeficiency Virus Type 1 Preintegration Complexes", Proc. Natl. Acad. Sci., 89, 6580–6584.

Desjardins, et al., "Quantitative Assesment of Antimalarial Activity In Vitro by a Semiautmated Microdilution Technique", Antimicrob. Ag. Chemother., 16, 6, 710–718 (1979).

Ager, Jr., Handbook of Experimental Pharmacology, Antimalarial Drugs I, Peters, et al., eds., Chapter 8, vol. 68, Part 1, 225–264, Springer–Verlag, Berlin (1984).

Bukrinsky, et al., "Regulation of Nitric Oxide Synthase Activity in Human Immunodeficiency Virus Type 1 (HIV–1)–infected Monocytes: Implications for HIV–Associated Neurological Disease", J. Exp. Med., 181, 735–745 (1995).

Ulrich, et al., "Trypanocidal 1,3–Arylene Diketone Bis(guanylhydrazone)s. Structure–Activity Relationships Among Substituted and Heterocyclic Analogues", J. Med. Chem., 27, 35–40 (1983).

McKinnon, et al., "Studies on Some 2,1–Benzisoxazole Derivatives", Can. J. Chem., 49, 2019–2022 (1971).

Gartner, et al., "The Role of Mononuclear Phagocytes in HTLV–III/LAV Infection", Science, 233, 215–219 (1986).

Nuovo, et al., “Rapid In Situ Detection of PCR–Amplified HIV–1 DNA”, Diagn. Mol. Pathol., 1, 2, 98–102 (1992).
Chou, “Derivation and Properties of Michaelis–Menten Type and Hill Type Equations for Reference Ligands”, J. Theor. Biol., 59, 253–276 (1976).
Berger, et al., “Primary and Secondary Metabolism of Pentamidine by Rats” Antimicrob. Ag. Chemother., 36, 9, 1825–1831 (1992).
Westervelt, et al., “Macrophage Tropism Determinants of Human Immunodeficiency Virus Type 1 In Vivo”, J. of Virol., 66, 4, 2577–2582 (1992).
Haffar, et al., “Human Immunodeficiency Virus–Like, Nonreplicating, gan–env Particles Assemble in a Recombinant Vaccinia Expression System”, J. Virol., 64, 6, 2653–2659 (1990).
Chandraratna et al., Chemical Abstracts, vol. 119:270992, 1993.
Porter et al., Chemical Abstracts, vol. 117:90296, 1992.
Reisdorff et al., Chemical Abstracts vol. 87:147051, 1977.
Barnish et al., Chemical Abstracts, vol. 87:5796, 1977.

* cited by examiner

| | | | | | |
|---|---|---|---|---|---|
| CNI-H0294 (μM) | 0.1 | 0 | 0.1 | 0.1 | 0.1 |
| CNI-H3094 (μM) | 0 | 0.1 | 0.01 | 0.1 | 1 |

COMPOUNDS AND METHODS OF USE TO TREAT INFECTIOUS DISEASES

This application is a Continuation of application Ser. No. 09/887,020, filed on Jun. 25, 2001, now U.S. Pat. No. 6,649,797, which is a Continuation of application Ser. No. 08/732,653, filed Oct. 15, 1996, now U.S. Pat. No. 6,297, 253.

1 FIELD OF THE INVENTION

The field of the present invention concerns compounds that react with specific sequences in proteins. The present invention more particularly concerns a class of compounds that react, under physiologic conditions, with proteins having adjacent or neighboring basic amino acid sequences. The compounds of the invention can be used to label specifically such proteins for research purposes and to disrupt their function for pharmacologic purposes. The compounds of the invention can be used for targeted inactivation of nuclear localization signal in specific proteins or molecular complexes. The compounds of the invention can also be used to treat infectious diseases such as HIV infection and malaria.

2 BACKGROUND TO THE INVENTION

2.1 The Derivatization of Proteins

Those skilled in the art will appreciate that there are many compounds that can react with specific amino acid residues in proteins, e.g., with sulfhydryl, amino, carboxyl moieties. These reagents are substrate specific, in the sense that each reacts only with one or a few specific amino acids wherever they occur within a protein's sequence.

However, the reactivity of such reagents is not affected by the adjacent or neighboring amino acids that form the environment of the reactive moiety. Thus, the reactivity of such compounds is not context or neighborhood specific.

2.2 Nuclear Importation

The function of an intracellular protein is usually the result of the overall three dimensional (tertiary) structure of the protein. However, nuclear importation is determined by the simple presence of a short sequence, called a nuclear localization signal (NLS), which functions relatively independently of its position relative to the remainder of the structure of object that is imported. In eukaryotic cells all proteins are made in the cytoplasm, which is outside of the nucleus. In general, those proteins larger than 40 kD that are specifically localized in the nucleus of the cell must be actively imported into the nucleus through the nuclear membrane from the cytoplasm via an ATP-dependent mechanism that is independent of cell division. The proteins, and other objects, that are imported have a nuclear localization signal (NLS), usually located within the $NH_2$ terminal segment of the protein. Several such sequences are known:

a. PKKKRKV from large T antigen of SV40 and other papillomaviruses such as JC, see Kalderon, D., et al., 1984, Cell 39:499–509;

b. [AV]KRPAATKKAGQAKKKK [LD] from nucleoplasmin, in which only one of the two bracketed sequences is required, Dingwall, C., et al., 1988, J. Cell Biol. 107:841–49;

c. PRRRRSQS from hepatitis B HbcAg-Yeh, C. T., 1990, J. Virol.

d. KRSAEGGNPPKPLKKLR from the retinoblastoma gene product p110$^{rb1}$-Zacksenhaus E. et al., 1993, Mol. Cell. Biol. 13:4588 e. KIRLPRGGKKKYKLK from the matrix protein of HIV-1, Bukrinsky, M. I., et al., 1993, Nature 365:666.

Other viruses that contain NLS sequences include influenza virus (NP, PA, PB1, PB2 proteins which have lysine-rich NLS similar to SV40), hepatitis delta virus (HDAg, which has the sequence PKKKXKK), parvoviruses such as RA1 (NS, VP proteins which have lysine-rich NLS similar to SV40), Herpes simplex and measles virus. The recognition of an NLS sequence is largely independent of the detailed structure of the object which includes it and of its site of attachment. Goldfarb, D. S. et al., 1986, Nature 332:641–44; Lanford, R. E., 1986, Cell 46:575. Mere juxtaposition of the amino acids of the NLS is not sufficient for function, for example NLS function is generally not conferred by the peptide having the same sequence of amino acids in the opposite order as the NLS sequence. Adam, S. A. et al., 1989, Nature 337:276–79.

The primary structure, i.e., the linear sequence, of the NLS most frequently contains consecutive lysines, the $N^{\epsilon}$ moieties of which presumably closely approach one another, i.e., they are neighbors. However, certain functional NLS peptides lack consecutive lysines. Robbins, J., et al., 1991, Cell 64:615–23. Presumably the secondary and tertiary structure of these so called "bipartite" NLS peptides gives rise to neighboring $N^{\epsilon}$ moieties, which may be important for their activity.

Docking and subsequent movement of proteins across the nuclear pore complex require transport factors. Import of NLS-containing proteins across the nuclear pore complex is mediated by karyopherin αβ heterodimers (also termed NLS receptor/importin) which bind NLS-containing proteins in the cytosol and target them to the nucleus (Gorlich, D., et al., 1995, Curr. Biol. 5:383–392; Radu, A., et al., 1995, Proc. Natl. Acad. Sci. 92:1765–1773). Karyopherin a binds the NLS (Adam and Gerace, 1991, Cell 66:837–847) whereas karyopherin β enhances the affinity of α for the NLS (Rexach and Blobel, 1995, Cell 83:683–692) and mediates docking of karyopherin-NLS protein complexes to nucleoporins (a collective term for nuclear pore complex proteins) that contain FXFG peptide repeats. The GTPase Ran and its interacting protein p10 (also termed NTF2) (Moore and Blobel, 1994, Proc. Natl. Acad. Sci. 91:10212–10216) impart mobility to the translocation process by catalyzing the disruption of karyopherin αβ heterodimers that have docked to a nucleoporin (Nerhbass and Blobel, 1996, Science 272:120–122). Partial reactions of the nuclear import can be reproduced in vitro using solution binding assays and recombinant karyopherins (Rexach and Blobel, 1995, supra).

Two inhibitors of the nuclear localization process have been described. Nuclear localization has been inhibited by lectins (e.g., wheat germ agglutinin (WGA)) that bind to the O-linked glycoproteins associated with nuclear localization. Dabauvalle, M. -C., 1988, Exp. Cell Res. 174:291–96; Sterne-Marr R., et al., 1992, J. Cell Biol. 116:271. The nuclear localization process, which also depends upon the hydrolysis of GTP, is blocked by a non-hydrolyzable analog of GTP, e.g., (γ-S)GTP, Melchior, F., 1993, J. Cell Biol. 123:1649.

However, neither (γ-S)GTP nor WGA can be used as pharmaceuticals. Proteins, such as WGA, can be introduced into the interior of a cell only with considerable difficulty. The same limitation applies to thiotriphospates such as [γ-S]GTP. Further, GTPases are involved in a multitude of cell processes and intercellular signaling, thus, the use of a general inhibitor of GTPases would likely lead to unacceptable side effects.

2.3 THE SIGNIFICANCE OF NUCLEAR IMPORTATION IN HIV-1 INFECTIONS

Although HIV-1 is a retrovirus, it and other lentiviruses must be distinguished from viruses of the onco-retrovirus group, which are not associated with progressive fatal infection. For example, lentiviruses replicate in non-proliferating cells, e.g., terminally differentiated macrophages, Weinberg, J. B., 1991, J. Exp. Med. 172:1477–82, while onco-retroviruses, do not. Humphries, E. H., & Temin, H. M., 1974, J. Virol. 14:531–46. Secondly, lentiviruses are able to maintain themselves in a non-integrated, extrachromosomal form in resting T-cells. Stevenson, M., et al., 1990, EMBO J. 9:1551–60; Bukrinsky, M. I., et al., 1991, Science 254:423; Zack, J. L., et al., 1992, J. Virol. 66:1717–25. However, it is unclear whether this phenomenon is related to the presence of latently infected peripheral blood lymphocytes (PBL) in HIV-1 infected subjects, wherein the virus is present in a provirus form. Schnittman, S. M., 1989, Science 245:305; Brinchmann, J. E., et al., 1991, J. Virol. 65:2019; Chapel, A., et al., 1992 J. Virol. 66:3966.

The productive infection of a cell by a retroviruses involves the steps of penetration into the cell, synthesis of a DNA genome from the RNA genetic material in the virion and insertion of the DNA genome into a chromosome of the host, thereby forming a provirus. Both lenti- and oncoretroviruses gain access to the host cell's nucleus during mitosis when the nuclear membrane dissolves. However, the lentiviruses are also able to cross the nuclear membrane because viral proteins containing nuclear localization sequences are associated with the viral nucleoprotein complex.

The productive infection of terminally differentiated macrophages located in the central nervous system is thought to be responsible for the dementia associated with AIDS. Keonig, S., et al., 1986, Science 233:1089; Wiley, C. A. et al., 1986, Proc. Natl. Acad. Sci. 83:7089–93; Price, R. W., et al., 1988, Science 239:586–92. The infection of terminally differentiated macrophages in the lymphoid system is known to cause aberrant cytokine production. Guilian, D., et al., 1990, Science 250:1593; Fauci, A. S., et al., 1991, Ann. Int. Med. 114:678. Thus, the wasting syndrome associated with HIV-1, also known as "slim" disease, is believed to be a pathological process that is independent of the loss of CD4-T-cells. Rather the pathobiology of the wasting is closely related to the pathobiology of cachexia in chronic inflammatory and malignant diseases. Weiss, R. A., 1993, Science 260:1273. For these reasons, the inhibition on HIV-1 infection of macrophages and other non-dividing cells is understood to represent a highly desired modality in the treatment of HIV-1 infection, especially for patients wherein dementia or cachexia dominate the clinical picture.

Macrophages play an important role in the transmission of HIV as well. During early stages of the infection, macrophages and cells of the macrophage lineage (i.e. dendritic cells) may be the primary reservoir of HIV-1 in the body, supporting infection of T cells by antigen presentation activities, Pantaleo, G., et al., 1993, Nature 362:355–358, as well as via the release of free virus. Direct cell-to-cell transmission of the virus may constitute the major route by which infection spreads during the early-stages of the disease, after resolution of the initial viremia.

It is noteworthy, in this regard, that macrophage-tropic strains of HIV-1 predominate in the early stages of infection. Thus, it appears that the infection of macrophages is particularly important during the development of a chronic infective state of the host in a newly infected subject.

Secondly, macrophages are the HIV-susceptible cell type most readily passed during sexual intercourse from an HIV-infected individual into the circulation of an uninfected individual.

Finally, infection of quiescent T cells by HIV-1 has been shown to take place in vitro, Stevenson, M., et al., 1990, EMBO J. 9:1551–1560; Zack, J. A., 1990, Cell 61:213–222, and probably constitutes an important pathway for the spread of infection in vivo at various stages of the disease. Bukrinsky, M. I., et al., 1991, Science 254:423–427. Although HIV-1 does not establish productive replication in quiescent T cells, the extrachromosomal retroviral DNA can persist in the cytoplasm of such cells for a considerable period of time, and initiate replication upon activation of the host cell. Stevenson, M., et al., 1990, EMBO J. 9:1551–1560; Spina, C. A., et al., 1994, J. Exp. Med. 179:115–123; Miller, M. D., et al., 1994, J. Exp. Med. 179:101–113. A recent report suggests that the duration of viral persistence in the quiescent T cell depends on the presence of a functional NLS. von Schwedler, U., et al., 1994, Proc. Natl. Acad. Sci. 91:6992–6996. Thus, physicians recognize the desirability of preventing the infection of macrophages by HIV and understand that substantial benefits would be obtained from the use of a pharmacologic agent that prevents HIV infection in this cell type.

The mechanism whereby HIV, but not oncoretroviruses, infect non-dividing cells is now understood in broad outline. It is established that the function of the pre-integration complex of retrovirus in this regard does not depend upon the cellular mechanisms of mitosis or DNA replication, per se. Rather the integration complex must merely gain access to nucleus. Brown, P. O., et al., 1987, Cell 49:347. Onco-retroviruses gain access to the nucleus upon the dissolution of the nuclear membrane in mitosis. By contrast, lentiviruses contain two distinct proteins that mediate nuclear access through the nuclear pore complex in the absence of cellular division. For the first of these, the matrix protein (MA or p17), nuclear importation activity is clearly due to the presence of a trilysyl-containing NLS sequence. Bukrinsky, M. I., et al., 1993, Nature 365:666; von Schwedler, U., et al., 1994, Proc. Natl. Acad. Sci. 91:6992. A second protein subserving the function of nuclear entry, the vpr protein, does not contain an identifiable NLS consensus sequence. Emerman, M., et al., 1994, Nature 369:108; Heinzinger, N. K. et al., 1994, Proc. Natl. Acad. Sci. 91:7311.

The significance of the NLS sequence in the importation of HIV-1 into the nucleus of non-dividing cells has been illustrated in experiments wherein the presence in the medium of a high concentration (0.1 M) of the peptide having the sequence of the SV40 T-antigen NLS blocked the importation of HIV-1 into the nucleus of aphidicolin-arrested $CD4^+$ MT4 cells. Gulizia, J., et al., 1994, J. Virol. 68:2021–25.

2.4 INFECTIOUS DISEASES AND ITS TREATMENT

Treatment of an infectious disease with chemicals involves killing or inhibition of growth of the infectious agent, which may include free-living and parasitic organisms. Parasitic diseases are widespread in the animal world where a parasitic organism lives at the expense of a host organism, and causes damage, or kills its host. Humans, domestic pets and livestocks are hosts to a variety of parasites. Parasites do not comprise a single taxonomic group, but are found within the protozoans and metazoans, among other groups. In many ways, infectious parasitic diseases resemble infectious diseases caused by microbiologicals such as fungi, bacteria and viruses.

Malaria remains one of the major health problems in the tropics. It is estimated that 300 million people a year are infected with malaria (World Health Organization, 1990, Malaria pp. 29–40. In Tropical Diseases, Progress in Research 1989–1990, Geneva). Malaria is transmitted by Anopheles mosquitos in endemic areas, and often by blood transfusion in eradicated areas.

Malaria in humans is caused by at least four protozoan species of *Plasmodium: P. falciparum, P. vivax, P. ovale* and *P. malariae*. The asexual erythrocytic parasite, merozoite, is the stage in the life cycle that causes the pathology of malaria with a characteristic pattern of fever, chills and sweats. Anemia, acute renal failure and disturbances in consciousness are often associated with malarial infection. *P. falciparum* can produce a large number of parasites in blood rapidly, and causes the most morbidity and mortality.

The most important treatment of malaria to date is chemotherapy using a number of natural and synthetic drugs. Antifolates, such as pyrimethamine, inhibit the parasite's dihydrofolate reductase, whereas the aminoquinolines, such as chloroquine (4-aminoquinoline) have the digestive vacuoles as their major site of action. Prior to the introduction of chloroquine in the 1940's, quinine was the only effective drug for treatment of malaria. Chloroquine is commonly used to treat acute infections with all four species, but has no effect on relapses of infection by *P. vivax* or *P. ovale*.

Chloroquine (500 mg weekly) may also be used to prevent malaria by suppressing the stages that multiply in the erythrocytes and cause the symptoms.

However, the use of these drugs in certain areas and in the future will be seriously hampered by the emergence of drug resistant parasites. Chloroquine resistance is widespread and will continue to appear in new areas. Due to the possibility of resistance, the presence of parasites in blood (i.e., parasitemia) is followed closely during treatment, and alternative drugs instituted if indicated. The decision on drug regimen will depend on the origin of the infection. Combination therapy, such as quinine and Fansidar (pyrimethamine and sulfadoxine), is applied to treat chloroquine-resistant *P. falciparum*. Because of the presence of multidrug resistant *P. falciparum* in many parts of the world, prevention of malaria by chemoprophylaxis with currently available drugs is not always effective.

In the last 20 years, only several drugs, such as mefloquine, halofantrine and artemisinin derivatives, have been developed to treat *P. falciparum* (Nosten et al., 1995, Drug Saf. 12:264–73). In view of the continuing spread of multidrug resistant *P. falciparum*, it is apparent that novel effective chemotherapeutic agents are needed for use against malaria.

3 SUMMARY OF THE INVENTION

The present invention encompasses a class of alkyl aryl carbonyl compounds that forms stable binding interactions, preferably through formation of reversible covalent bonds, with one or more basic amino acid residues, wherein such basic amino acid residues are a part of a nuclear localization signal (NLS). The stable binding interaction results in the inhibition or neutralization of the nuclear localization activity of the NLS. The binding interaction is mediated by one functional component of the compound, i.e., the reactive group, whereas another functional component of the compound, i.e. the targetting group, determines the specificity of the compound for different-NLS.

This targetting function occurs by interaction of the targetting group with a docking site that is positioned proximately to the susceptible basic residues of the target NLS, such that docking of the compound places it in a favorable configuration to form a stable interaction with basic amino acid residues of the target NLS. The docking site is located either on the same NLS-bearing protein, or on another component of a larger molecular complex that includes the NLS-bearing protein.

Preferred compounds of the invention provide divalent aryl carbonyl moieties as the reactive group, particularly aryl bis(ketone), aryl bis(α-diketone) or aryl bis(β-diketone), linked to a targetting group, preferably to a nitrogen-containing heterocyclic functionality via an N-linkage. Particularly preferred compounds provided are bis acetyl, propanoyl, glyoxyloyl, pyruvoyl, 2-oxobutanoyl, acetoacetyl, 3-oxopentanoyl, 3-oxo-2,2-dimethylbutanoyl or 3-oxo-2,2-dimethylpentanoyl substituted aniline moieties N-linked to a pyrimidinium, pyrimidine or triazine moiety.

The invention further encompasses methods of using the compounds of the invention to form tandem binding interactions with proteins having neighboring basic residues. As used, herein, neighboring basic residues are two basic amino acid residues of a protein, particularly lysine and arginine residues, the side chain amino or guanidino functions of which approach each other as closely as the bis carbonyl functions of the arylene bis(carbonyl) compounds of the invention, when the protein is in its natured conformation. As used herein neighboring, adjacent and juxtaposed are equivalent terms in reference to amino or guanidino moieties, and refer to the physical locations of the amino or guanidino moieties in the structure of the native protein and not to the positions of the basic amino acid residues themselves in the linear sequence.

In one embodiment of the invention, the compounds of the invention can be used to react with neighboring nitrogenous moieties in lysine and arginine residues of nuclear localization sequence (NLS) of a protein, thereby inactivating the NLS. The invention also encompasses uses of compounds of the invention for specifically inhibiting importation of a NLS-containing protein or molecular complex comprising a NLS-containing protein, into the nucleus of a cell. The carbonyl group(s) of the compounds of the invention inactivates the NLS of a protein which is essential for nuclear translocation of the complex. The compounds of the invention are targeted to the complex by the specific interaction between the targetting group, preferrably a nitrogen-containing heterocyclic targetting group, and a docking site on a molecule in the complex that is distinct from the NLS. The invention further encompasses methods of screening for alkyl aryl bis(carbonyl) and bis(dicarbonyl) compounds that are capable of inhibiting importation of a specific NLS-containing protein or molecular complex comprising a NLS-containing protein into the nucleus of a cell. The screening assays of the present invention allow a compound of the present invention to be identified and selected without advance knowledge of the specific docking site that confers specificity on the NLS inhibitory activity of the compound.

The invention further encompasses methods of inhibiting productive infection by HIV-1 of terminally differentiated (non-dividing cells), particularly macrophages, by inhibition of the importation of the cytoplasmic HIV-1 complex into the nucleus of cell. Particularly the invention concerns the administration of the compound effective to block such importation to a cell. Thus, in one embodiment, the invention encompasses methods of using the above-described compounds to prevent productive infection of terminally differentiated macrophages and resting T-cells in HIV-1 infected subjects.

Without limitation as to theory, the compounds of the invention is believed to block HIV-1 replication by binding to reverse transcriptase and formation of tandem Schiff bases with neighboring $N^\epsilon$ moieties of lysines in the nuclear localization signal of HIV matrix antigen. As a result, the matrix antigen is unable to interact with karyopherin α of the host cell and the viral nucleoprotein complex does not pass across the nuclear membrane via interaction with the nuclear pore transport complex and/or other cellular components.

Moreover, compounds of the present invention are also useful for inhibiting viral infection or nuclear translocation of viral proteins in proliferating cell populations, to the extent that such occurs in some of the cells in the population during periods of the cell cycle in which the nuclear membrane is intact. Such infection or nuclear translocation of proteins in a proliferating population of cells is susceptible to treatment with the compounds of the present invention on the same basis as non-dividing or quiescent populations would be susceptible.

The invention further encompasses methods of using the compounds of the invention in treating or preventing infectious diseases such as those caused by parasites, particularly *Plasmodium* species that cause malaria.

4 BRIEF DESCRIPTION OF THE FIGURES

Figure 1B:
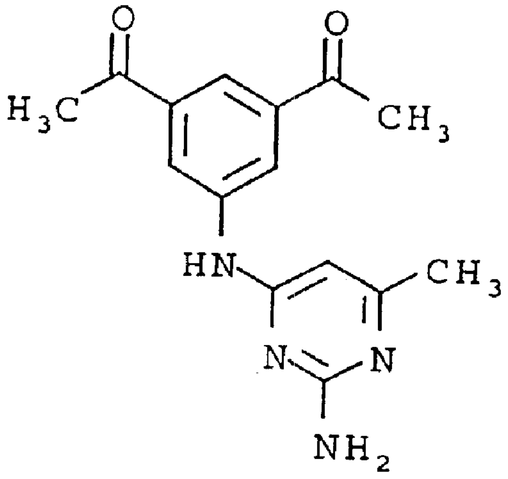
Figure 1C:
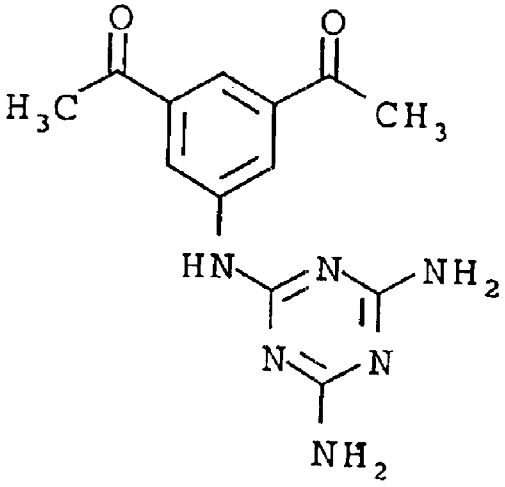

FIGS. 1A–C. The structures of exemplary Compounds No. 2, 11 and 13 are, respectively, FIGS. 1A, 1B, 1C.

Figure 2A:
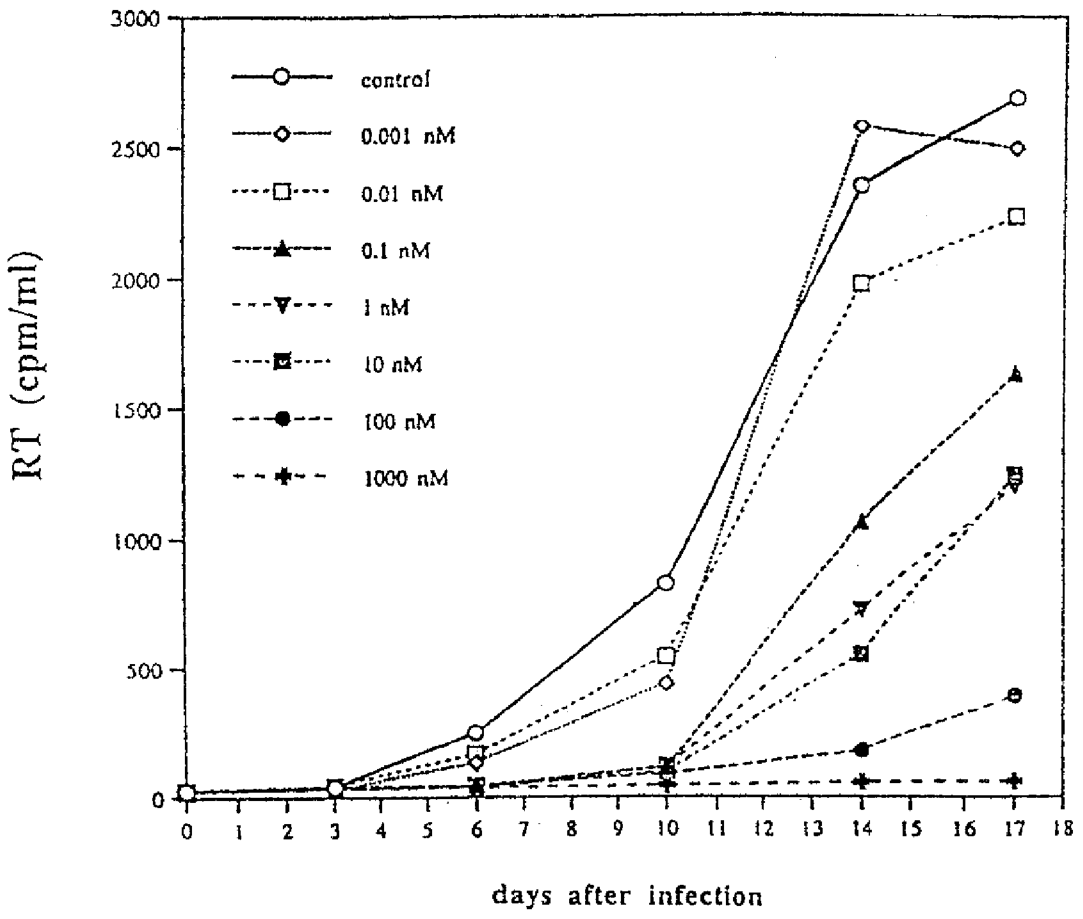
Figure 2B:
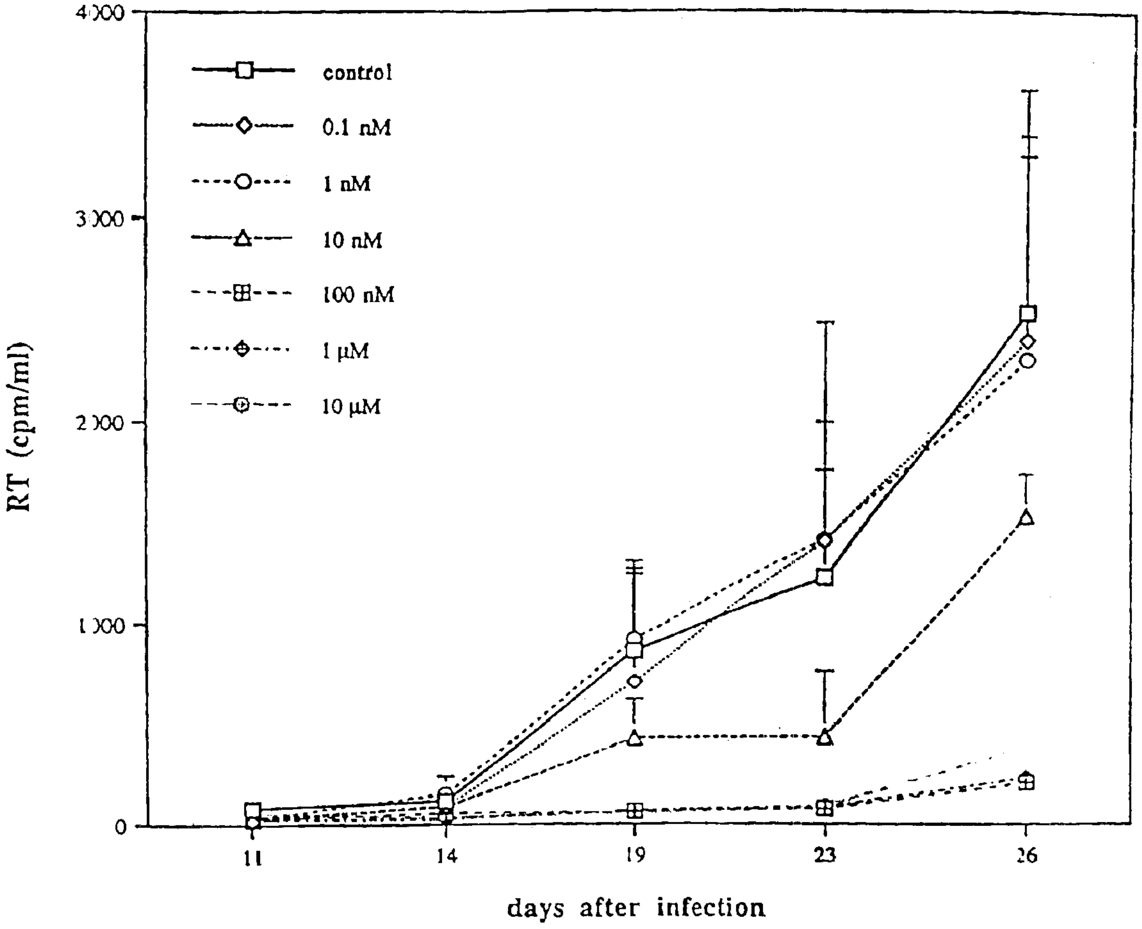
Figure 2C:
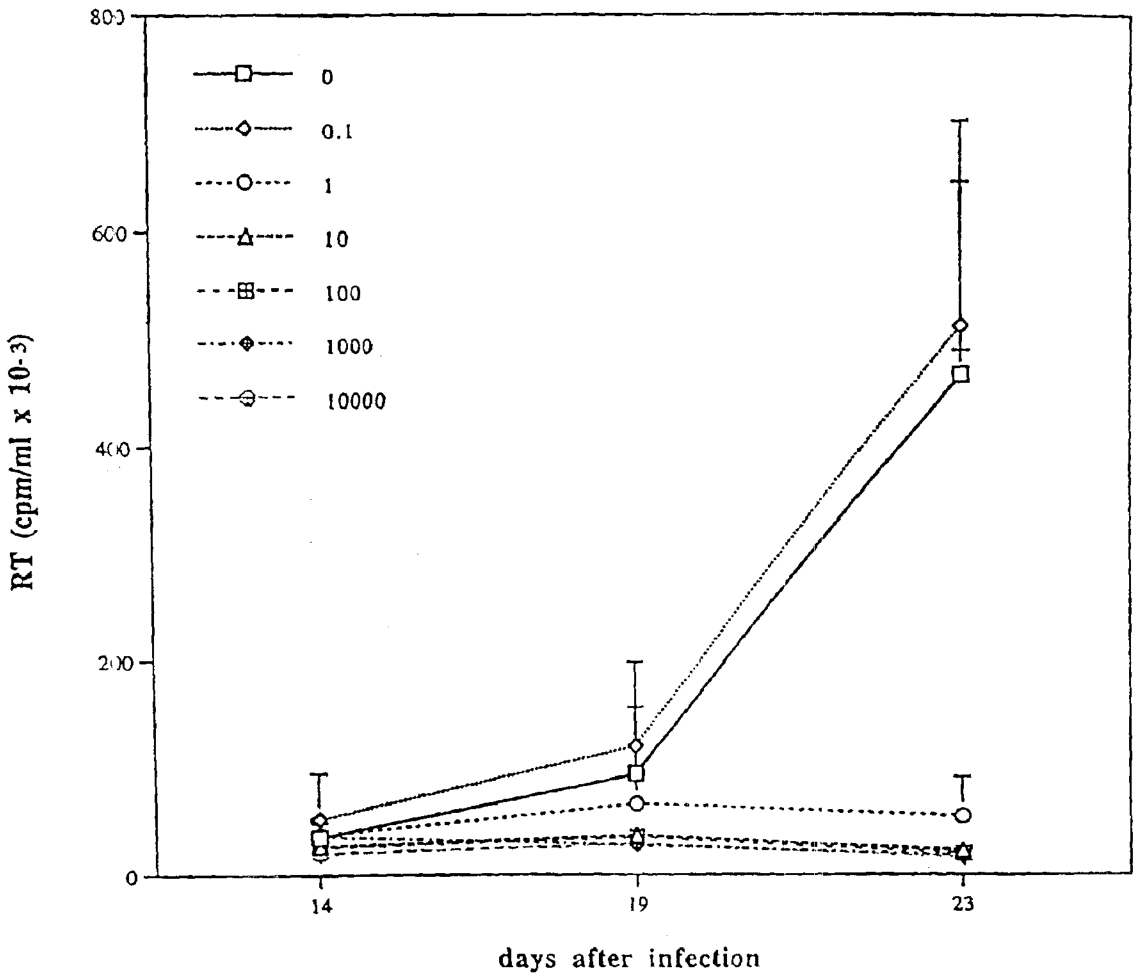

FIGS. 2A–C. The effect of various concentrations of Compound No. 2 on RT activity in the supernatant of HIV-1-infected monocytes. FIG. 2A: Multiplicity of Infection (MOI) 1 ng p24/$10^6$ monocytes, cultured in presence of M-CSF. FIG. 2B: MOI 8 ng p24/$10^6$ monocytes, cultured in absence of M-CSF. FIG. 2C: MOI 0.8 ng p24/$10^6$ monocytes, cultured in absence of M-CSF.

Figure 3A:
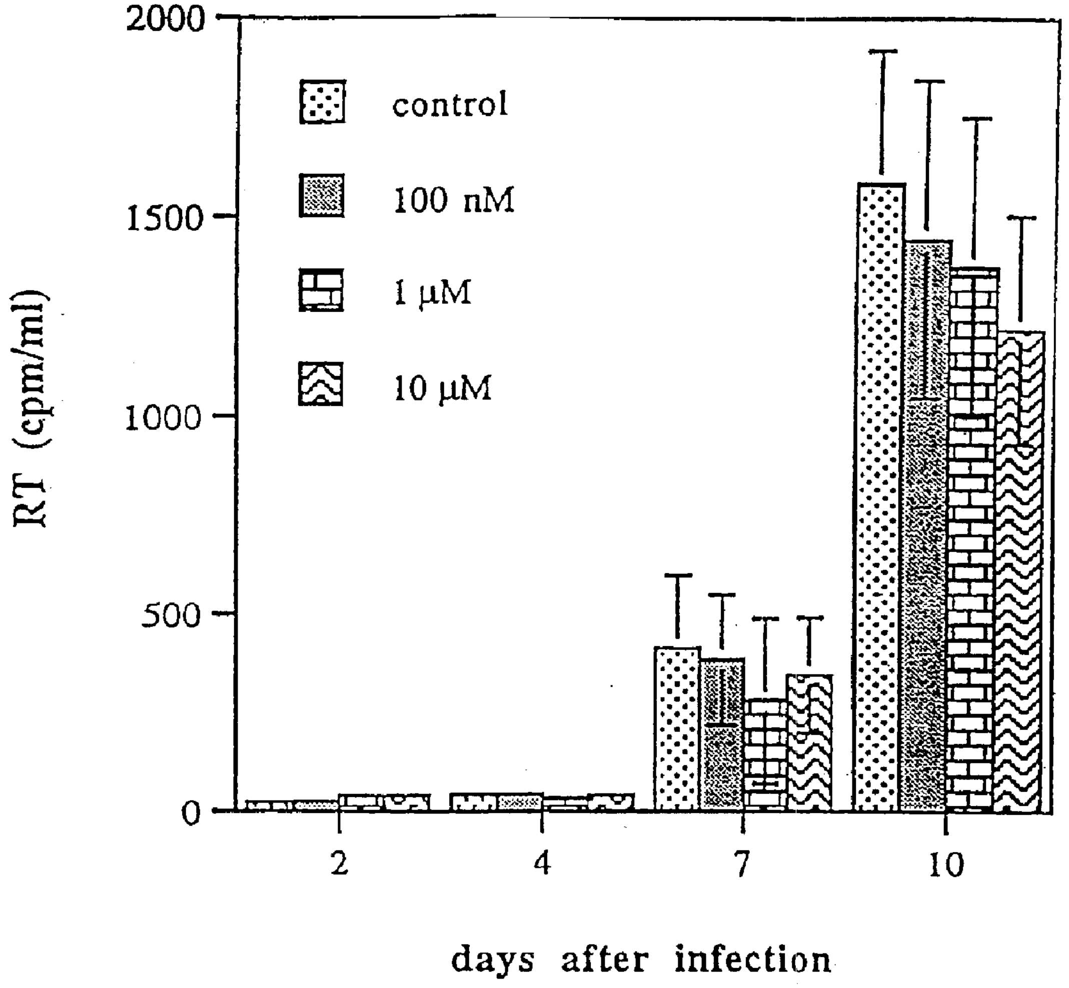
Figure 3B:
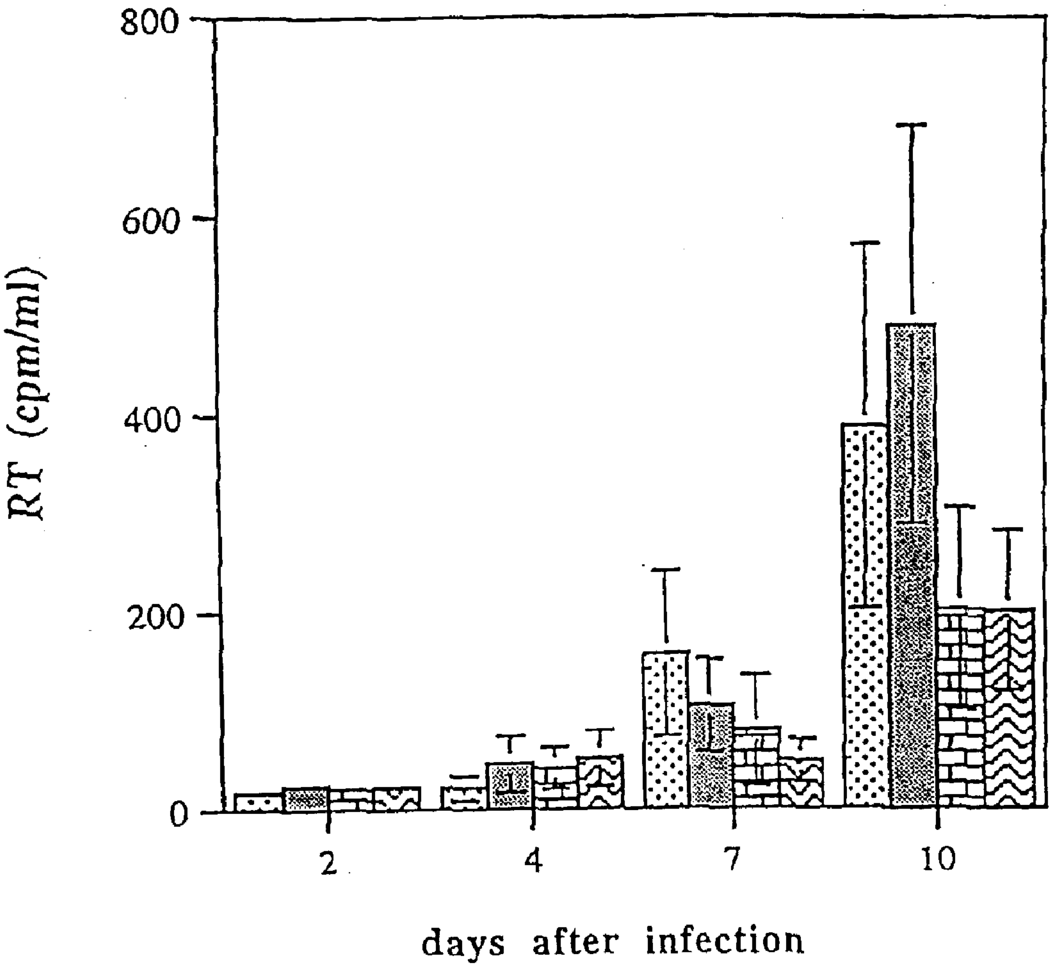

FIG. 3. The effect of various concentrations of Compound No. 2 on RT activity in the supernatant of HIV-1-infected mitogen-stimulated peripheral blood leukocytes at infected at 10 and 1.0 ng p24/$10^6$ cells, FIGS. 3A and 3B, respectively.

Figure 4A:
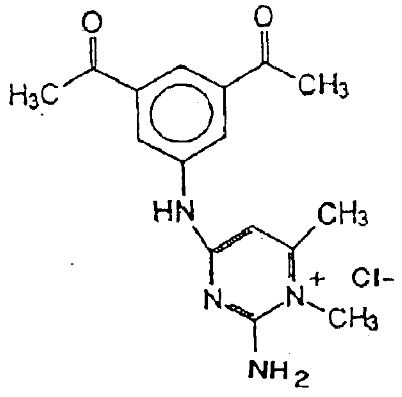
Figure 4B:
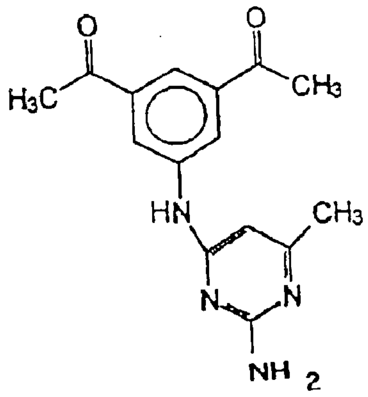
Figure 4C:
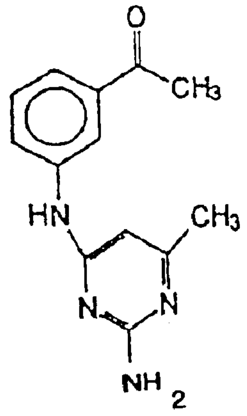
Figure 4D:
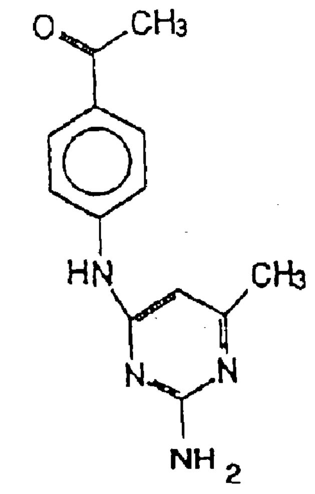
Figure 4E:
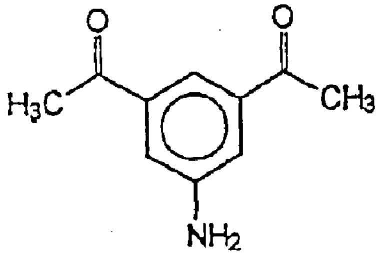
Figure 4F:
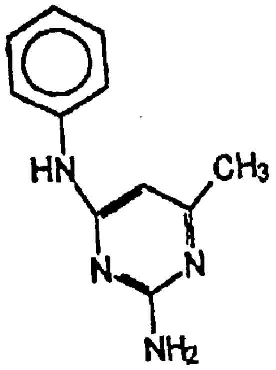

FIGS. 4A–F. The structures of the compounds used in Example 7 are shown respectively in FIGS. 4A–4F. FIG. 4A: 2-amino-4-(3,5-diacetylphenyl)amino-1,6-dimethylpyrimidinium chloride (CNI-0294). FIG. 4B: 2-amino-4-(3,5-diacetylphenyl)amino-6-methylpyrimidine (CNI-1194). FIG. 4C: 2-amino-4-(3-acetylphenyl)amino-6-methylpyrimidine (CNI-1594). FIG. 4D: 2-amino-4-(4-acetylphenyl)amino-6-methylpyrimidine (CNI-1794). FIG. E: 3.5-diacetylaniline (CNI-1894). FIG. 4F: 4-phenylamino-2-amino-6-methylpyrimidine (CNI-4594).

Figure 5:
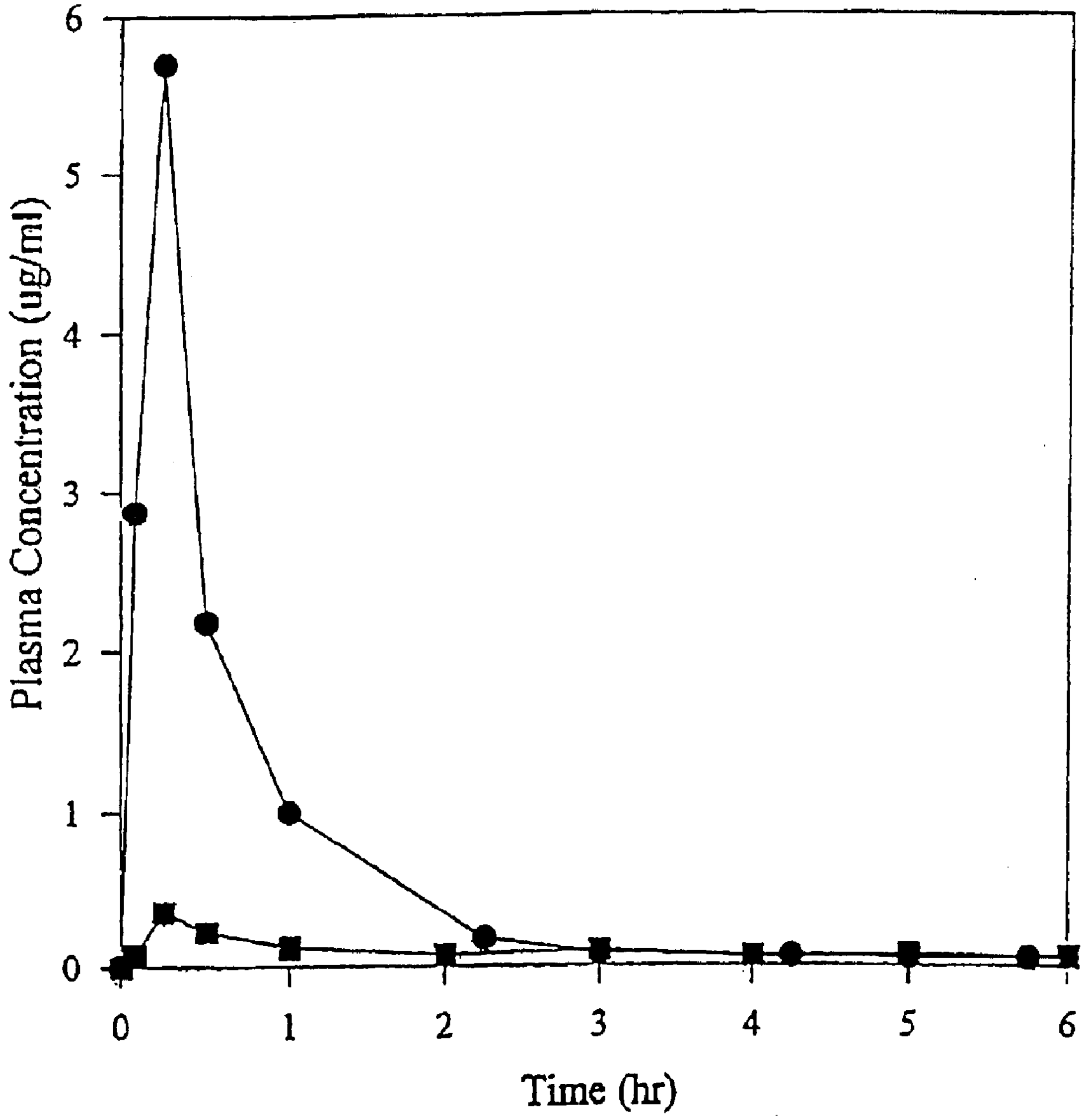

FIG. 5. Representative plasma concentrations over time in mice treated with CNI-1194. Female ND4 Swiss-Webster mice were given a single 50 mg/kg injection intraperitoneally (circles) or orally (squares). The calculated plasma concentrations, in μg/ml, was then plotted against the time of sampling.

Figure 6A:
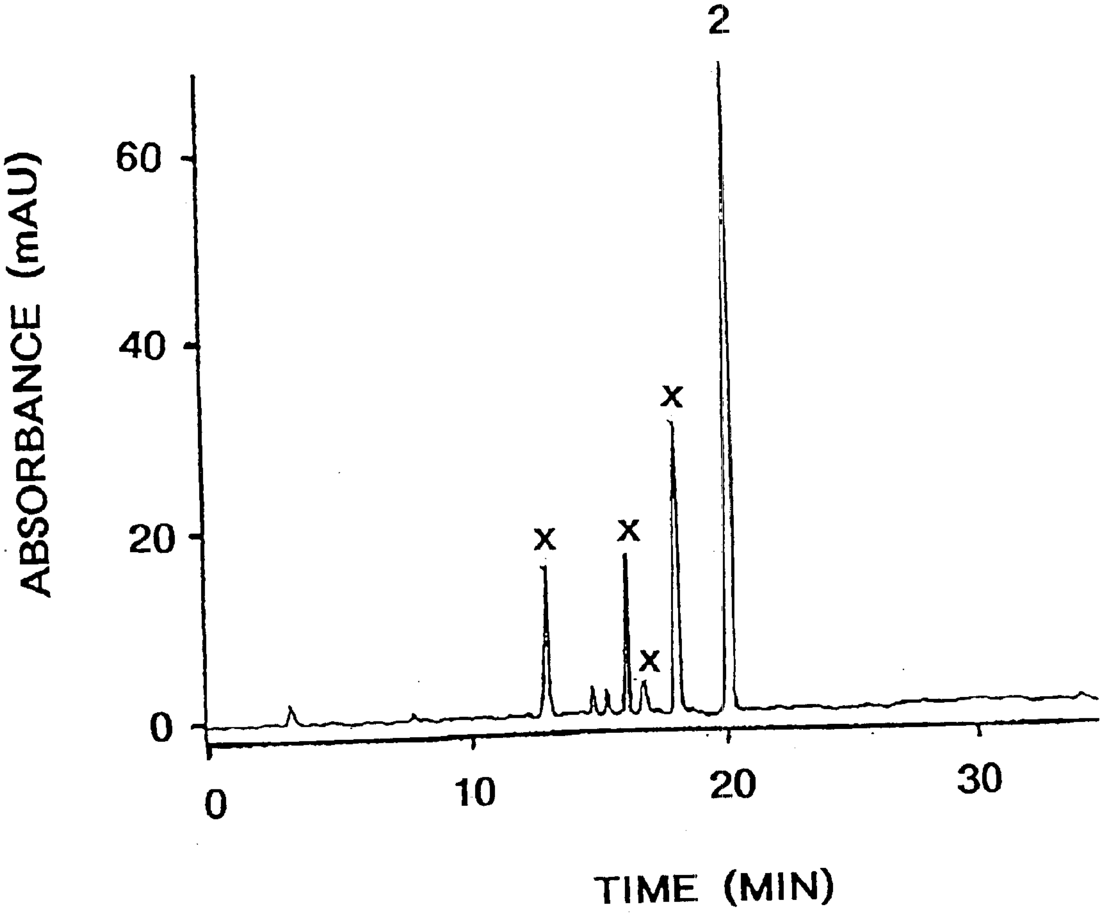
Figure 6B:
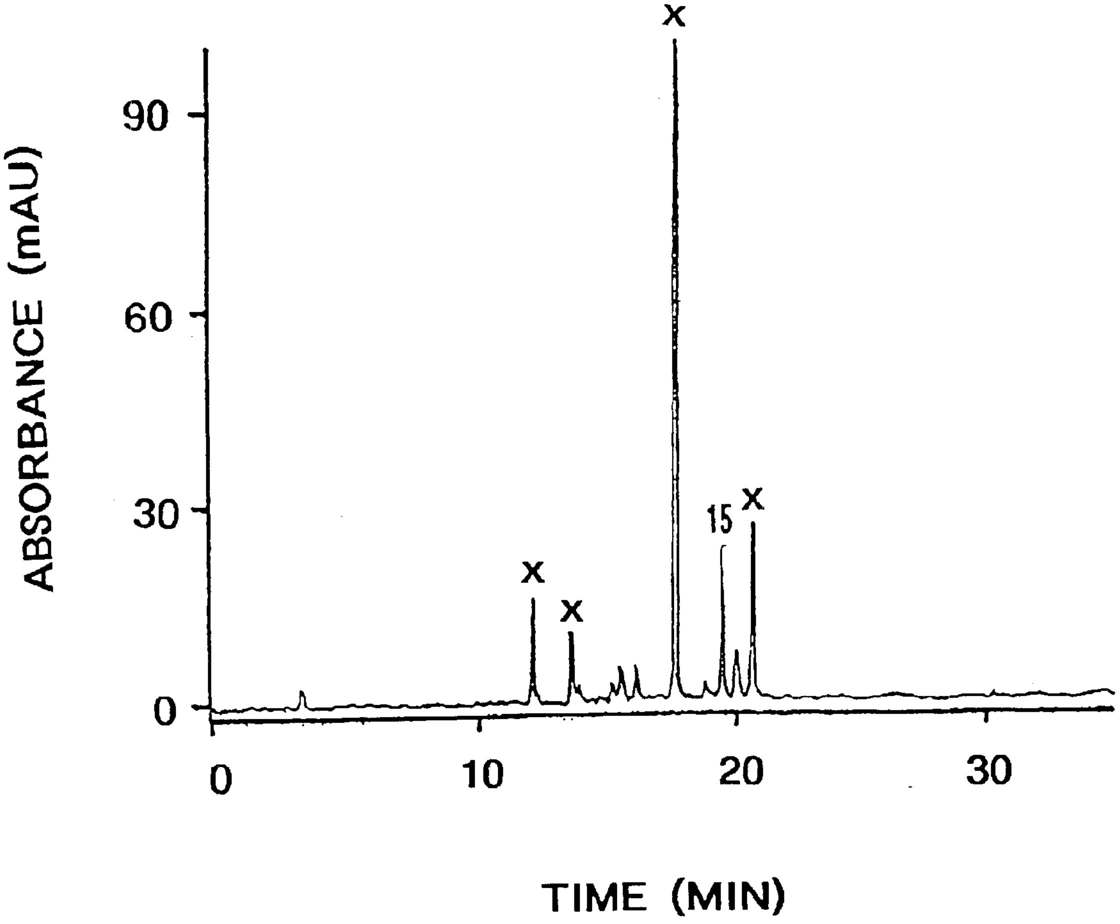
Figure 7A:
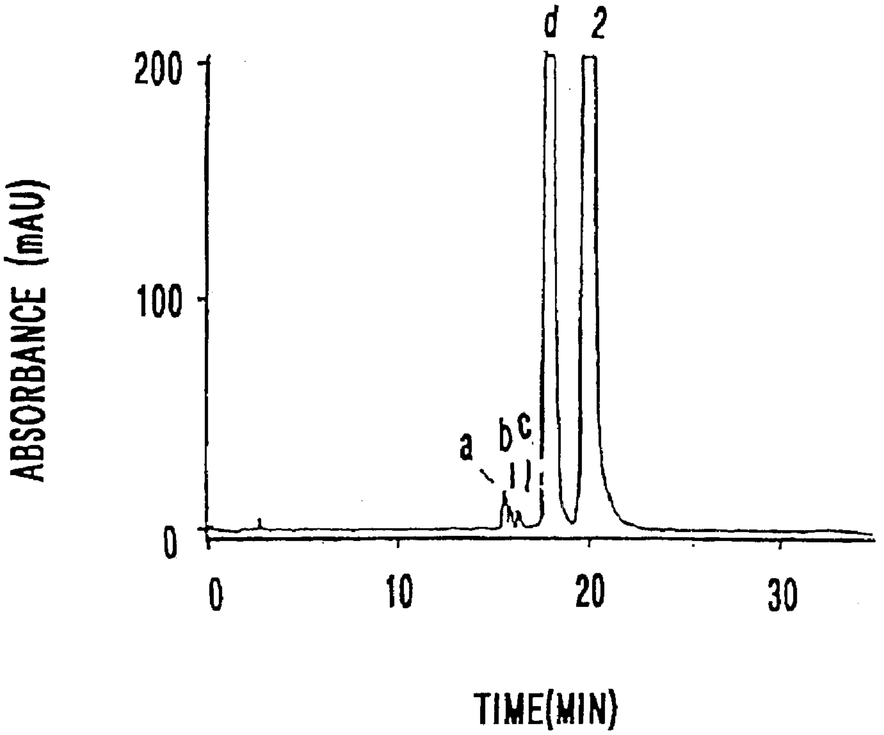
Figure 7B:
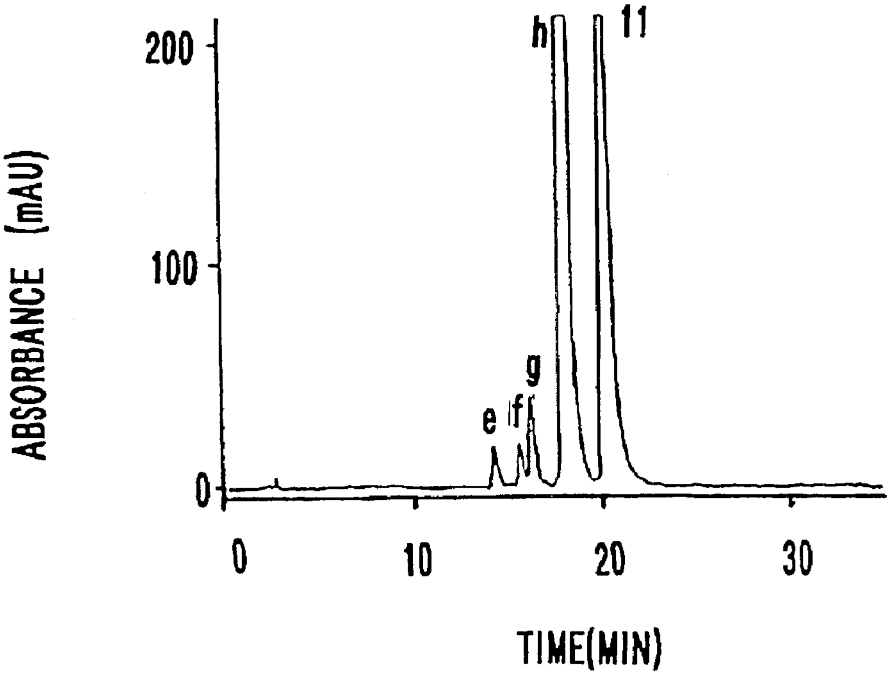
Figure 7C:
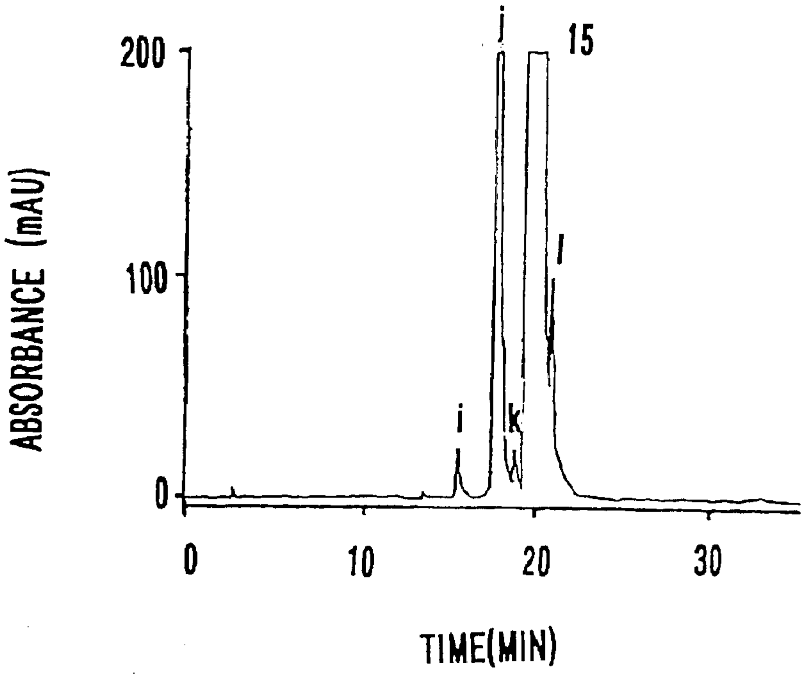
Figure 7D:
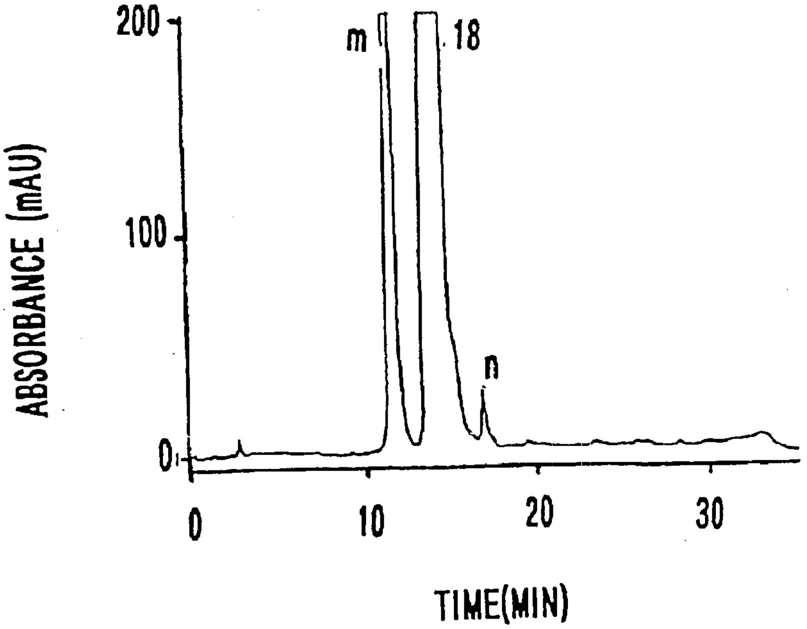
Figure 8A:
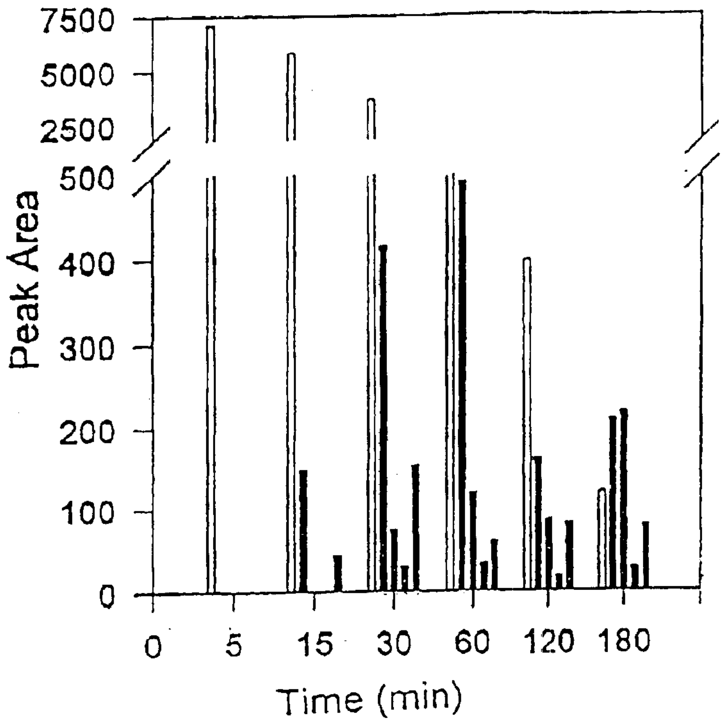
Figure 8B:
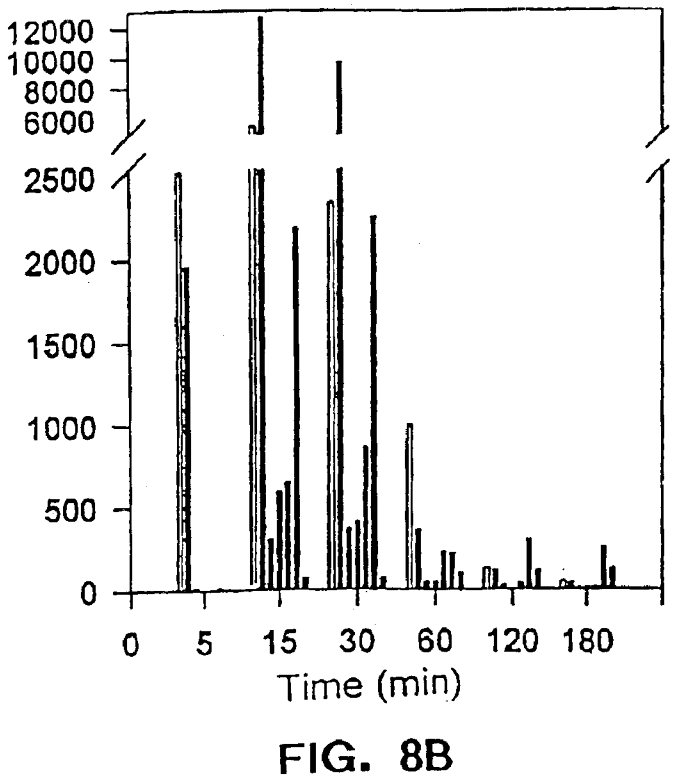
Figure 8C:
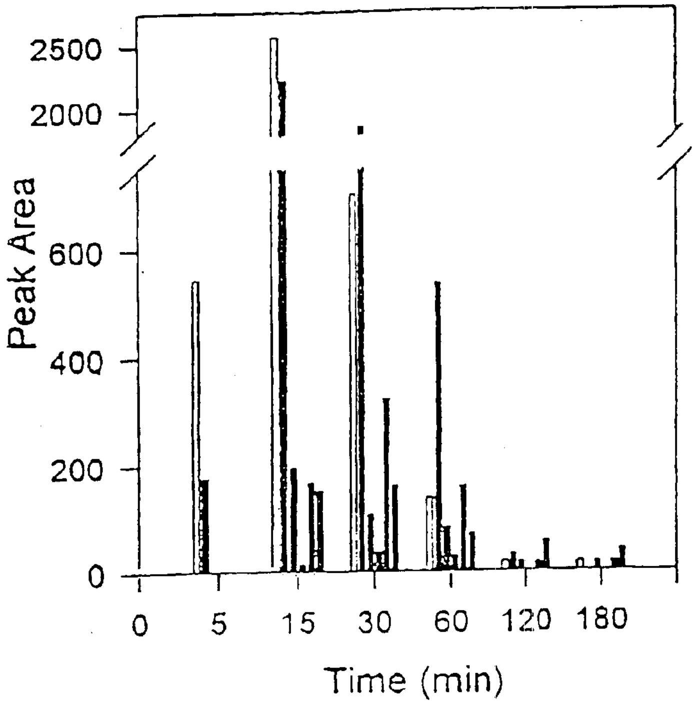
Figure 8D:
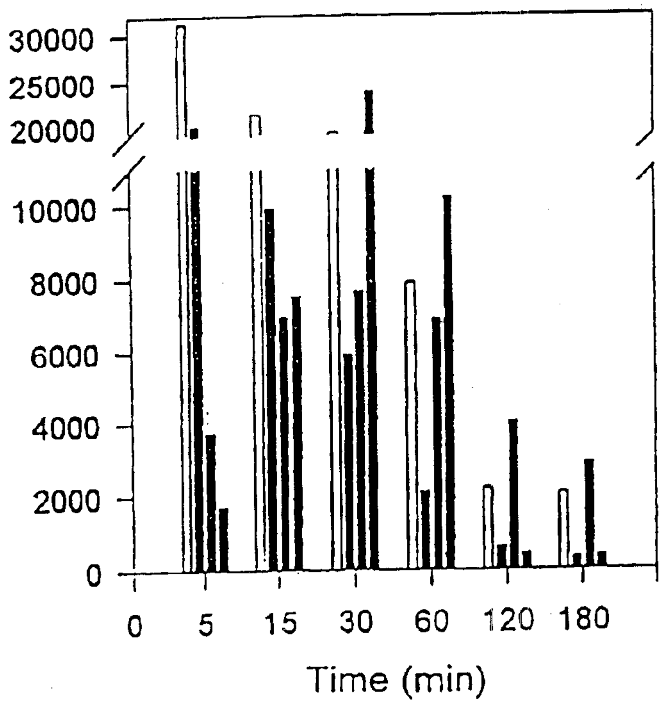

FIGS. 6A–6B. Chromatograms of plasma extracts from animals treated with CNI-0294 or CNI-1594. Female ND4 Swiss-Webster mice were given a single i.p. injection of 50 mg/kg CNI-0294 (A) or 20 mg/kg CNI-1594 (B). The chromatogram shown for CNI-0294 was from the 2 hr time point, and that for CNI-1594 for the 1 hr time point. The peaks labeled "2" and "15" are the parent peaks for CNI-0294 and CNI-1594 respectively. The other peaks in the chromatogram represent possible metabolites (labeled "x") and endogenous plasma peaks.

FIGS. 7A–7D. The in vitro metabolism of the CNI compounds. The drugs were incubated with mouse liver post-mitochondrial supernatants and NADPH for various lengths of time. The chromatograms shown are from the 60 min time point for (A) CNI-0294, (B) CNI-1194, (C)CNI-1594, and (D) CNI-1894. The peaks labeled "2, 11, 15, 18" refer to the parent compound peaks, and those labeled "a–n" to putative metabolite peaks that increased over time and were not present in control incubations. All off-scale peaks were single peaks, and the scale was chosen to allow presentation of trace metabolite peaks.

FIGS. 8A–8D. The in vivo metabolism of the CNI compounds. Female ND4 Swiss Webster mice received a single intraperitoneal dose of (A) 50 mg/kg CNI-0294, (B) 50 mg/kg CNI-1194, (C) 20 mg/kg CNI-1594, or (D) 50 mg/kg CNI-1894. In all four graphs, the open bar represents the peak area of the parent compound and the black bars the apparent metabolite peaks. The metabolite peaks shown are (from left to right in each graph): (a) peak "d" (see FIG. 7 for letter-designated peaks), peak "a", peak "c", and a peak eluting at 13 minutes; (b) peak "h", peak "e", peak "f", peak "g", a peak eluting at 14 minutes, and a peak eluting at 23 minutes; (C) peak "j", peak "i", peak "l", and a peak eluting at 14 minutes; (D) peak "m", peak "n", and a peak eluting at 11 minutes. The peak area units are arbitrary and calculated by the HPLC operating system.

Figure 9:
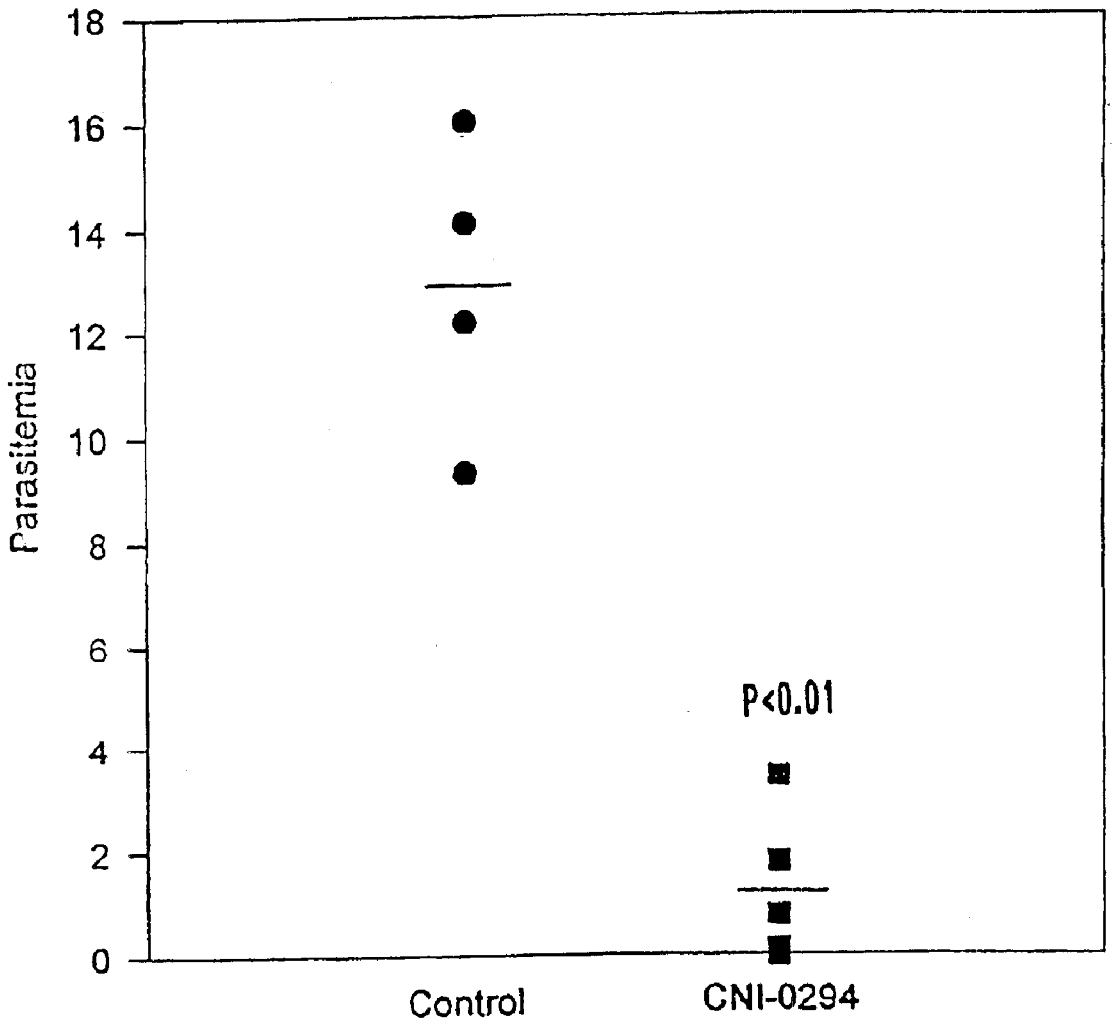

FIG. 9. The activity of CNI-0294 against *Plasmodium berghei* infected mice. Female ND4 Swiss Webster mice were infected with infected erythrocytes and then treated once daily, for four days, with 50 mg/kg CNI-0294, or with distilled water. Six hours after the last dose, thin blood smears were made from each of the animals and the parasitemia was determined. The bars represent the median parasitemia (n=4 for controls and n=5 for treated).

Figure 10A:
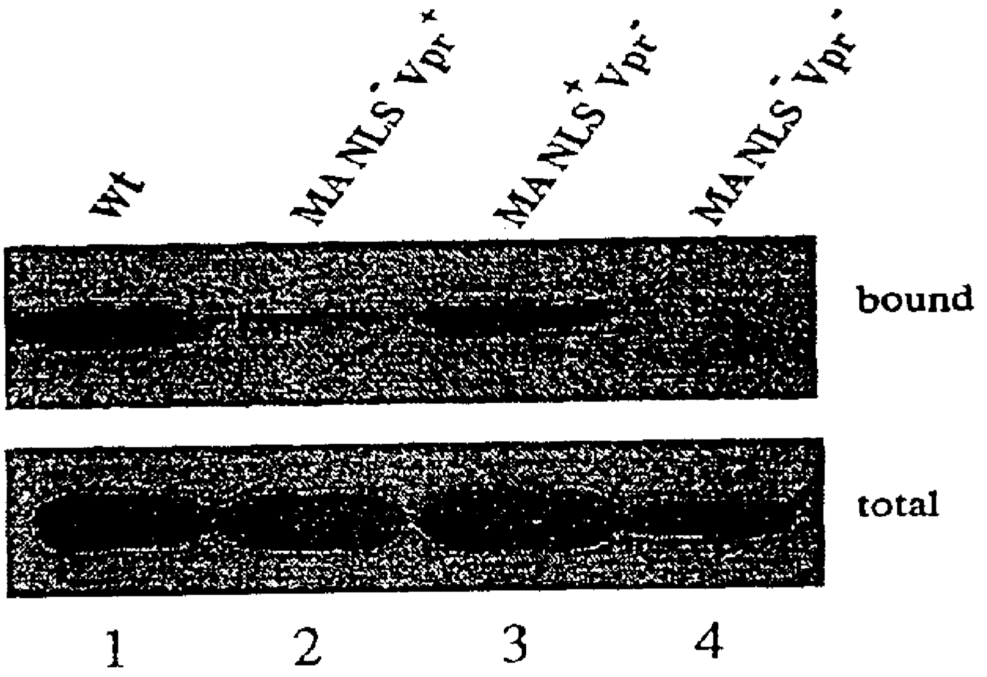
Figure 10B:
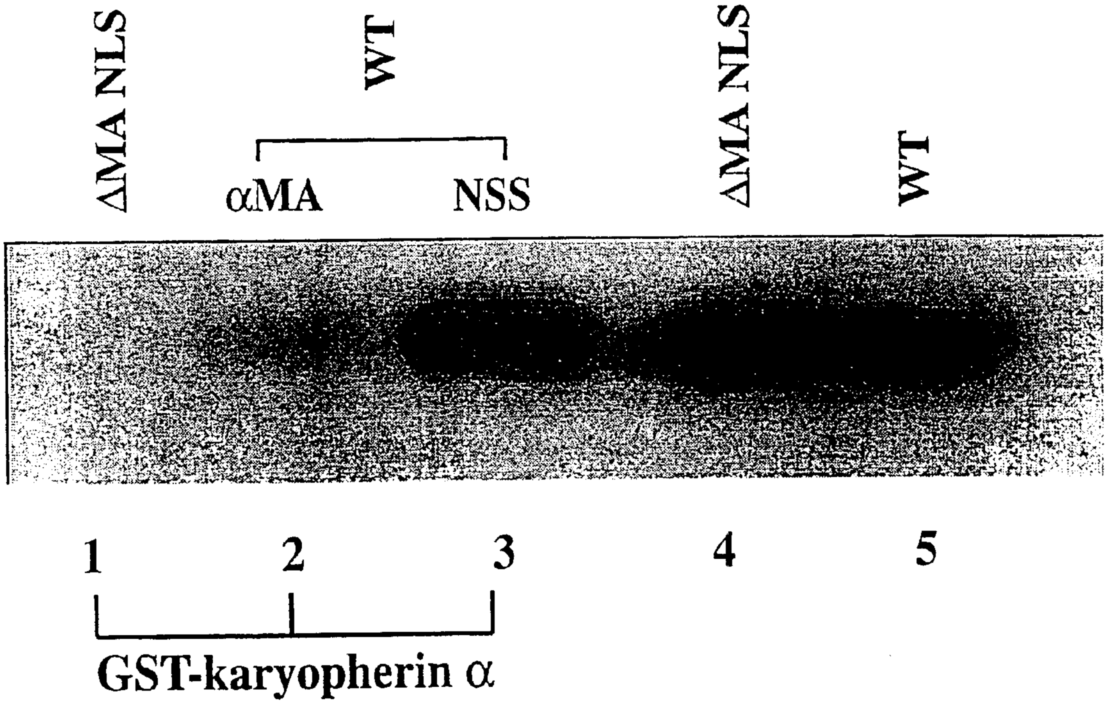
Figure 10C:
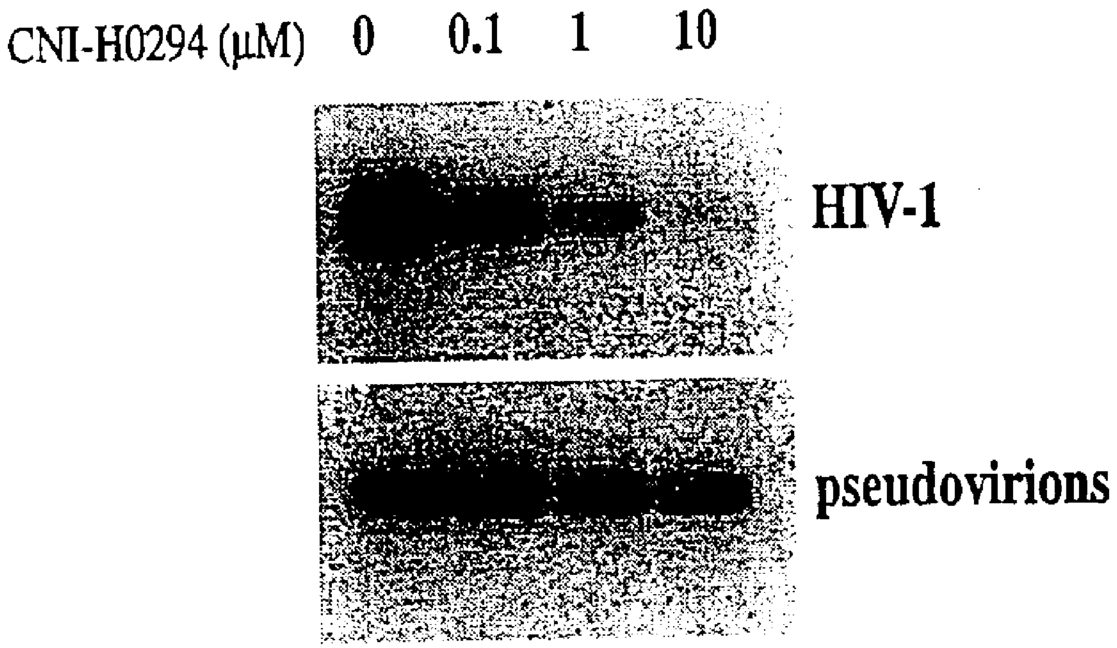

FIGS. 10A–10C. Binding of HIV-1 nucleoprotein complexes to karyopherin α.

A. Binding of HIV-1 to Karyopherin α is Mediated by Both MA and Vpr.

Cytoplasmic extracts prepared 4 hours after infection of H9 cells with equivalent amounts (100 ng of p24 per $10^6$ cells) of wild-type HIV-$1_{NLHX}$ or variants carrying inactivating mutations in MA NLS or/and Vpr were divided in two aliquots. DNA was extracted from one aliquot and quantified by PCR using primers specific for the HIV-1 pol gene (bottom panel). The obtained signal represented the total amount of the HIV-1 DNA in the cytoplasm. The second aliquot was incubated with GST-karyopherin α immobilized on Sepharose beads. HIV-1 DNA was extracted from the beads and analyzed by PCR using pol-specific primers. The obtained signal represented the amount of HIV-1 pre-integration complexes bound to karyopherin α.

B. Binding of HIV-1 Pseudovirion nucleoprotein complexes to karyopherin α is mediated by MA NLS.

H9 cells were inoculated with HIV-like gag-env pseudovirions that contain gag RNA; equal amounts of wild-type (wt) and mutant pseudovirions that carry amino acid substitutions in the MA NLS (AMA NLS) were used. Cytoplasmic extracts prepared from infected cells were incubated with polyclonal anti-MA serum (ΔMA, lane 2), pre-immune serum (NSS, lane 3), or nothing (lanes 1, 4, and 5). Samples were then mixed with GST-karyopherin α immobilized on glutathione Sepharose beads for 30 min at 25° C. Nucleic acids were extracted from Sepharose beads and quantified by RT-PCR using primers specific for HIV-1 gag gene. To control for possible differences in cell entry of wild-type vs. mutant agents, HIV-specific nucleic acids were extracted directly from cytoplasmic extracts and assayed by RT-PCR (lanes 4 and 5).

C. CNI-H0294 inhibits interactions of karyopherin α with HIV-1 pre-integration complexes, but not with pseudovirion-derived nucleoprotein complexes.

Cytoplasmic lysates of H9 cells infected with HIV-1RF (upper panel) or HIV-like pseudovirions (bottom panel) were treated for 2 hours with various concentrations of CNI-H0294, and were then mixed with GST-karyopherin α immobilized on glutathione Sepharose beads. HIV-1 DNA or RNA that co-precipitated with karyopherin α was quantified as in A and B.

Figure 11:
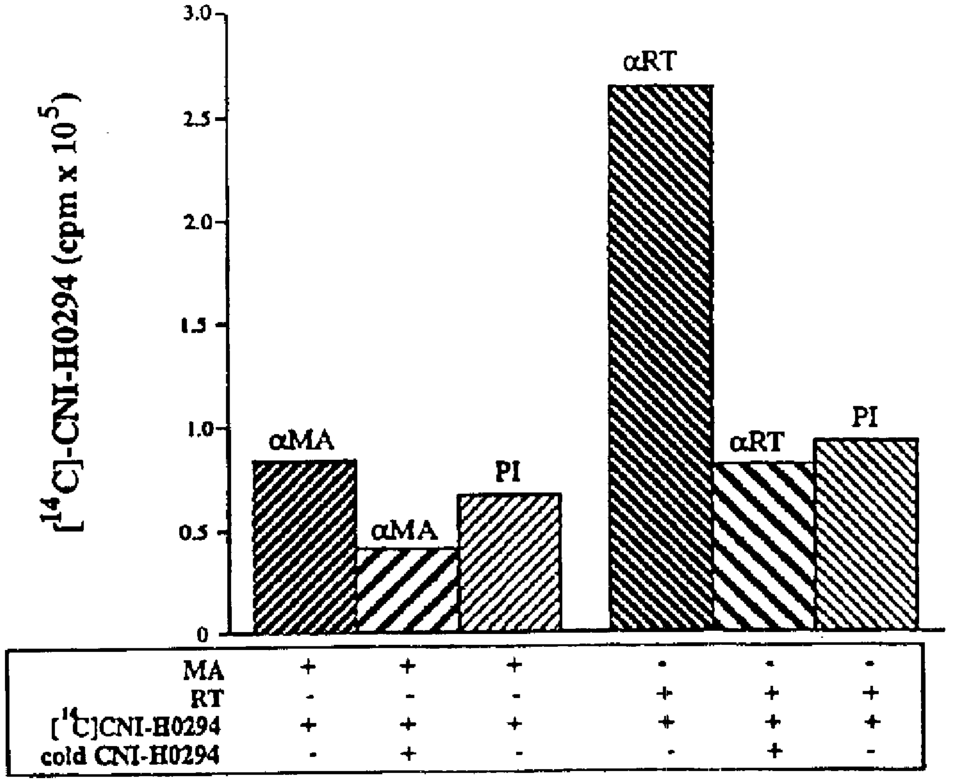

FIG. 11. CNI-H0294 binds to recombinant RT in solution.

Twenty nmol of [$^{14}$C]-CNI-H0294 were mixed with 0.28 nmol of recombinant MA or RT (a p51/p66 heterodimer) in 40 μl of binding buffer. Samples were incubated for 2 h at 37° C. in the presence or absence of 200 nmol of unlabeled CNI-H0294. MA and RT proteins were immunoprecipitated using protein G agarose and sheep polyclonal anti-MA (αMA) or rabbit anti-RT (αRT) sera, respectively. Pre-immune sera (PI) was used as control. Bound material was eluted from protein G using 0.1 M glycine buffer [pH 2.8] and the radioactivity in the eluate was quantified in a scintillation counter.

Figure 12A:
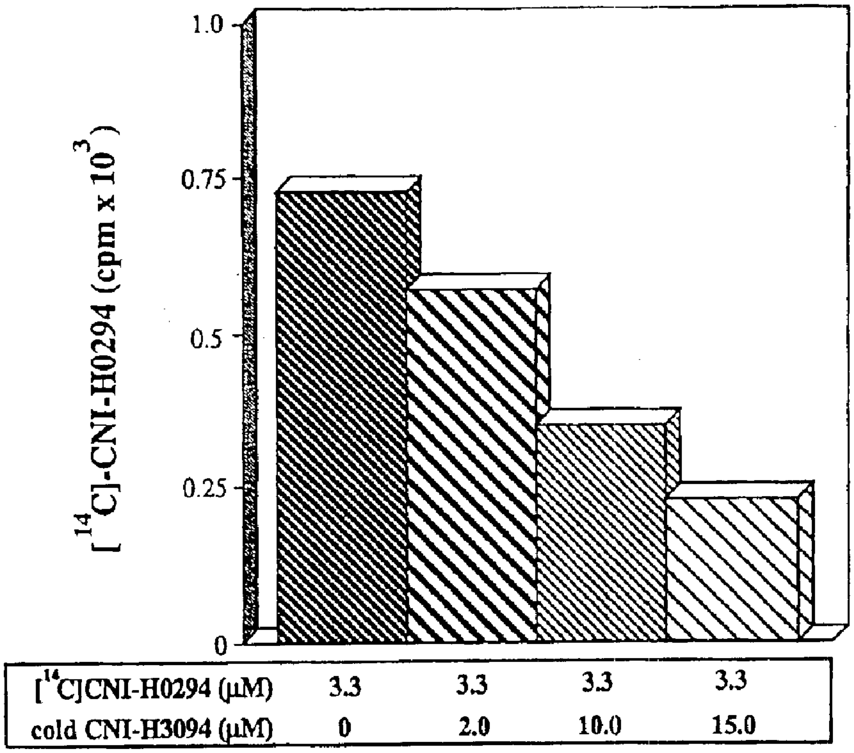
Figure 12B:
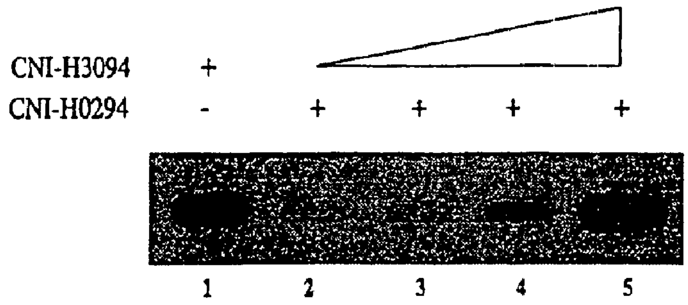
Figure 12C:
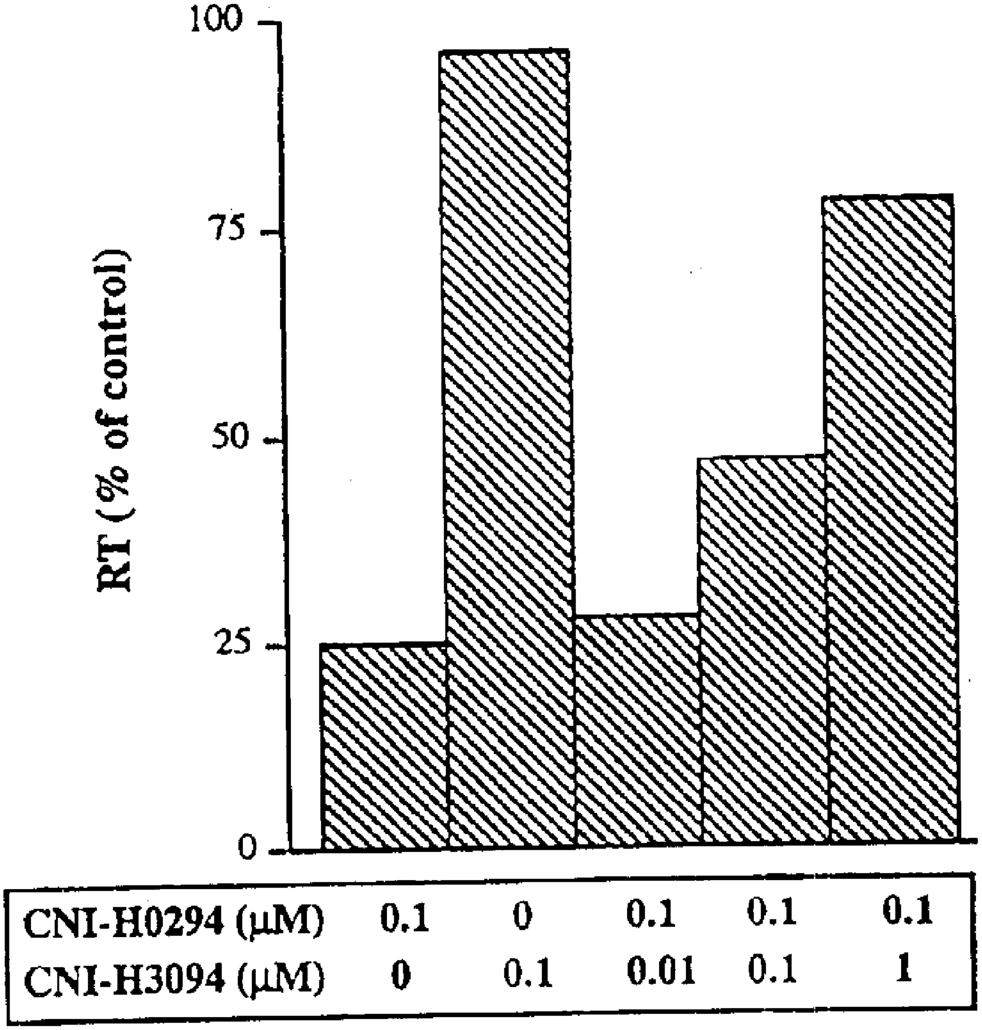

FIGS. 12A–12C. CNI-H0294 interacts with RT to produce the anti-HIV effect.

A. CNI-H3094 competes with CNI-H0294 for binding to RT.

Recombinant RT (0.2 μM) was incubated with 3.3 μM of [$^{14}$C]-labeled CNI-H0294 and increasing concentrations of unlabeled (cold) CNI-3094. The amount of [$^{14}$C]-CNI-H0294 that bound to RT was measured as in FIG. 11.

B. CNI-H3094 reduces CNI-H0294-mediated inhibition of HIV-karyopherin α interaction.

Cytoplasmic lysates prepared from H9 cells infected with HIV-1RF were treated with 10 μM CNI-H3094 (lane 1) or with 1 μM CNI-H0294 and 10 μM (lane 5), 5 μM (lane 4), 1M (lane 3), or no CNI-H3094 (lane 2). The amount of pre-integration complexes available for interaction with karyopherin α was quantified as in FIG. 10.

C. CNI-H3094 inhibits anti-HIV activity of CNI-H0294 in monocyte cultures.

Monocytes infected with HIV-$1_{ADA}$ were cultured in the presence of CNI-H0294 and CNI-H3094 in various concentrations. Nine days after infection, RT activity in culture supernatants was quantified. The results are presented as percent of total RT activity in untreated cultures (control). Three independent samples were assayed for each drug concentration, and the standard deviation was less than 15%.

Figure 13A:
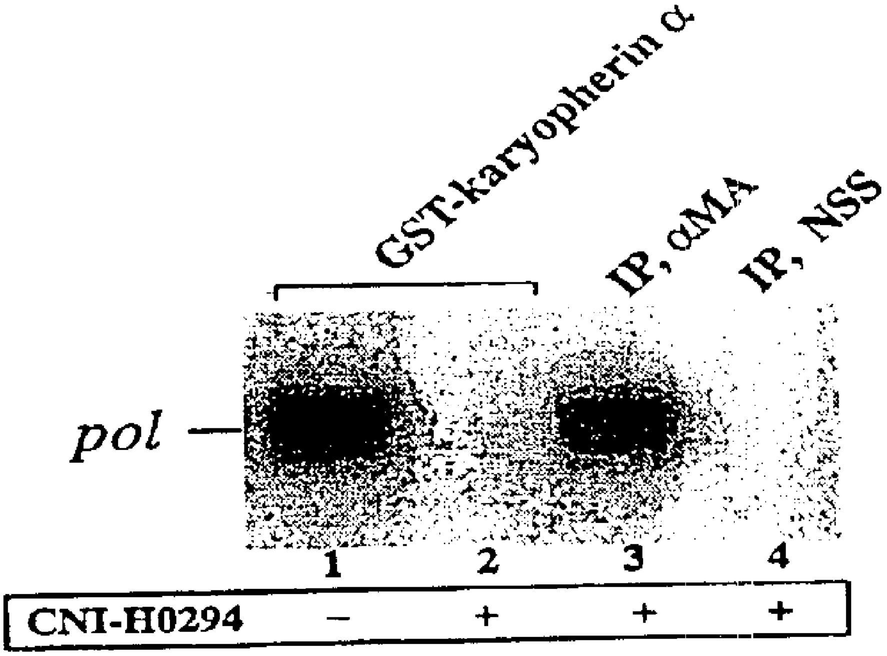
Figure 13B:
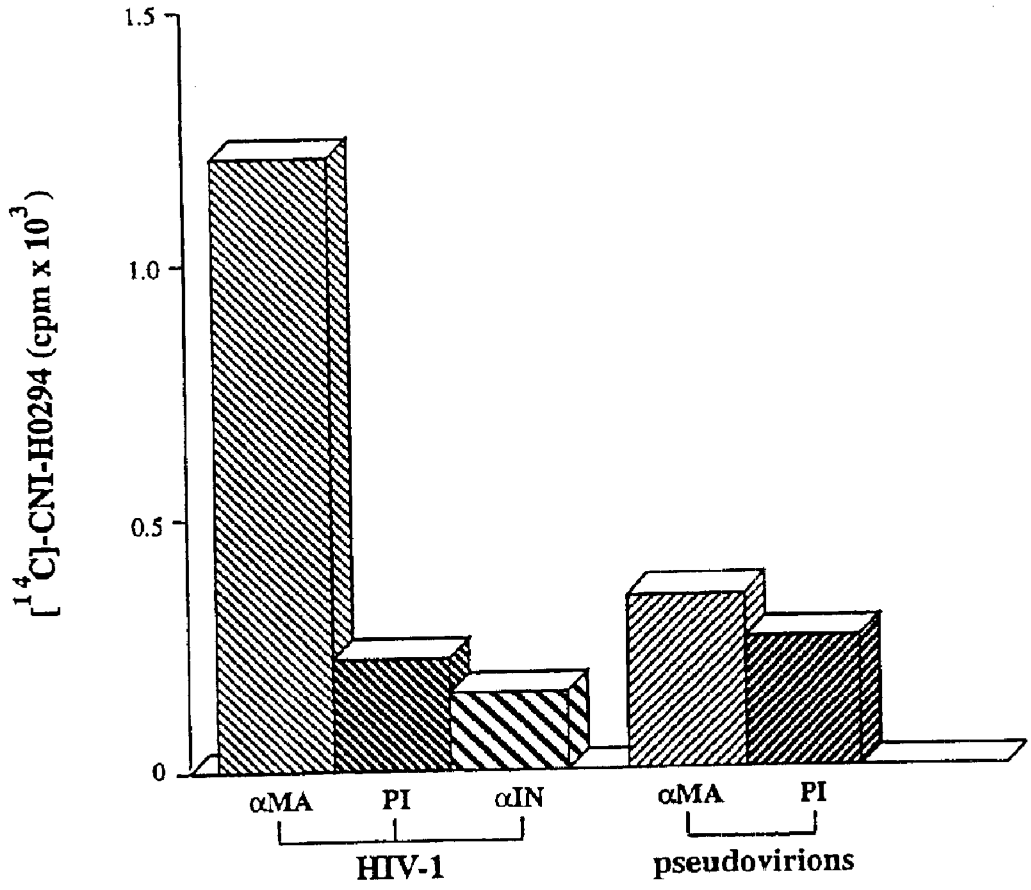

FIGS. 13A–13B. Analysis of CNI-H0294 interactions with the HIV-1 pre-integration complex.

A. CNI-H0294 does not disrupt the interaction between MA and HIV-1 cDNA.

Cytoplasmic extracts prepared from H9 cells infected with HIV-1RF were treated with 10 μM CNI-H0294 (lanes 2, 3, and 4) or left untreated (lane 1). Samples were divided into two aliquots. One aliquot was mixed with GST-karyopherin α immobilized on Sepharose beads and the HIV-1 DNA that bound was quantified by PCR. The second aliquot was immunoprecipitated (IP) with anti-MA serum (αMA, lane 3) or with pre-immune serum (NSS, lane 4) as control.

B. CNI-H0294 reacts with MA, but only when MA is associated with the HIV-1 pre-integration complex.

Cytoplasmic extracts from HIV-1RF-infected H9 cells were treated with [$^{14}$C]CNI-H0294 (10 μM). After borohydride reduction the extracts were immunoprecipitated with anti-MA (αMA), anti-IN (αIN), or pre-immune serum (PI). As control, similar reactions were performed using lysates of pseudovirion-infected cells which lack RT and thus do not bind CNI-H0294. Immunoprecipitated radioactivity was quantified in a scintillation counter.

Figure 14A:
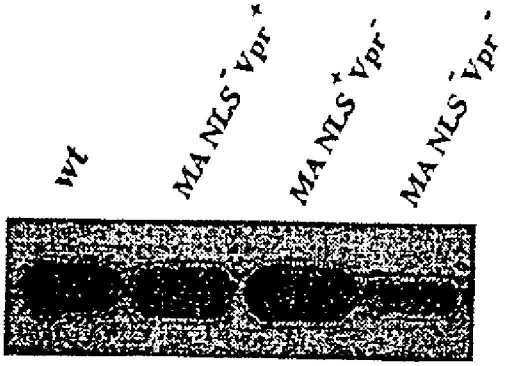
Figure 14B:
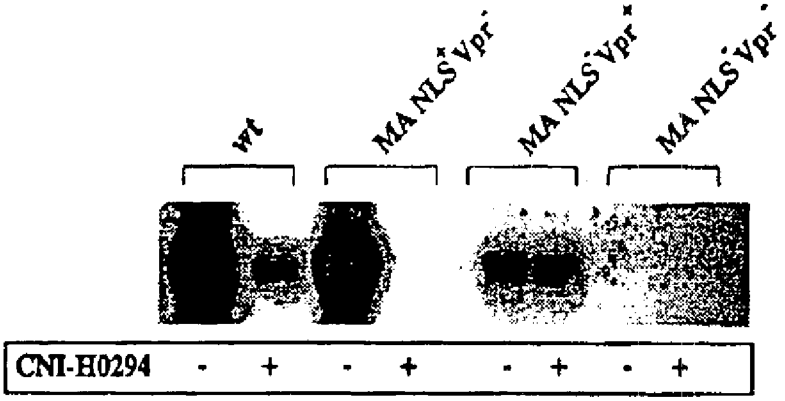

FIGS. 14A–14B. CNI-H0294 inhibits MA-, but not Vpr-mediated binding of HIV-1 pre-integration complexes to karyopherin α.

H9 cells were infected with equal amounts of wild-type HIV-$1_{NLHX}$ or with mutant HIV-$1_{NLHX}$ that lack Vpr (Vpr$^-$) or carry a mutation that inactivates the MA NLS (MA NLS$^-$). Infected cells were washed and incubated for 4 h. An aliquot of each sample was used to quantify the total HIV-1 DNA (FIG. 14A) and the rest was used to prepare cytoplasmic extracts. Extracts were incubated with 1 μM CNI-H0294 (FIG. 14B, lanes 2, 4, 6, 8) or were left untreated (lanes 1, 3, 5, 7). The amount of pre-integration complexes available for binding to karyopherin α was determined as in FIG. 10.

Figure 15:
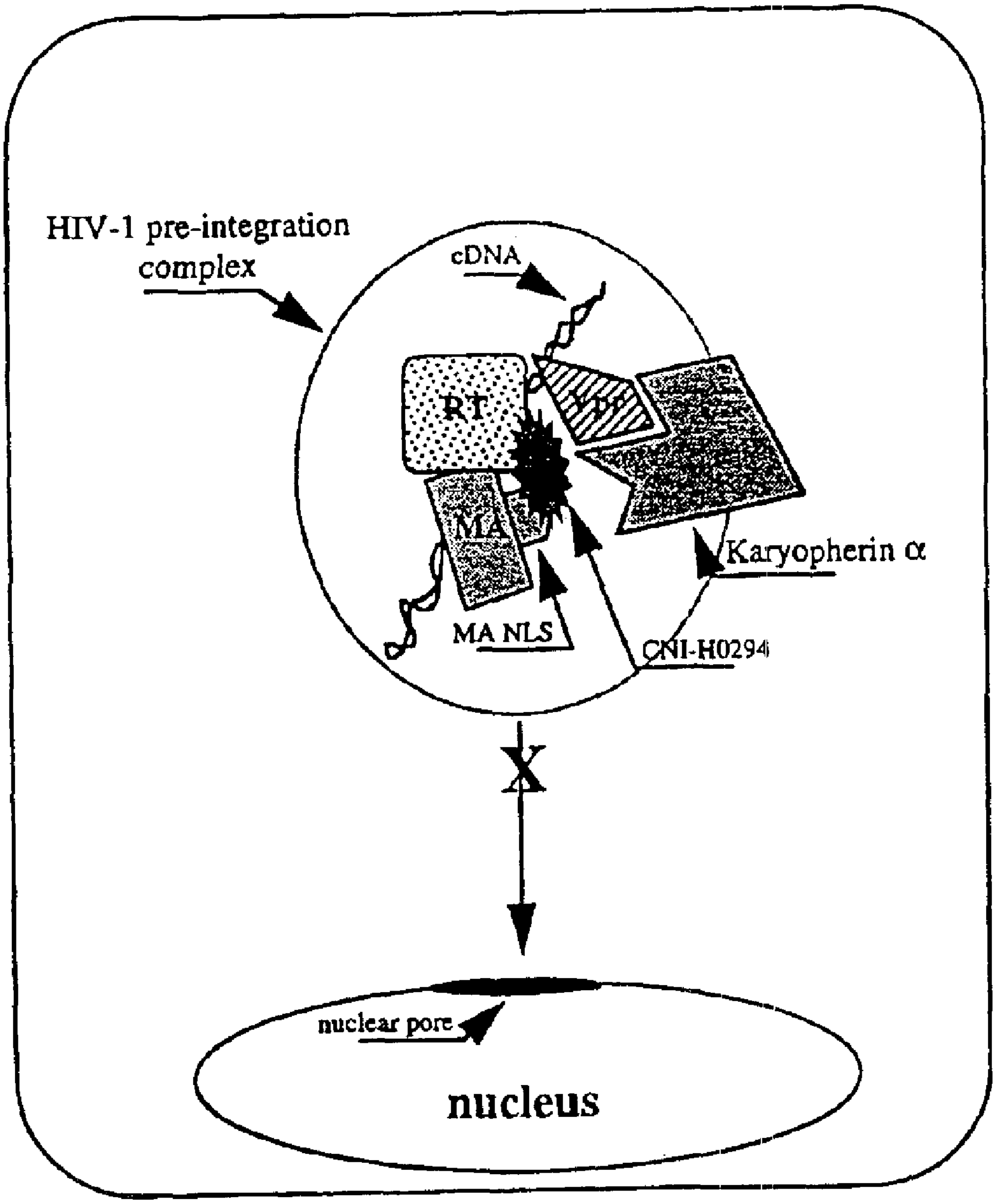

FIG. 15. Proposed mechanism of CNI-H0294 action.

CNI-H0294 binds to HIV-1 pre-integration complexes via RT, and then reacts with an adjacent MA NLS. This interaction prevents binding of karyopherin α to MA NLS; this nearly abolishes nuclear import of the pre-integration complexes. Note that Vpr binds to karyopherin α even in the presence of CNI-H0294; this explains the low level of import detected in the presence of the drug.

5 DETAILED DESCRIPTION OF THE INVENTION

5.1 The Compounds and Methods of Their Synthesis

The present invention encompasses a class of alkyl aryl carbonyl compounds that forms stable, but preferably reversible, and most preferably reversible covalent interactions with one or more basic amino acid residues, wherein such basic amino acid residues are a part of a nuclear localization signal (NLS). The stable covalent interaction results in the inhibition or neutralization of the nuclear localization activity of the NLS.

Two structural features are involved in conferring such capabilities of a compound of the invention: (a) a moiety comprising at least one carbonyl group that reacts with the side chains of basic amino acid residues in the target protein, i.e., the reactive group; and (b) a second moiety, i.e., the targetting group, that interacts with a specific docking site and determines the specificity of the compound for different NLS.

Although the reactive group(s) of the compounds of the invention can react reversibly with any susceptible basic side chains in a protein, e.g., arginines and lysines, the interaction between the targetting group and the docking site confers specificity to the activity of the carbonyl group(s), such that the carbonyl group(s) react only with particular target residue(s) in a protein. This targetting function occurs by interaction of the targetting group with a docking site that is located proximately to the susceptible side chains of basic amino acid residues of the target NLS, such that docking of the compound places it in a favorable configuration to form a stable interaction with the side chains of the basic amino acid residues of the target NLS. It is to be understood that the docking site is located either on the same NLS-bearing protein, or on another component of a larger molecular complex that includes the NLS-bearing protein.

Preferred compounds of the invention provide divalent aryl carbonyl moieties as the reactive group, particularly aryl bis(ketone) or aryl bis(α-diketone), aryl bis(β-diketone), linked to a targetting group, preferably to a nitrogen-containing heterocyclic functionality via an N-linkage. Particularly preferred compounds provided are bis acetyl, propanoyl, glyoxyloyl, pyruvoyl, 2-oxobutanoyl, acetoacetyl, 3-oxopentanoyl, 3-oxo-2,2-dimethylbutanoyl or 3-oxo-2,2-dimethylpentanoyl substituted aniline moieties N-linked to a pyrimidinium, pyrimidine or triazine moiety.

The compounds of the present invention form reversible adducts with a target NLS containing protein. In particular, the compounds form-Schiff bases with adjacent lysine residues, and other reversible adducts with adjacent arginine residues. Thus, the compounds of the invention, e.g., aryl bis(ketone), can advantageously be used for inactivation of an NLS where the NLS comprises lysine residues. On the other hand, where the NLS contains arginine residues, aryl bis(diketone) compounds, particularly dimethyl-substituted compounds, i.e., those lacking a methylene hydrogen between the ketones, can be used advantageously.

In one particular embodiment, the compounds of the invention are capable of forming Schiff bases with lysine residues of a target NLS containing protein in a molecular complex, and interacting with a specific docking site on a molecule in the molecular complex, said docking site being positioned proximately to the lysine residues in the protein. Because of the proximity of the target lysine residues to the docking site, the interaction of the targetting group with the docking site localizes the compound of the invention to the vicinity of the target lysine residues, thereby facilitating the reaction of the carbonyl group(s) of the compound with the target $N^{\epsilon}$ group of lysine residue(s) in the NLS, and resulting in the formation of stable Schiff bases and inactivation of the NLS.

Specific compounds of the invention, e.g., compound No. 2 or CNI-H0294, or 2-Amino-4-(3,5-diacetylphenyl)amino-1,6-dimethylpyrimidinium salts, and their synthesis are described in section 6 et seq, and are disclosed in earlier filed U.S. patent application Ser. Nos. 08/369,830, 08/463,405, 08/471,797, 08/470,103, and 08/584,857 each of which is hereby incorporated by reference.

According to the invention, the compounds of the invention are alkyl aryl carbonyl compounds of formula (I)

(I)

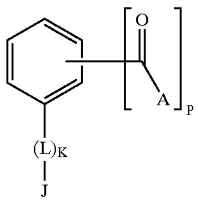

wherein A, independently, $=CH_3$, $CH_2CH_3$, COH, $COCH_3$, $COCH_2CH_3$, $CH_2COCH_3$, $CH_2COCH_2CH_3$, $C(CH_3)_2COCH_3$, $C(CH_3)_2COCH_2CH_3$ or the like to yield an acetyl, propanoyl, glyoxyloyl, pyruvoyl, 2-oxobutanoyl, acetoacetyl, 3-oxopentanoyl, 3-oxo-2,2-dimethylbutanoyl or 3-oxo-2,2-dimethylpentanoyl substituted aniline; P=1 or 2; L is a linker group containing an S, O, N or C atom, e.g., $—SO_2—$, —O—, —NH—, —N=, $—CH_2—$ or —CH=; K is 0 or a positive integer, preferably K=1; and wherein J represents (i) a saturated or unsaturated, substitued or unsubstituted, straight or branched acyclic hydrocarbon group; (ii) a saturated or unsaturated, substitued or unsubstituted, straight or branched acyclic group containing hetero atoms such as nitrogen, sulfur or oxygen; (iii) a substituted or unsubstituted, saturated or aromatic, mono- or poly-cyclic group having 3 to 20 carbon atoms; or (iv) a substituted or unsubstituted, saturated or aromatic, mono- or poly-heterocyclic group having 3 to 20 atoms, at least one of which is a nitrogen, sulfur or oxygen. The compounds of the invention can contain one or more linker groups (L), however, if J contains a linker group as defined above, K can be 0.

The acyclic and cyclic groups defined above may be saturated or unsaturated and may, if desired, bear one or more substituents. Exemplary of such substituents are alkyl, alkoxy, phenoxy, alkenyl, alkynyl, phenylalkyl, hydroxyalkyl, haloalkyl, aryl, arylalkyl, alkyloxy, alkylthio, alkenylthio, phenylalkylthio, hydroxyalkyl-thio, alkylthiocarbamylthio, phenyl, cyclohexyl, pyridyl, piperidinyl, alkylamino, amino, nitro, mercapto, cyano, hydroxyl or a halogen atom.

For example, J can be a substituted or unsubstituted five or six membered ring having 1–4 hetero ring atoms, at least one of which is nitrogen, the remainder of which are selected from nitrogen, oxygen or sulfur, e.g., pyridine, pyrrole, imidazole, thiazole, isothiazole, isoxazole, furazan, pyrrolidine, piperidine, imidazolidine, piperazine, oxazole, tetrazole, pyrazole, triazole, oxadiazole, thiodiazole. Alternatively, J can be a substituted or unsubstituted poly-cyclic group having 1 to 4 hetero ring atoms, one of which is nitrogen and the remainder of which are nitrogen, oxygen or sulfur, e.g., indole, quinoxaline, quinazoline, quinoline, isoquinoline, purine.

By the term "alkyl" as used herein is meant a straight or branched chain saturated hydrocarbon group having from 1 to 20 carbons such as methyl, ethyl, isopropyl, n-butyl, s-butyl, t-butyl, n-amyl, isoamyl, n-hexyl, n-octyl and n-decyl. The terms "alkenyl" and "alkynyl" are used to mean straight or branched chain hydrocarbon groups having from 2 to 10 carbons and unsaturated by a double or triple bond respectively, such as vinyl, allyl, propargyl, 1-methylvinyl, but-1-enyl, but-2-enyl, but-2-ynyl, 1 methylbut-2-enyl, pent-1-enyl, pent-3-enyl, 3-methylbut-1-ynyl, 1,1-dimethylallyl, hex-2-enyl and 1-methyl-1-ethylallyl. The term "phenylalkyl" means the aforementioned alkyl groups substituted by a phenyl group such as benzyl, phenethyl, phenopropyl, 1-benzylethyl, phenobutyl and 2-benzylpropyl. The term "aryl" as used herein is meant to include a monocyclic, bicyclic, tricyclic or other polycyclic compounds, wherein at least one ring is aromatic including aromatic hydrocarbons or hetero-aromatic hydrocarbons having heteroaromatic atoms such as nitrogen, sulfur and oxygen. The term "hydroxy-alkyl" means the aforementioned alkyl groups substituted by a single hydroxyl group such as 2-hydroxyethyl, 2-hydroxypropyl, 3-hydroxypropyl, 4-hydroxybutyl, 1-hydroxybutyl and 6-hydroxyhexyl. The terms "alkylthio, alkenylthio, alkynylthio, hydroxy-alkylthio and phenyl-alkylthio" as used herein mean the aforementioned alkyl, alkenyl, alkynyl, hydroxy-alkyl and phenyl-alkyl groups is linked through a sulfur atom.

The term "substituted" as used herein means that the group in question, e.g., alkyl group, aryl group, etc., may bear one or more substituents including but not limited to halogen, hydroxy, cyano amino, nitro, mercapto, carboxy and other substituents known to those skilled in the art.

The terms "saturated" as used herein means an organic compound with neither double or triple bonds. The term "unsaturated" as used herein means an organic compound containing either double or triple bonds.

In another embodiment, the compounds of the invention are formed according to formula (II):

(II)

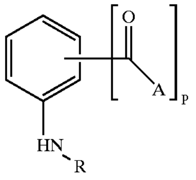

wherein A, independently, $=CH_3$ or $CH_2CH_3$ and P=1 or 2; and (1)

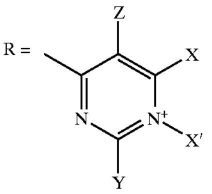

(2)

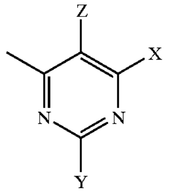

wherein $X{=}NH_2$, $CH_3$ or $CH_2CH_3$; $X'{=}CH_3$ or $CH_2CH_3$; $Y{=}NH_2$, $NHCH_3$, $N(CH_3)_2$, 1-pyrrolidino or 1-piperidino; and Z=H, $CH_3$ or $CH_2CH_3$; or (3)

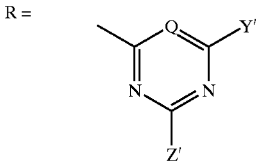

(4)

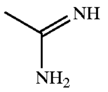

(5)

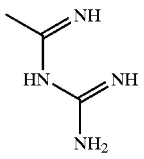

(6)

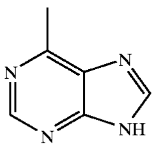

wherein Y' and Z', independently, =H, $NH_2$, $NHCH_3$, $N(CH_3)_2$ or $N^+$ $(CH_3)_3$, 1-pyrrolidino or 1-piperidino; Q is N or CH; and salts thereof.

In a preferred embodiment the compounds of the invention are bis ketone arylene compounds having a third nitrogenous substituent. The nitrogenous substituent can be further substituted with an aromatic nitrogen-containing heterocyclic compound.

More precisely the bis ketone arylene compounds of the invention are formed according to the formula (III):

(III)

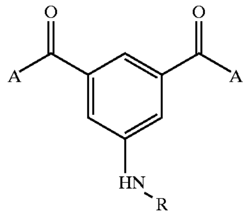

wherein $A{=}CH_3$ or $CH_2CH_3$ and (1)

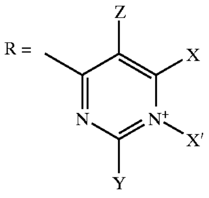

(2)

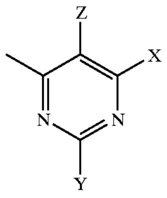

wherein $X{=}NH_2$, $CH_3$ or $CH_2CH_3$; $X'{=}CH_3$ or $CH_2CH_3$; $Y{=}NH_2$, $NHCH_3$, $N(CH_3)_2$, 1-pyrrolidino or 1-piperidino; and Z=H, $CH_3$ or $CH_2CH_3$; or (3)

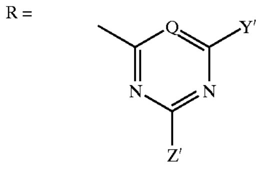

(4)

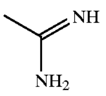

(5)

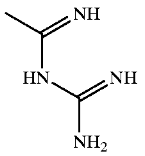

(6)

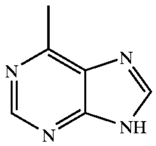

wherein Y' and Z', independently, =H, $NH_2$, $NHCH_3$, $N(CH_3)_2$ or $N^+(CH_3)_3$, 1-pyrrolidino or 1-piperidino; Q is N or CH; and salts thereof.

In yet another embodiment of the invention, the compounds of the invention are compounds formed according to formula (I), wherein J is not R; L is not —NH—; and wherein (1)

R =

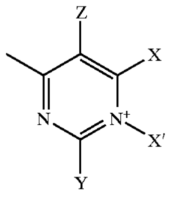

(2)

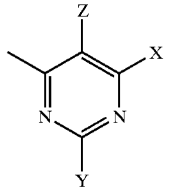

and wherein, independently, X═$NH_2$, $CH_3$ or $CH_2CH_3$; X'═$CH_3$ or $CH_2CH_3$; Y═$NH_2$, $NHCH_3$, $N(CH_3)_2$; and Z=H, $CH_3$ or $CH_2CH_3$; or (3)

R =

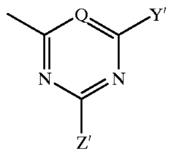

(4)

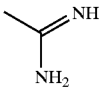

(5)

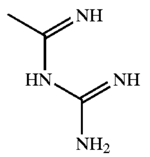

(6)

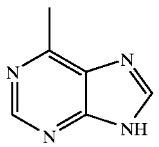

wherein Y' and Z', independently, ═H, $NH_2$, $NHCH_3$, $N(CH_3)_2$ or $N^+(CH_3)$ 3; and salts thereof.

The compounds of the present invention can be synthesized by reacting aniline—to form a compound of formula (II), wherein P is 0—or an acetyl or propanoyl derivative of aniline—to form a compound of formula (II), wherein P is 1—or a diacetyl or dipropanoyl derivative of aniline—to form a compound of formula (II) or formula (III) wherein P is 2—with a chloro derivative of purine, aminomethylpyrimidine, diamino-triazine, or with a cyanoguanidine. The reaction can be performed at 90–100° C. in an aqueous solvent in the presence of a mineral acid to yield the corresponding aminophenyl pyridine or triazine. The pyrimidinium can be synthesized from the pyrimidine by reaction with an excess methyl iodide at 40–45° C. under reflux conditions in 1:1 acetonitrile/tetrahydrofuran or in a 1:1:2 mixture of dichloromethane/acetonitrile/tetrahydrofuran.

For synthesis of aryl bis(diketone) compounds, the acyl groups attached to the benzene ring, for example in 3,5-diacetylaniline, may be converted to 2-oxoacyl groups by reaction with selenium dioxide or selenious acid in wet dioxane or other suitable medium (Rabjohn, N., 1976, Org. React. 24:261–415). Acyl groups attached to benzene rings may be converted to higher-chain 3-oxoacyl groups by treatment with strong base such as sodium hydride or sodium metal in the presence of an aliphatic ester such as ethyl acetate, when the acyl groups are of the structure X—$CH_2$—CO— (March, J., 1992, Advanced Organic Chemistry, 4th ed., Wiley Interscience, New York, pp491–493; Fenton, D. E. et al., 1980, Inorg. Chim. Acta 44:L105-L106)

Any chemistries for generating chemical libraries known in the art can be used to form the J group in the compound of formula (I), including but not limited to combinatorial chemistries, in which interchangeable chemical building blocks are systematically assembled to provide diverse structures. See generally Gordon, E. M. et al., 1994, J. Med. Chem. 37:1385; Chen, C. et al., 1994, J. Amer. Chem. Soc. 116:2661; Cho, C. Y. et al., 1993, Science 261:1303. The modification and adaptation of the various chemistries for generating diversities for the formation of the J group in the compound of formula (I) will be apparent to persons of skill in the art. Moreover, automated synthesis systems can be used to generate the desired chemical diversities including, for example, workstations and robots made by Takeda Chemical Industries Ltd, Osaka, Japan; Zymark Corporation, Hopkinton, Mass.; and Hewlett Packard, Palo Alto, Calif.

5.2 The Inhibition of HIV-1 Importation into the Nucleus of Non-Dividing Cells A quantitative measurement of the activity of the compounds of the invention to block the replication of HIV-1 in non-dividing cells can be determined by culture of a macrophage-tropic strain of HIV-1 on peripheral blood-derived macrophages. The cells are cultured for 5–6 days prior to infection in a medium consisting of DMEM supplemented with 10% type A/B human serum and 200 U/ml Macrophage Colony Stimulating Factor, with half the medium changed after 3 days, to reach a density of about $10^6$ cells per 5 ml well. A macrophage-tropic viral stock may be grown on these cells. The concentration of infectious particles in the stock is estimated by measurement of p24 antigen concentration. To test the effect of compounds of the invention on HIV-1 infection in the above-described culture system, the medium is removed and replaced with medium containing HIV-1 at a concentration of 1 ng of p24 ($10^4$ $TCID_{50}$/ml (TCID=tissue culture infectious doses)) and a known concentration of the compound of the invention (the inhibitor). After 24 hours, the cultures are washed to remove non-adherent virus and the culture is re-fed with medium containing the inhibitor at the desired concentration. The amount of replication of HIV-1 is estimated by an assay of the reverse transcriptase activity or by an assay of the concentration of p24 antigen in the culture medium every 2–3 days throughout the post-infection period. In a preferred embodiment the anti-HIV potency of the candidate drug is measured by comparison of the concentration of reverse transcriptase (RT) or of p24 antigen in the medium of the treated and control cultures at the time of the peak of these values in non-treated control cultures, that is about day 5 or 6 post-infection. Repetition at various levels of inhibitor allows for the calculation of the concentration of inhibitor that achieves 50% inhibition of viral growth, $IC_{50}$. Table I discloses the $IC_{50}$ of various inhibitors.

TABLE I

| Compound | $IC_{50}$ |
|---|---|
| 2-amino-4-(3,5-diacetylphenyl)amino-1,6-dimethylpyrimidinium iodide (Compound No. 2) | 1 nM |
| 2-amino-4-(3-acetylphenyl)amino-1,6-dimethylpyrimidinium iodide (Compound No. 14) | 10 nM |
| 2-amino-4-(3,5-diacetylphenyl)amino-6-methylpyrimidine (Compound No. 11) | 50 nM |
| 4-(3-acetylphenyl)amino-2-amino-6-methylpyrimidine (Compound No. 15) | 15 nM |

Alternatively, the compounds may all be compared for inhibition of HIV replication at a fixed concentration. Presented in Table II are compounds that were used at a concentration of 100 nM to inhibit the production of HIV-1 in cultured monocytes infected with HIV-1 10 days prior to assay (10 ng of p24/$10^6$ cells). The production of HIV-1 in each treated culture is reported as percentage of untreated control.

TABLE II

| Compound | Viral Production |
|---|---|
| N-(3,5-diacetylphenyl)biguanide hydrochloride (Compound No. 12) | 12% |
| 2-(3,5-diacetylphenyl)amino-4,6-diamino-1,3,5-triazine (Compound No. 13) | 14% |
| 4-(3-acetylphenyl)amino-2-amino-6-methylpyrimidine (Compound No. 17) | 20% |
| 3,5-diacetylaniline | 20% |
| N,N-dimethyl-3,5-diacetylaniline | 25% |
| 2,6-diacetylaniline | 28% |
| 3,5-diacetylpyridine | 58% |

FIG. 2A presents further results of the use of the most active of the compounds of Table I, Compound No. 2, to block the replication of HIV-1 in purified monocytes, cultured in medium supplemented with monocyte-colony stimulating factor (M-CSF). The cultures were treated with none or between $10^{-12}$ and $10^{-6}$ M Compound No. 2 and, simultaneously with the beginning of treatment, the cells were exposed to the monocyte-tropic strain HIV-$1_{ADA}$ at about 0.01 $TCID_{50}$/cell (1 ng p24/$10^6$ cells) for 2 hours. Samples were withdrawn at days 3, 6, 10, 14 and 17 after infection and assayed for reverse transcription activity. Compound No. 2 does not inhibit reverse transcriptase, data not shown. The results show that under these conditions the $IC_{50}$ concentrations is between 0.1 and 1.0 nM and that a concentration of between 0.1 $\mu$M and 1.0 $\mu$M completely inhibits the replication of the virus.

FIGS. 2B and 2C show the effects of various concentrations of Compound No. 2 on the production of HIV-1 in monocyte cultures not supplemented with M-CSF. In these studies MOI, as determined by concentration of p24 antigen was; FIG. 2B (8 ng/$10^6$ cells) and FIG. 2C (0.8 ng/$10^6$ cells). These experiments showed $IC_{50}$s of about 10 nM and of less than 1.0 nM respectively.

The inhibition of the replication of HIV-1 is not due to general cytotoxic effects of the compound. Concentrations of Compound No. 2 as high as 10 $\mu$M were without toxic effects on the monocyte cultures as determined by lactate dehydrogenase release and trypan blue exclusion. Further evidence of the specificity of the inhibition due to Compound No. 2 is provided by the data presented in FIGS. 3A and 3B wherein mitogen-stimulated peripheral blood leukocytes were cultured in IL-2-supplemented medium and were exposed to the HIV-$1_{ADA}$ at p24 concentrations of 10 and 1 ng/$10^6$ cells, respectively. In this experiment up to 10 $\mu$M Compound No. 2 had only a marginal effect on viral production at the higher MOI. At the lower MOI, 1 and 10 $\mu$M of Compound No. 2 caused an approximate 2-fold reduction in viral output.

The inhibition of HIV-1 importation into the nucleus of non-dividing cells can also be directly measured. One suitable method to determine directly the activity of compounds of the invention utilizes a cell line that is susceptible to HIV-1 infection, e.g., MT-4 cells, that is growth arrested by treatment with aphidicolin and exposed to HIV-1. PCR amplification is used to detect double-stranded closed circular HIV-1 genomes, which are formed only after nuclear importation, by selecting primers that bridge the junction point of the genome. For greater detail see Bukrinsky, M. I., et al., 1992, Proc. Natl. Acad. Sci. 89:6580–84.

5.3 The Treatment of HIV Infection

The present invention provides a method of treatment of HIV-1 infection by administering to an HIV-1-infected subject a pharmaceutical composition having, as an active ingredient, an effective amount of a compound of formula (I) and (III), and particularly a compound of formula (III). In one embodiment the compound to be administered is Compound No. 2. Pharmaceutical compositions suitable for oral, intraperitoneal, and intravenous administration can be used in the practice of the invention. Such pharmaceutical compositions include, by way of non-limiting examples, aqueous solutions of the chloride, bicarbonate, phosphate and acetate salts of Compound No. 2 and pH-buffered mixtures thereof. The chloride salt of compound 2 is herein referred to as CNI-0294. Compound 11, Compound 14 and Compound 15 are also known as CNI-1194, CNI-H1494 and CNI-1594, respectively.

The effective dose of the active ingredient can be determined by methods well known to those skilled in medicinal chemistry and pharmacology. An effective dose is the dose that achieves in the subject's plasma a concentration of the active ingredient that is sufficient to inhibit the replication of HIV-1 in monocyte cultures as described in Section 5.4, supra, but does not lead to cytopathic effects in such cultures.

The daily dose and dosing schedule to be given a subject can be determined by those skilled in the art, using the pharmacokinetic constants set forth in Table III below, to achieve a target plasma concentration. The target plasma concentration can be selected by routine pharmacological and clinical investigation methods well-known to those skilled in the art, and can be based on a range of concentrations which encompass the $IC_{50}$ calculated for each particular compound. For example, the dose can be adjusted to achieve a range of target plasma concentrations that included the $IC_{50}$ for the compounds as shown in Table I above.

TABLE III

Pharmacokinetic parameters of the CNI compounds.

| | CNI-0294 | CNI-0294 | CNI-0294 | CNI-1194 | CNI-1194 | CNI-1594 | CNI-1894 |
|---|---|---|---|---|---|---|---|
| Route of Injection | i.p. | i.p. | oral | i.p. | oral | i.p. | i.p. |
| Dose (mg/kg) | 50 | 50 | 50 | 50 | 50 | 20 | 50 |
| Vehicle | DP* | W* | DP | W | W | W | W |
| AUC ($\mu$ * hr/ml) | 9.15 | 8.83 | 0.56 | 3.93 | 0.57 | 0.82 | 20.20 |
| $C_{max}$ ($\mu$g/ml) | 18.76 | 18.93 | 0.41 | 5.70 | 0.35 | 1.93 | 13.43 |
| $t_{max}$ (min) | 5 | 5 | 60 | 15 | 15 | 15 | 5 |
| $\alpha$ ($hr^{-1}$) | 1.12 | 1.74 | — | 1.83 | — | 2.14 | 1.19 |
| $\beta$ ($hr^{-1}$) | 0.15 | 0.19 | — | 0.19 | — | 0.04 | 0.03 |
| A ($\mu$g/ml) | 14.00 | 16.07 | — | 5.22 | — | 1.10 | 14.93 |
| B ($\mu$g/ml) | 0.07 | 0.05 | — | 0.14 | — | 0.01 | 0.15 |
| $t_{1/2\alpha}$ (hr) | 0.62 | 0.40 | — | 0.38 | — | 0.32 | 0.58 |
| $t_{1/2\beta}$ (hr) | 4.62 | 3.65 | — | 3.65 | — | 17.33 | 23.10 |
| $V_D$ (L) | 14.14 | 19.80 | — | 5.21 | — | 39.60 | 6.60 |
| $Cl_{tot}$ (ml/min) | 35.35 | 62.70 | — | 16.50 | — | 26.40 | 3.30 |
| Bioavailability | — | — | 0.06 | — | 0.15 | — | — |

*DP = DMSO/peanut oil, W = water

For example, using the foregoing pharmacokinetic constants, particularly, the clearance rate, the daily dose and dosing schedule needed to obtain a given target average plasma concentration can be calculated. The results of such calculations for Compound Nos. 2, 11 and 15 are presented in Table IV. The calculated doses of Compound Nos. 2 and 15 are considerably below the toxic levels, as measured by the $LD_{50}$, of these compounds. See, Section 6.4 below.

TABLE IV

| Compound No. | M.W. | Target serum conc. | Clearance‡ (ml/min) | Dose (mg/Kg day) |
|---|---|---|---|---|
| 2* | 334 | 10 nM | 35.35 | 6.80 |
| 11 | 280 | 50 nM | 16.50 | 13.3 |
| 15 | 250 | 15 nM | 26.40 | 5.70 |

‡measured in a 25 gr mouse
*Chloride salt (CNI-0294)

Using such methods, a dose can be calculated to achieve a predetermined target plasma concentration. A practicable target plasma concentration of Compound No. 2 ranges from 0.5 nM to 10 nM; for Compound No. 11, a practicable target range is from 25 nM to 100 nM; for Compound No. 15, a practicable target range is from 7.5 nM to 50 nM.

Subjects who can benefit from the administration of the compounds of the invention according to this method include all persons infected by HIV-1. More particularly, firstly, those who benefit include those subjects who have or are at risk to develop CNS signs of HIV-1 infection and/or subjects that have developed significant weight loss. Secondly, those who benefit include those who have been recently exposed to HIV-1, but who do not yet have an established chronic infection.

5.4 Pharmaceutical Formulations

Because of their pharmacological properties, the compounds of the present invention can be used especially as agents to treat patients suffering from HIV and can be used as agents to treat patients suffering from other viral infections or chronic diseases that are dependent upon nuclear localization as part of the pathogenic process. The compounds of the invention can also be used to treat or prevent other infectious diseases such as parasitic diseases, and in particular malaria. Such a compound can be administered to a patient either by itself, or in pharmaceutical compositions where it is mixed with suitable carriers or excipient(s).

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well-known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

5.5 Use of the Compounds of the Invention to Derivatize Proteins

The compounds of the present invention of formula (III), wherein P is 1 or 2, can be used to derivatize a target protein and thereby determine the presence of adjacent $N^{\epsilon}$-moieties. The test reaction can be conducted in aqueous buffer at mild to moderate alkaline pH, between about 7.2 and 8.0. Specific derivatization of the target protein can be detected by any means that separates protein-bound and free derivatizing compound. The derivatizing compound optionally can be detected by radiolabeling it. In one embodiment, the compound can be synthesized using $^{14}C$-methyliodide in place of methyliodide. Alternatively, use can be made of the strong UV absorption or fluorescence of the derivatizing compounds. Compound No. 2, for example has a absorption peak of 16,000 $M^{-1}$ $cm^{-1}$ at $\lambda$=298 nm. In a preferred embodiment the target protein is derivatized by a compound of the invention, irreversibly reduced with sodium borohydride or cyanoborohydride and fragmented into peptides by trypsin or the like. The resultant peptides can be compared with the peptides obtained from an unreacted sample of the protein by analysis using any chromatographic or electrophoretic technique that resolves peptides, e.g., reverse phase High Performance Liquid Chromatography (HPLC). When the peptides are resolved by any high resolution chromatography procedure, the derivatized peptides can be readily detected by their altered elution time and the absorbance at $\lambda$=298 nm.

In a preferred embodiment the practitioner will conduct the reaction at various pH points to determine whether a positive result can be obtained at any point within the expected range. A positive result, i.e., a result that indicates the presence of adjacent $N^{\epsilon}$-moieties, is one in which a large fraction of each of a limited number, i.e., between 1–4, of peptides of the target protein are derivatized and negligible amounts of other peptides are affected.

The above-described protein derivatization technique can be used to determine whether a candidate compound can be used, according to the invention to prevent productive HIV-1 infection of macrophages. A comparison of the activity of a candidate compound and that of Compound No. 2 as derivatizing agents specific for nuclear localization sequences can be made. A compound that derivatizes the same peptides to the same extent as Compound No. 2 can be used to practice the invention.

5.6 The Treatment of Infectious Diseases

The compounds of the present invention can be used to prevent or treat infectious diseases in animals, including mammals and preferably humans, and these compounds are particularly suited to treatment of parasitic diseases, more particularly, malaria. The invention described herein provides methods for treatment of infection, including and without limitation, infection with parasites, and methods of preventing diseases associated with such infection. The compounds can reduce parasitemia when administered to an animal infected with a parasite.

Infectious diseases may include without limitation: protozoal diseases such as those caused by Kinetoplastida such as *Trypanosoma* and *Leishmania*, by Diplomonadina such as *Giardia,* by Trichomonadida such as *Dientamoeba* and *Trichomonas,* by Gymnamoebia such as *Naegleria* and the Amoebida such as *Entamoeba* and *Acanthamoeba,* by Sporozoasida such as *Babesia* and the Coccidiasina such as *Isospora, Toxoplasma, Cryptosporidium, Eimeria, Thelleria,* and *Plasmodium;* metazoal diseases such as those caused by the Nematoda (roundworms) such as *Ascaris, Toxocara,* the hookworms, *Strongyloides,* the whipworms, the pinworms, *Dracunculus, Trichinella,* and the filarial worms, and by the Platyhelminthes (flatworms) such as the Trematoda such as *Schistosoma,* the blood flukes, liver flukes, intestinal flukes, and lung flukes, and the Cestoda such as the tapeworms; viral and chlamydial diseases including for instance those caused by the Poxyiridae, Iridoviridae, Herpesviridae, Adenoviridae, Papovaviridae, Hepadnaviridae, Parvoviridae, Reoviridae, Birnaviridae, Togaviridae, Coronaviridae, Paramyxoviridae, Rhabdoviridae, Filoviridae, Orthomyxoviridae, Bunyaviridae, Arenaviridae, Retroviridae, Picornaviridae, Calciviridae and by *Chlamydia;* bacterial diseases; mycobacterial diseases; spirochetal diseases; rickettsial diseases; and fungal diseases.

In one embodiment, the compounds of the invention having anti-infective activity are formed according to formula (I), (II) and (III) as described in section 5.1.

In another embodiment, the compounds of the invention may be used therapeutically against infections with *Plasmodium* species such as *P. falciparum, P. vivax, P. ovale* and *P. malariae*, that cause acute and recurrent malaria in humans. The compounds of the invention are also active against infection by other *Plasmodium* species, which include *P. berghei, P. knowlesi, P. simium, P. cynomolgi bastianelli* and *P. brasilianum.*

In yet another embodiment of the invention, the compounds may be useful in providing chemoprophylaxis for individuals at risk of infection, such as when travelling in endemic areas. By maintaining in circulation an effective concentration of a compound of the invention, malaria can be prevented by suppressing the pathological stages of infection with *Plasmodium* species. Without being bound by any theory, the compounds of the invention can be effective against various stages of the life cycle of the parasite, including sporozoites and merozoites, as well as dormant, asexual and sexual stages. The compounds of the invention may be active in the blood stream, in erythrocytes, in the liver, or in other tissues where the malaria parasite may reside.

In a specific embodiment of the invention, the compound of the invention can be used to prevent malaria, or to treat malaria, or to treat infection with *Plasmodium* species that are resistant to antimalarial drugs, such as, but not limited to, chloroquine and pyrimethamine. The antimalarial properties of the compounds are not diminished against *P. falciparum* known to be resistant to chloroquine or pyrimethamine (see section 8 infra). Although not wishing to be bound by any theory of mechanism of the compounds, it is contemplated that the compounds interact with biochemical targets that are different and independent from those affected by these two classic antimalarial drugs. Thus, the compounds of the invention may be used preferentially to treat malarial infections arising out of areas that are known or suspected to harbor drug-resistant *Plasmodium* species.

In a further embodiment, the compounds may contain a single acyl group, i.e., P=1, on the arylene ring or the acyl group can be absent therefrom, i.e., P=0, and/or the heterocyclic substituent, i.e., R, can be uncharged. In the embodiment of the invention wherein there are two acyl groups, i.e., P=2, on the arylene ring, it is preferred that such acyl groups are not in an ortho arrangement relative to each other. In another preferred embodiment of the invention, the compounds that possess potent antimalarial activity are arylene bis(methylketone) compounds that contain a charged heterocylic ring such as a pyrimidinium, as in CNI-0294 (see FIG. 4A).

The antimalarial properties of the compounds of the invention can be analyzed by techniques, assays and experimental animal models well known in the art. For example, the inhibition of growth of *Plasmodium falciparum* in vitro by the compounds may be assessed by the hypoxanthine-incorporation method (Desjardins et al., 1979, Antimicrob. Ag. Chemother. 16:710–718). The in vitro antiparasitic activities of several exemplary compounds of the invention were assessed by this method, and the results are described in Section 8. The in vivo efficacy of the compounds can also be tested in mouse models in which parasitemia is enumerated following administration of the compound (Ager, A. L. 1984, Rodent malaria models, pp 225–264. In Handbook of Experimental Pharmacology vol. 68, Antimalarial Drugs, Peters and Richards eds, Springer-Verlag, Berlin). The in vivo activity of several exemplary compounds have been evaluated in a four-day suppression model in mouse, and the results are provided in Section 8.

The present invention also provides pharmaceutical compositions. Such pharmaceutical compositions comprises a prophylactically or therapeutically effective amount of the compound and a pharmaceutical carrier, such as those described in section 5.4. More specifically, an effective amount means an amount effective to prevent development of or to alleviate the existing symptoms of the subject being treated. Determination of the effective amounts is well within the capability of those skilled in the art, especially in light of the detailed disclosure provided herein. For any compound used in the method of the invention, the effective dose can be estimated initially from in vitro assays. A dose can be formulated in animal models to achieve a circulating range that includes the $IC_{50}$ (i.e., the concentration of compound which achieves a half-maximal inhibition of growth of parasite) as determined in the in vitro assay. Such information can be used to more accurately determine useful doses in subjects, for example, humans. The dosage may vary within this range depending upon the dosage form employed and the route of administration. Various delivery systems are known and can be used for administration of the compound, e.g., encapsulation in liposomes. Other methods of administration include but are not limited to intradermal, intramuscular, intraperitoneal, intravenous, subcutaneous, intranasal and oral routes.

In another embodiment, the invention provides a method of preventing or treating malaria by administering to a subject in need thereof an effective amount of a compound of the invention. In a further aspect there is provided a method of preventing or treating malaria, especially malaria caused by drug resistant *Plasmodium* species in humans, which method comprise administering to the individual in need thereof an effective amount of a compound of the present invention and an effective amount of an antimalarial drug. The invention also provides the use of a compound of the invention and an antimalarial drug in the manufacture of a medicament for the prevention or treatment of malaria. Such antimalarial drugs may include but are not limited to quinine, aminoquinolines (chloroquine and primaquine), pyrimethamine, mefloquine, halofantrine, and artemisinins.

The "adjunct administration" of a compound of the invention and an antimalarial drug means that the two are administered either as a mixture or sequentially. When administered sequentially, the compound may be administered before or after the antimalarial drug, so long as the first administered agent is still providing antimalarial activity in the animal when the second agent is administered. Any of the above-described modes of administration may be used in combination to deliver the compound and the antimalarial drug.

The present invention is to be understood as embracing all such regimens and the term "adjunct administration" is to be interpreted accordingly. When a compound of the invention and an antimalarial drug are administered adjunctively as a mixture, they are preferably given in the form of a pharmaceutical composition comprising both agents. Thus, in a further embodiment of the invention, it is provided a pharmaceutical composition comprising a compound of the invention and an antimalarial drug, together with a pharmaceutically acceptable carrier.

5.7 Compounds and Assays for Compounds That Target Specific NLS

The present invention also provides methods of use of the alkyl aryl carbonyl compounds as described in section 5.1. The reactive group(s) of the compounds of the invention are capable of forming stable but reversible covalent interactions with the side chain of basic amino acid residue(s) of a protein. In certain embodiments of the invention, the divalency of the compound ensures that the compound will form especially stable associations with sequences, such as nuclear localization signals (NLS), that comprise multiple basic amino acid residues, such as lysines and arginines. Nuclear localization signals, in general, and the HIV matrix antigen (MA) p17 NLS in particular are characterized by a stretch of basic, and often positively charged, amino acids typically including one or more lysines. Such NLS-containing proteins are often associated with other molecules in a complex.

The interaction of basic side chain(s) with the reactive carbonyl group(s) of the compound is facilitated by the prior interaction of the targetting group of the compound with a specific docking site, said docking site being positioned proximately to the side chain of the basic amino acid residue(s) in the target NLS. The docking site may be located on the NLS-containing protein or another molecule in a complex comprising the NLS-containing protein. As a result of the formation of stable but reversible covalent interactions with the compound, the NLS-containing protein or the molecular complex comprising NLS-containing protein is prevented from interacting with cellular receptors for the NLS. The protein or molecular complex is thus blocked from importation into the nucleus.

Although the carbonyl group(s) of the compounds of the invention can react with alternative susceptible side chains in a protein, the interaction between the targetting group and the docking site confers specificity to the activity of the carbonyl group(s), such that the carbonyl group(s) react only with particular target basic amino acid residues in a protein. The specific recognition and binding of the compound to a docking site determines which basic amino acid residue(s) in a protein will become inactivated by the carbonyl group(s) of the compound. Because of the proximity of the basic residues in the target NLS to the docking site, the interaction of the compound with the docking site localizes the compound to the vicinity of the target NLS, thereby facilitating the reaction of the carbonyl group(s) of the compound with the target NLS. It is to be understood that the docking site can be on the NLS-containing protein or another molecule in a complex comprising the NLS-containing protein. Thus, in one embodiment, the compounds of the invention can be used to target a specific nuclear localization signal, thereby blocking importation of specific proteins or molecular complexes into the nucleus.

As demonstrated by the experiments in section 9, the compounds of the invention, particularly Compound No. 2 or CNI-H0294, are capable of inhibiting nuclear translocation of HIV-1 pre-integration complexes. The inhibitory effect is caused by the inactivation of the NLS of HIV MA in a reaction that requires the presence of HIV reverse transcriptase (RT), i.e. the target nucleoprotein complex. The carbonyl groups of Compound No. 2 or CNI-H0294 react with the NLS of MA by formation of Schiff base adducts, and prevent the binding of MA to karyopherin α, the cellular receptor for NLS, and that blocks translocation of proteins into the nucleus. The inventors further showed that the interaction between Compound No. 2 or CNI-H0294 via its pyrimidine moiety with RT that contains a docking site determines the specificity of the compound towards HIV pre-integration complex, and its low cytotoxicity to the host cell. Thus, the alkyl aryl carbonyl compounds of the invention can be used for targeted inactivation of NLS in a protein or a molecular complex, such as the HIV-1 or other viral pre-integration complex, comprising contacting the protein or molecular complex with a compound of the invention. Furthermore, variations and modifications of the targetting group provides for altered binding specificities, and can serve to target the alkyl aryl carbonyl compound to a different NLS-containing protein or molecular complex. Thus, it is envisioned that the alkyl aryl carbonyl compounds of the invention, can be selected to inactivate specifically various different NLS-containing proteins or molecular complexes.

Accordingly, it is contemplated that a molecular complex comprises at least one NLS-containing protein and can include other proteins, nucleic acids, carbohydrates, lipids and other biological molecules. The docking site to which the targeting group of the compound binds may reside on any molecule in the molecular complex. In a preferred embodiment, the target of the compound of the present invention is a viral nucleoprotein complex or a viral protein. Alternatively, a target may be a cellular protein such as a transcription factor. An exemplary, non-limiting list of such targets may include, viruses which translocate both viral proteins and nucleic acids into the infected cell nucleus, such as human immunodeficiency virus and other retroviruses, influenza virus, hepatitis B and hepatitis delta virus, papillomaviruses and parvoviruses; viruses which translocate only viral protein into the infected cell nucleus such as adenoviruses, measles and other paramyxoviruses, herpes viruses, and rabies and other bunyaviruses; and single protein, such as NF-KB and other transcription factors.

In another embodiment of the invention, screening assays are provided for identification of alkyl aryl carbonyl compounds of the invention that can inactivate the NLS of a specific NLS-containing protein or NLS-containing molecular complex. The assays of the invention involves monitoring the binding of the NLS-containing protein or molecular complexes to at least one protein or fragment thereof that interacts with the NLS in the course of nuclear translocation, i.e., the cellular receptor, in the presence of an alkyl aryl carbonyl test compound of the present invention, and a comparison of such binding in the absence of the test compound. It is anticipated that the desired compound binds specifically to a docking site in the NLS-containing protein or molecular complex, and inactivates the NLS. As a result, the binding of the NLS protein or molecular complex to the cellular receptor is reduced or abolished.

Any cellular protein(s) that interact with the NLS, and functionally effect or contribute to the nuclear translocation of the NLS-containing protein or complex can be used in the assays of the invention. Fragments of such cellular proteins that bind NLS can also be used in the assays of the invention. Such cellular proteins and fragments thereof, collectively referred herein to as the cellular receptor moiety, may include but are not limited to, karyopherin αβ heterodimer and fragments thereof, or fusion proteins, such as karyopherin α-glutathione S-transferase (GST-karyopherin α).

The assays are performed in vitro in which the cellular receptor moiety is immobilized directly or indirectly onto a solid support. The NLS-containing protein or molecular complex, purified or in a cell extract, is contacted with the immobilized cellular receptor moiety in the presence of test compound. As a control, the NLS-containing protein or molecular complex is contacted with the immobilized cellular receptor moiety under the same condition, but in the absence of the test compound. After an interval sufficient for binding reactions to occur among the components in the assay, the solid support is washed to remove any unbound molecules. A detection procedure is performed with the solid support to quantify the binding of NLS-containing protein or molecular complex to the immobilized cellular receptor moiety as compared to binding reactions in the absence of test compound. The absence of bound NLS-containing protein or molecular complex, or a reduction in the binding of the NLS-containing protein or molecular complex to the solid support, in the presence of a test compound, indicates that the test compound can be useful in inhibiting the importation of the specific NLS-containing protein or molecular complex into the nucleus.

The detection procedure may employ an antibody or a ligand that recognizes and binds the NLS-containing protein or a component of the molecular complex. Alternatively, if the molecular complex comprises nucleic acids, such as the case of HIV-1 pre-integration complex, polymerase chain reaction may be employed to detect the presence of specific nucleic acid sequences on the solid support. Any appropriate isotopic and nonisotopic labels can be used in conjunction with the detection procedure. Detection or measurement of the antibody, ligand or amplified nucleic acids is accomplished by standard techniques well known in the art. Those skilled in the art will be able to determine operative and optimal conditions for the above-described techniques by employing routine experimentation.

For example, a screening assay for alkyl aryl carbonyl compounds that inactivate the NLS of HIV matrix antigen can be set up as follows. A glutathione S-transferase-karyopherin α fusion protein (GST-karyopherin α) that binds NLS is used as the cellular receptor moiety. The fusion-protein is immobilized onto glutathione Sepharose (Pharmacia) by incubation for 30–60 minutes at room temperature. Cytoplasmic extracts from cells that have been infected by HIV may be prepared by mechanically lysing infected cells in the presence of protease inhibitors, and removing the nuclei by centrifugation.

Alternatively, HIV MA and RT, and possibly other accessory proteins, such as Vpr, that are present in the pre-integration complex can be produced by recombinant DNA methods, and reconstituted in vitro into a complex for use in the assay. The cytoplasmic extract or the reconstituted MA/RT complex is incubated at room temperature with the GST-karyopherin α Sepharose beads in the presence of various concentrations of compounds of the invention, for an interval sufficient for binding interactions to occur, for example, 30 minutes. At the end of the incubation, the beads are washed to remove any unbound material. To quantitate the binding of pre-integration complex to the beads, HIV-1 DNA was isolated from the beads by SDS-proteinase K treatment with subsequent phenol-chloroform extraction, and analyzed by polymerase chain reaction using primers specific for the pol gene, as described in Bukrinsky, M. I., et al., 1995, J. Exp. Med. 181:735–745. Alternatively, the amount of MA or RT bound to the beads can be determined by an immunoassay using anti-MA or anti-RT sera. Compounds of the invention that can be used to block nuclear importation of HIV are indicated by a reduction or inhibition of binding to the beads by the HIV-1 pre-integration complex or reconstituted MA/RT complex as compared to the control.

6 EXAMPLES

6.1 Synthesis of Specific Compounds

Compound No. 2, FIG. 1A: A suspension of Compound No. 11 (2-amino-4-(3,5-diacetylphenyl)amino-6-methylpyrimidine) (0.284 g), was suspended in 1:1 acetonitrile-tetrahydrofuran was treated with methyl iodide (2 mL) and heated at 40–45° C. under a reflux condenser for 18 hr. Cooling and filtration gave 0.35 g of 2-amino-4-(3,5-diacetylphenyl)amino-1,6-dimethylpyrimidinium iodide, mp 292° C.

2-Amino-4-(3,5-diacetylphenyl)imino-1,4-dihydro-1,6-dimethylpyrimidine. A suspension of 21 g (49.3 mmole) of 2-amino-4-(3,5-diacetylphenyl)amino-1,6-dimethylpyrimidinium iodide (compound No. 2, synthesized as described in section 6.1) in 1:1 methanol/water (750 mL) at 60° C. was treated with excess 2N NaOH with cooling to maintain about 60° C. An additional 200 mL of water was added and the mixture was cooled in ice and filtered to give 14.69 g 2-amino-4-(3,5-diacetylphenyl)imino-1,4-dihydro-1,6-dimethylpyrimidine as yellow crystals, mp 219–220°.

2-Amino-4-(3,5-diacetylphenyl)amino-1,6-dimethylpyrimidinium chloride (CNI-0294). CNI-0294 is the chloride salt of compound No. 2. The base 2-amino-4-(3,5-diacetylphenyl)imino-1,4-dihydro-1,6-dimethylpyrimidine (14.35 g, 48 mmole) was dissolved in 500 mL of methanol and treated with HCl gas until precipitation appeared complete. Filtration gave 12.8 g of white crystals with a faint yellowish tinge, mp 306.5–307.5°.

Compound No. 11 (CNI-1194): A suspension of 3,5-diacetylaniline (0.885 g) in water (18 mL) was treated with 2-amino-4-chloro-6-methylpyrimidine (0.718 g) and concentrated HCl (0.42 mL) and heated at 90–100° C. for 30 min. After cooling the mixture was treated with 10 mL of aqueous 1N KOH. The mixture was stirred for 10 min and the solid was filtered out, washed with water, and dried, to give 1.332 g of tan crystals. Recrystallization from ethyl acetate-2-methoxyethanol gave 1.175 g of 2-amino-4-(3,5-diacetyl-phenyl)amino-6-methylpyrimidine as light buff crystals, mp 240–241° C.

Compound No. 12. A suspension of 3,5-diacetylaniline (0.531 g) in water (8 mL) was treated with cyanoguanidine (0.285 g) and conc. HCl (0.25 mL) and heated at reflux. After 6 hr the mixture was cooled and concentrated and 0.248 g of off-white solid was filtered out and dried to give N-(3,5-diacetylphenyl)biguanide hydrochloride, mp 260–70° C. (dec).

Compound No. 13: A suspension of 3,5-diacetylaniline (1.95 g) in water (10 mL) was treated with 2-chloro-4,6-diamino-1,3,5-triazine (1.455 g) and concentrated HCl (0.1 mL) and heated at reflux for 20 min. After cooling the hydrochloride of Compound No. 13 separated as a white powder. This was filtered out, dissolved in 60 mL of boiling aqueous 75% methanol and treated with triethylamine (1.5 mL). On cooling, off-white flakes separated. Filtration and drying gave 1.79 g of 2-(3,5-diacetylphenyl)amino-4,6-diamino-1,3,5-triazine, mp 271–2° C.

Compound No. 14 (CNI-H1494): 4-(3-acetylphenyl)amino-2-amino-6-methylpyrimidine, Compound No. 15, (0.968 g) was suspended in acetone (5 mL) containing methyl iodide (2 mL) was heated at reflux for 48 hr. Filtration after cooling gave 0.657 g of 4-(3-acetylphenyl)amino-2-amino-1,6-dimethylpyrimidinium iodide as a white powder, mp 238–40° C.

Compound No. 15 (CNI-1594): A suspension of m-aminoacetophenone (2.7 g) and 2-amino-4-chloro-6-methyl-pyrimidine (2.87 g) in 40 mL water was treated with 1.7 mL concentrated HCl and heated at reflux for 1 hour. Addition of 40 mL 1N KOH gave a light buff solid, which was filtered out and dried to give 3.8 g 4-(3-acetylphenyl)amino-2-amino-6-methylpyrimidine, mp 196–98° C.

Compound No. 16: A suspension of 3,5-diacetylaniline (0.531 g) in water (10 mL) was treated with 6-chloropurine (0.464 g) and concentrated HCl (0.25 mL) and heated at reflux for 30 min. After cooling the mixture was treated with 6 mL of aqueous 1N KOH. The mixture was stirred for 10 min and the solid was filtered out, washed with water, and dried, to give 0.80 g of 6-[(3,5-diacetylphenyl)amino]purine, mp dec 340–350° C.

Compound No. 17 (CNI-1794): A suspension of p-aminoacetophenone (1.35 g) and 2-amino-4-chloro-6-methyl-pyrimidine (1.435 g) in 20 mL water was treated with 0.85 mL conc HCl and heated at reflux for 1 hr. Addition of 20 mL 1N KOH gave a light buff solid, which was filtered out and dried to give 2.28 g 4-(3-acetylphenyl)amino-2-amino-6-methylpyrimidine, mp 194–196° C. Of this, 1.21 g was treated with methyl iodide (3 mL) in dimethylformamide (15 mL) at room temperature for 42 hr. Dilution with ethyl acetate and filtration gave 1.11 g 4-(4,acetylphenyl)amino-2-amino-1,6-dimethylpyrimidinium iodide as a white powder, mp 302–3° C.

Compound No. 45. (CNI-4594) A mixture of aniline (0.93 g) and 2-amino-4-chloro-6-methylpyrimidine (1.44 g) in 36 mL water was treated with 0.84 mL conc HCl and heated at reflux for 1 hr. Addition of 20 mL 1N KOH gave a light buff solid, which was filtered out, dried, and recrystallized from ethyl acetate/2-methoxyethanol and ethyl acetate/hexane to give 0.69 g 4-phenylamino-2-amino-6-methylpyrimidine, mp 179–180° C.

Compound No. 46. A suspension of 4-phenylamino-2-amino-6-methylpyrimidine, Compound No. 45, (0.25 g) in ethanol (4 mL) was treated with methyl methanesulfonate (0.090 g) and heated at reflux for 5 days. Additional methyl methanesulfonate (0.090 g) was added and the mixture refluxed another 2 days. Concentration and recrystallization from a mixture of methanol, ethyl acetate, and tert-butyl ethyl ether gave 0.10 g of 4-phenylamino-2-amino-1,6-dimethylpyrimidinium methanesulfonate.

3,5-diacetylaniline (CNI-1894) was synthesized as per Ulrich et al. (1983, J Med Chem 27:35–40). Diacetylanilines substituted in other positions can be synthesized according to Ulrich et al. supra or McKinnon et al. (1971, Can J Chem 49:2019–2022). All other starting materials were obtained from the Aldrich Chemical Co. Nuclear magnetic resonance spectra and elemental analysis for all the compounds agreed with expected values.

6.2 The Use of Compound No. 2 to Inhibit HIV Replication in Primary Macrophage Lines

6.2.1 Materials and Methods

Primary human monocytes were obtained from peripheral blood by Ficoll-Hypaque centrifugation and adherence to plastic as described previously. Gartner S. P., et al., 1986, Science 233:215. Briefly, after Ficoll-Hypaque (Pharmacia) separation, PBMCs were washed 4 times with DMEM (the last wash was done at 800 rpm to remove platelets) and resuspended in monocyte culture medium [DMEM supplemented with 1 mM glutamine, 10% heat-inactivated human serum, 1% penicillin+streptomycin mixture (Sigma)] at a density of $6\times10^6$ cells/ml. Cells were seeded in 24-well plates (1 ml per well) and incubated for 2 h at 37° C., 5% $CO_2$. Following incubation, cells were washed 3 times with DMEM to remove non-adherent cells and incubation was continued in monocyte culture medium supplemented with 250 U/ml human M-CSF (Sigma). Cells were allowed to mature for 7 days prior to infection with the monocyte-tropic strain, HIV-$1_{ADA}$. Nuovo, G. J., et al., 1992, Diagn. Mol. Pathol. 1:98. Two hours after infection, cells were washed with medium and cultured in RPMI supplemented with 10% human serum. In experiments where PCR analysis was performed, virus was pretreated with RNAse-free DNAse (Boehinger-Mannheim) for 2 h at room temperature and then filtered though a 0.2 μm pore nitrocellulose filter prior to infection.

PBMCs were purified by Ficoll-Hypaque centrifugation and activated by 10 μg/ml PHA-P (Sigma) and 20 U/ml recombinant human IL-2 (rhIL-2) in RPMI 1640 supplemented with 10% FBS (HyClone). After 24 h incubation, cells were washed and inoculated with HIV-$1_{ADA}$ in RPMI 1640 supplemented with 10% FBS. After a 2 h adsorption, free virus was washed away and cells were cultured in RPMI 1640 supplemented with 10% FBS and 20 U/ml rhIL-2.

Virus stock and infection. Macrophage-tropic strain HIV-$1_{ADA}$ was amplified in primary human monocytes and concentrated to produce stock with $TCID_{50}$ of about $10^5$/ml. The concentration of HIV-1 was determined by immunoassay of viral p24, concentration; using a conversion factor of 1 ng/200 HIV-1 particles.

6.2.2 p24 and RT Assay

For p24 assay, sequential 1:9 dilutions of culture supernatant were prepared and analyzed by ELISA as suggested by the manufacturer (Cellular Products, Buffalo, N.Y.). For the reverse transcriptase (RT) assay, 10 μl of culture supernatant was added to 40 μl of reaction mixture (final composition was 50 mM Tris-HCl, pH 7.8; 20 mM KCl; 5 mM $MgCl_2$; 1 mM DTT; 0.1% Triton X-100; 0.2 OD/ml polyA; 0.2 OD/ml oligo$(dT)_{12-18}$; and 40 μCi/ml $^3$H-dTTP (76 Ci/mmol, DuPont) and incubated 2 hr at 37° C. 5 μl of the reaction mixture was then spotted onto the DE 81 (Whatman) paper. Paper was air dried and washed 5 times with 5% $Na_2HPO_{41}$ followed by rinsing with distilled water. After air drying, paper was put on a Flexi Filter plate (Packard), covered with scintillation fluid and counted in a Top Count Microplate Counter (Packard). Results are expressed as counts per minute in 1 ml of supernatant (cpm/ml).

6.2.3 Results Dividing and Quiescent Cells

The cytotoxicity of Compound No. 2 was tested in monocyte cultures by trypan blue exclusion assay or lactate dehydrogenase (LDH) release. By both assays, no cytotoxic effect was observed with concentrations of the compound up to 10 μM (data not shown). Results presented in FIG. 2 show the effect of various concentrations of Compound 2 on HIV-1 replication in monocytes. From this experiment, we estimate the $IC_{50}$ for this compound between 0.1 and 1 nM. Similar and higher concentrations of the compound were also tested on activated PBLs. The anti-viral effect of this compound was much less expressed in these actively dividing cell populations (FIG. 3) No anti-viral effect was detected when cultures of replicating cells were infected at the multiplicity of infection used to infect monocytes.

6.2.4 AZT and Compound No. 2 in Combination

AZT is a drug that is routinely used to treat HIV-1 infected persons. However, two factors are known to diminish the effectiveness of AZT: its toxicity and the emergence of resistant mutant strains of HIV-1. The effects of both of these factors can be reduced by administering a second, synergistic HIV-1-inhibitory drug with AZT.

In view of these premises, the effects on HIV-1 replication in human monocyte cultures of the various concentrations of AZT, alone or in combination with 100 nM Compound No. 2, were tested using the protocols of Sections 6.2.1 and 6.2.2. Drugs were added to the monocyte cultures together with HIV-1 at about $10^5$ TCID/ml. The concentration of drugs was maintained on refeeding. HIV-1 replication was assessed by assay of the supernatant for reverse transcriptase activity. The results are expressed as mean±std. dev. ($cpm\times10^{-3}$) in Table V.

TABLE V

Effects of Combined AZT/Compound No. 2 on HIV-1 infected Monocyte Cultures

| | day-7 | | day-11 | |
|---|---|---|---|---|
| [AZT] | (−) No. 2 | (+) No. 2 | (−) No. 2 | (+) No. 2 |
| 0 | 1.46 ± 0.43 | 0.37 ± 0.07 | 1.81 ± 0.75 | 0.72 ± 0.30 |
| 10 pM | 0.92 ± 0.21 | 0.15 ± 0.05 | 1.63 ± 0.81 | 0.18 ± 0.06 |
| 100 pM | 0.79 ± 0.14 | 0.13 ± 0.04 | 1.34 ± 0.59 | 0.15 ± 0.06 |
| 1 nM | 0.60 ± 0.28 | 0.04 ± 0.02 | 1.07 ± 0.49 | 0.09 ± 0.03 |
| 10 nM | 0.05 ± 0.02 | 0.03 ± 0.02 | 0.08 ± 0.03 | 0.07 ± 0.03 |

These results demonstrate that there is synergy between the AZT and Compound No. 2. The synergistic effects are most pronounced at the lower doses of AZT on day 11. For example, 10 pM AZT alone produces an about 20% reduction in RT activity on day-11, 100 nM Compound No. 2 alone produces about a 60% reduction. Without synergy, the combination should produce a 70% reduction $(100\times(1-(0.8\times0.4))$. Instead the observed reduction was 90%.

6.3 The Compounds of the Invention Do Not Block the Nuclear Importation of Essential Proteins in Cells +cl 6.3.1 Direct Demonstration of the Inhibition of HIV-1 Nuclear Importation by Compound No. 2

The effects of Compound No. 2 on the nuclear importation of HIV-1 preintegration complexes can be directly measured by detecting the presence of circularized duplex HIV-1 genomic DNA. These duplex circles can be readily detected by PCR amplification using primers which span the junction of the circularized HIV-1 genome. Bukrinsky, M. I., et al., 1992, Proc. Natl. Acad. Sci. 89:6580–84.

Briefly, the efficiency of nuclear translocation was estimated by the ratio between the 2-LTR and pol-specific PCR products, which reflects the portion of 2-LTR circle DNA molecules as a fraction of the entire pool of intracellular HIV-1 DNA. Viral 2-LTR circle DNA is formed exclusively within the nucleus of infected cells and thus is a convenient marker of successful nuclear translocation. Bukrinsky, M. I., 1992, Procd. Natl. Acad. Sci. 89:6580–84; Bukrinsky, M. I., 1993, Nature 365:666–669.

PCR analysis of HIV-1 DNA: Total DNA was extracted from HIV-1-infected cells using the IsoQuick extraction kit (Microprobe Corp., Garden Grove, Calif.). DNA was then analyzed by PCR using primer pairs that amplify the following sequences: a fragment of HIV-1 (LTR/gag) that is the last one to be synthesized during reverse transcription and therefore represents the pool of full-length viral DNA molecules; a fragment of polymerase gene (pol); a 2-LTR junction region found only in HIV-1 2-LTR circle DNA molecules; or a fragment of the cellular a-tubulin gene. Dilutions of 8E5 cells (containing 1 integrated copy of HIV-1 DNA per genome) into CEM cells were used as standards. Amplification products were transferred to nylon membrane filters and hybridized to $^{32}$P-labeled oligonucleotides corresponding to internal sequences specific for each PCR amplification fragment, followed by exposure to Kodak XAR-5 film or a phosphor screen.

Quantitation of PCR Reactions: Bands of correct size revealed after hybridization were quantitated with a PhosphorImager (Molecular Dynamics) by measuring the total density (integrated volume) of rectangles enclosing the corresponding product band. Efficiency of nuclear translocation of HIV-1 DNA was estimated by measurement of the amount of 2-LTR circle DNA ($N_{2\text{-}LTR}$) relative to total viral DNA ($N_{tot}$) in each culture, indexed to the same ratio of appropriate control cultures. Thus, Translocation Index= $(N_{2\text{-}LTR}/N_{tot})$ $(C_{2\text{-}LTR}/C_{tot})\times100$.

Results: Primary human monocytes were infected with $HIV\text{-}1_{ADA}$ in the presence of 100 nM concentration of Compound No. 2 or without drugs (control). Half the medium was changed every 3 days, and drugs were present throughout the whole experiment. Cell samples were taken at 48 and 96 hours post infection and the Translocation Index, relative to the drug free control was determined. At both time points the Translocation Index was less than 10, indicating there was greater than 90% inhibition of nuclear importation.

7 PHARMACOKINETIC AND TOXICOLOGICAL STUDIES

This section describes in detail the techniques that were used to study the toxicological and pharmacological properties of the compounds of the invention.

7.1 Drug Analysis

Standard addition curves for each test compound were constructed by adding increased amounts of drug to mouse or human $A^+$ plasma (Long Island Blood Services; Melville, N.Y.). An equal volume of 10 mM tetramethylammonium chloride/10 mM heptane sulfonate/4.2 mM $H_3PO_4$ (Buffer A) was added to the plasma sample, which was then loaded onto a washed 1 g cyanopropylsilane (or octadecylsilane for CNI-1894) solid-phase extraction column (Fisher Scientific). The column was washed with 1.0 ml of water and then eluted with 1.0 ml of 10 mM tetramethylammonium chloride/10 mM heptane sulfonate/4.2 mM $H_3PO_4$/95% $CH_3CN$/5% $H_2O$ (Buffer C). The eluted sample was reduced to dryness in a rotary evaporator and resuspended in 1.0 ml Buffer A.

Two hundred μl of the resuspended sample was injected onto a Hewlett-Packard model 1090 high performance liquid chromatography system (HPLC)(Wilmington, Del.) equipped with a photodiode array ultraviolet/visible spectrophotometric detector, autosampler, and Chemstation operating software. The column used was a 250×4.6 mm Zorbax RX-C8 column (Mac-Mod Analyticals.; Chadd's Ford, Pa.) kept at room temperature and run at 1.5 ml/min. The mobile phase used was Buffer A and 10 mM tetramethylammonium chloride/10 mM heptane sulfonate/4.2 mM $H_3PO_4$/75% $CH_3CN$/25% $H_2O$ (Buffer B), with all runs initiated at 10% Buffer B. A linear 30 min gradient to 60% Buffer B was then performed, followed by a 4 min reverse gradient to initial conditions. Compounds CNI-0294, -1194, 1594, and -1794 were detected by ultraviolet absorbance at 300 nm, CNI-1894at 240 nm, and pentamidine at 265 nm. In this assay system, the CNI test compounds have a linear response and are detectable down to at least 19.5 ng per injection.

7.2 Toxicity Studies

7.2.1 Method

The doses of compounds of the invention found to be lethal to 50% of the mice ($LD_{50}$) were determined by intraperitoneal injection of groups of five animals with increasing doses of each compound. CNI-0294 was administered from 0, 2, 10, 20, 40, 80, 160, 320, 640, 1280 mg/kg in 0.5 ml of water/HCl; CNI-1594 at 0, 2.4, 5, 10, 20, 40, 80 mg/kg in 0.5 ml of water/HCl; CNI-1794 at 0, 20, 50, 80 mg/kg in 0.5 ml of water/HCl; and CNI-1894 at 0, 10, 20, 40, 80, 240, 480, 960 mg/kg in water/HCl. All animals were observed for visible signs of acute or long-term toxicity. The percentage of animals in each group which died were utilized to calculate the $LD_{50}$ by non-linear curve fitting with the Enzfit software (Elsevier Bioscience; Cambridge, UK) programmed with the Chou equation (Chou 1976, J Theor Biol 39:253–276)).

7.2.2 Results

The compounds (FIGS. 4A–E), were screened for toxicity via a modified $LD_{50}$ assay procedure as described above in an outbred strain of mice. The results are shown in Table VII as follows:

TABLE VI

The toxicity of the CNI compounds, as measured by the median lethal dose determined as described above.

| Compound | $LD_{50}$ ± standard deviation (mg/kg) |
|---|---|
| 0294 | 587.77 ± 65.79 |
| 1194 | >160* |
| 1594 | 49.04 ± 0.08 |
| 1794 | 48.93 ± 0.12 |
| 1894 | 258.64 ± 1.37 |

*Higher doses were not tested due to limiting amounts of the compound.

CNI-0294 was found to be very well tolerated (see Table VI), with no overt signs of toxicity detectable at doses approaching the $LD_{50}$. The other compounds in the CNI series were designed to allow for structure-function relationships with respect to activity and toxicity. CNI-1194, which differs from CNI-0294 only by the lack of a methyl group on the heterocyclic nitrogen, was also well tolerated, with a high $LD_{50}$ (Table VI). However, CNI-1594, which is similar to CNI-1194 plus the omission of one of the acetyl groups on the benzene rings, was appreciably more lethal (Table VI). This toxicity was immediate, with death occurring in minutes and the animals displaying signs of acute neurotoxicity. CNI-1794, which is identical to CNI-1594 except that the single acetyl group is moved para to the heterocyclic substituent, had an $LD_{50}$ identical to that for CNI-1594 (Table VI). CNI-1894, which is similar to CNI-0294 and -1194 but lacks the heterocyclic ring, was also reasonably well tolerated. Animals dosed with large amounts of CNI-1894 died 2–3 days post injection, and showed no sign of any immediate toxicity. Based on the above observation, it is concluded that the presence of the heterocyclic ring in the compounds of the invention plays only a small role in determining toxicity, while the presence of two acetyl groups on the benzene ring is very important. Therefore, a preferred compound of the invention showing low toxicity contains two acetyl groups on the benzene ring.

7.3 Pharmacokinetic Studies

7.3.1 Methods

Female ND4 Swiss Webster mice (21–24 g) were obtained from Harlan Sprague Dawley (Indianapolis, Ind.) and randomly placed in groups of five in cages with free access to food and water. Each group of animals received 50 mg/kg of CNI-0294, -1194, or -1894, or 20 mg/kg of CNI-1594 in a volume of 0.5 ml. Compound CNI-0294 was administered intraperitoneally or by oral gavage as a solution in water or a suspension in 10% DMSO/peanut oil. The other CNI compounds were administered intraperitoneally or by oral gavage as a solution in water titrated with sufficient HCl to dissolve the drug. At various time points, ranging from 5 min to 4 days, a single group of animals was euthanized by carbon dioxide inhalation and bled by cardiac puncture using heparin as an anticoagulant. The blood from the five mice in the group was pooled and centrifuged at 14000×g for 10 min. The volume of plasma was measured, and equal volume of Buffer A added, and the mixture extracted and analyzed as described above, except that the dried eluates were resuspended in 200 μl Buffer A and 100 μl was injected onto the high performance liquid chromatography (HPLC) system.

As inspection of the blood concentration-time curves for a single i.p. injection showed a typical biphasic appearance, standard methods of pharmacokinetic measurement were employed (1982, Gibaldi et al., Pharmacokinetics. Marcel Dekker, New York). The area under the plasma concentration-time curve (AUC) was determined, and bioavailability was measured as $AUC_{oral}/AUC_{i.p.}$ A and B represent the zero time intercept of the distribution and elimination phases respectively, and a and β the respective slopes of the phases multiplied by 2.303. The $t_{1/2\alpha}$ and $t_{1/2\beta}$ are calculated half-lives of the drug in each phase (0.693/α and 0.693/β respectively). The volume of distribution (VD) was calculated as dose/B, and the total clearance rate ($Cl_{tot}$) calculated as $\beta*V_D$. $C_{max}$ and $t_{max}$ are the maximal plasma concentration and time of this measurement, respectively.

7.3.2 Results

As judged by the plasma concentration-time curves from a single intraperitoneal injection, each compound in the CNI series had similar pharmacokinetic properties despite the structural differences. The kinetic parameters are summarized in Table III and a typical pattern is shown for CNI-1194 in FIG. 5. The drugs were rapidly absorbed, with the maximal plasma concentration reached in 5–15 min, and also had a rapid distribution phase, with a $t_{1/2\alpha}$ of 0.32–0.62 hr. Differences were found to occur in the maximal plasma concentration and parameters related to the elimination phase. CNI-0294 achieved the highest maximal plasma level for a single 50 mg/kg i.p. injection, with 18.76 μg/ml, and CNI-1894 was very similar with a value of 13.43 μg/ml. As CNI-1194 had an appreciably lower maximal plasma level and a slower $t_{max}$ when compared with CNI-0294, it appears that the presence of the methyl substituent on the heterocyclic nitrogen enhances drug absorption from the peritoneum. A comparison of CNI-1194 and CNI-1594 implied that the number of acetyl groups had little effect on drug absorption. The values relating to elimination (β, B, $t_{1/2\beta}$, $V_d$, $Cl_{tot}$) were found to vary, but no clear structural relationship could be discerned. All the compounds, except CNI-1894, were undetectable in plasma after 24 hr and approached the limit of detection after 5–6 hr. Therefore, as a general property, the compounds of the invention are absorbed and eliminated rapidly. A preferred compound of the invention has a methyl substituent on the heterocyclic ring nitrogen at position 1 and possesses enhanced absorption from the peritoneum.

Experiments were also performed with CNI-0294 and -1194 to evaluate relative bioavailability. By comparing the $AUC_{oral}$ against the $AUC_{i.p.}$ for a single 50 mg/kg dose, CNI-0294 was found to have 6% relative bioavailability and CNI-1194 15%. The maximal plasma level was 0.4 μg/ml for CNI-0294 and 0.35 μg/ml for CNI-1194, and the drugs were detectable in plasma for at least 6 hr (see FIG. 5).

7.4 Metabolic Studies

During the analysis of the plasma samples for the pharmacokinetic parameters, a number of additional HPLC peaks were detected which increased and decreased over time. Extra peaks of this nature were seen in samples from each of the CNI series as shown in FIGS. 8A–8D. As it was possible that these peaks represented metabolites of the CNI compounds, the compounds of the invention were screened in a simple model of primary metabolism.

7.4.1 Method

Several female ND4 Swiss Webster mice were euthanized by carbon dioxide inhalation and the livers excised and rinsed with ice cold phosphate buffered saline (pH 7.4). The livers were minced, gently homogenized in 50 mM phosphate buffer (pH 7.4) with a Dounce homogenizer, and centrifuged at 9600×g for 20 min. The post-mitochondrial supernatant was kept, glycerol added to 20%, and frozen at −70° C. in 1.0 ml aliquots until used. For each incubation, 1.0 ml of a 1.0 mg/ml drug solution was added to 3.0 ml of 50 mM phosphate buffer (pH 7.4), 1.0 ml of 2 mg/ml NADPH in 50 mM phosphate (pH 7.4), and 1.0 ml of the post-mitochondrial supernatant. Five hundred μl of each incubate was then immediately transferred to an ice-cold tube to provide the zero-time sample, and addition 500 μl aliquots removed to ice-cold tubes at 8, 15, 30, and 60 min. The samples were then extracted, and analyzed by HPLC as described in section 7.1. Control incubations were also performed where drug or post-mitochondrial supernatant was omitted. An incubation using pentamidine was performed to confirm microsomal activity (Berger et al., 1992, Antimicrob. Ag. Chemother. 36:1825–1831). Peaks in the CNI compound incubations which increased over time, and were not present in control samples lacking the enzyme preparation were treated as putative metabolites.

7.4.2 Results

Using post-mitochondrial supernatants of homogenized mouse livers as a source of enzyme, the drugs were incubated in the presence of NADPH. As described in Berger et al. supra, pentamidine was used as a positive control, and the seven, expected, primary metabolites were detectable, confirming the activity of the enzyme preparation. Extraction and analysis of the CNI incubates showed the presence of numerous, putative metabolite peaks that were not present in negative control incubations (FIG. 6). Incubation of CNI-0294, -1594, or -1194 was found to produce three minor and one major metabolite and CNI-1894 had one minor and one major metabolite. The major metabolite was found to elute 0.9–1.2 min closer to the solvent front for CNI-0294, -1194, and -1594, suggesting that the same position was being altered in each of these compounds. The metabolic conversion in the post-mitochondrial supernatant system was considerable, with 43.5% of CNI-0294, 65.19% of CNI-1194, 11.74% of CNI-1594, and 17.28% of CNI-1894 altered during the course of a 60 min incubation (as judged by peak area). These results indicated that appreciable metabolism of the compounds of the invention should occur in vivo.

Re-examination of the plasma samples confirmed that the several of the unknown plasma peaks seen in FIGS. 6A and 6B corresponded to the putative metabolites in FIGS. 7A–7D. However, the metabolic model system did not produce all the unknown peaks seen in the plasma samples. In particular, a plasma peak eluting at 11–14 min was seen with all the compounds in vivo, but not seen at all in the in vitro test system. As was evident from the plasma time-course samples, there appeared to be a large amount of metabolic conversion in vivo of all of the compounds, regardless of the route of administration.

7.5 Conclusions

The toxicity, pharmacokinetics, and metabolism of the novel arylene bis(methylketone) compounds of the invention, and several novel analogues thereof likewise of the invention were examined in mice. With a median lethal dose of 587.77 mg/kg, CNI-0294 was well tolerated when administered intraperitoneally. Analogues which also had two acetyl groups on the phenyl moiety were also well tolerated, with median lethal doses exceeding 160 mg/kg i.p. All visible toxic reactions appeared to be rather delayed (generally 2–3 days post injection). While no biopsy samples were taken, such a delay would be consistent with organ damage by very high doses these compounds. Compounds which had only one acetyl group were found to be more toxic, with median lethal doses of 48.93–49.04 mg/kg i.p. While the visible symptoms following injection of CNI-1594 or -1794 suggested a lethal neurotoxicity, the structural differences between the two drugs indicate that antagonism of an endogenous neurotransmitter is unlikely.

In test animals, all of the compounds possessed very rapid pharmacokinetic properties, with the plasma maximal concentration, for intraperitoneal injection, being reached in 5–15 min, and 15–60 min for oral dosing. For CNI-0294, a plasma maximal concentration of 18.76–18.93 μg/ml was reached after injection of 50 mg/kg i.p. The other compounds tested achieved lower maximal plasma levels (1.9–13.43 μg/ml). The half-life of the distribution phase ($t_{1/2\alpha}$) was 0.32–0.62 hours, and that for the elimination phase ($t_{1/2\beta}$) was 3.65–23.10 hours. All of the kinetic parameters are consistent with drugs that are very rapidly cleared from the plasma and are not retained in tissues for a long period of time. Both CNI-0294 and -1194 were orally absorbed, with a relative bioavailability of 6 and 15 percent respectively. This latter feature is very favorable for continued development of these compounds as anti-infective agents, particularly as antiviral and antiparasitic agents, and more particularly as anti-retroviral and anti-protozoal agents, and yet particularly as anti-HIV agents and antimalarials. The toxicity, kinetic, and bioavailability data suggest that frequent, high, oral doses of the CNI-0294 can safely maintain therapeutically effective plasma concentration.

Metabolism of the drugs was assessed in a mouse liver post-mitochondrial supernatant system, and extensive metabolism was discovered (11.74–65.19% metabolized during, a 60 minute incubation). Examination of plasma samples showed that there was considerable in vivo metabolism, with at least 4–6 metabolites easily detected during the first 3 hours following i.p. administration of the test compounds. The levels of metabolite rapidly exceeded plasma concentrations of the parent compound. The HPLC retention times indicated that the compounds were likely altered in the same positions. In addition, the metabolites, like the parent compounds, appeared to have very rapid plasma kinetics.

8 EXAMPLE: DEMONSTRATION OF ANTI-MALARIAL ACTIVITY

8.1 The Compounds Have Anti-Malarial Activity In Vitro

8.1.1 Method

The antimalarial activity of the compounds was determined essentially as described in Desjardins et al. supra. Fifty μl of various concentrations of a compound of the invention, chloroquine, or pyrimethamine were added to the wells of microtiter plates, followed by 200 μl of ring-stage, synchronized, *P. falciparum*-infected erythrocytes (final hematocrit=1.5%, final parasitemia =1–5%). The plates were incubated for 24 hr in a candle jar kept at 37° C., and then 25 μl of $[^3H]$-hypoxanthine (Amersham, Arlington Heights, Ill.; 2.5 μl Ci/well) was added. The plates were then incubated for a further 24 hr, before harvesting onto Unifilter-96 GF/C filter-microplates (Packard; Meriden, Conn.). Twenty-five μl of Microscint scintillation fluid (Packard) was added to each well of the filter-microplate, which was subsequently counted in a Top-count microplate scintillation counter (Packard). The percent of $[^3H]$-hypoxanthine uptake relative to control infect-erythrocytes was used to determine the $IC_{50}$ value for the compounds by non-linear regression for $LD_{50}$ determination.

8.1.2 Results

Using the hypoxanthine-incorporation method for assessing *Plasmodium falciparum* growth in vitro as described above, CNI-0294 was found to have considerable anti-malarial activity (Table VII).

TABLE VII

The antimalarial activity of CNI-0294, chloroquine, and pyrimethamine in vitro against several *Plasmodium falciparum* clones. The median inhibitory concentration was determined as described above.

| Clone | Chloroquine $IC_{50}$ | Pyrimethamine $IC_{50}$ ($\mu$M) | CNI-0294 $IC_{50}$ ($\mu$M) |
|---|---|---|---|
| D10 | 26.99 ± 2.42* | 170.70 ± 24.60 | 4.00 + 0.41 |
| Dd2 | 122.54 ± 7.26 | 103.70 ± 9.79 | 3.52 + 0.10 |
| FCR-3 | 104.68 ± 9.98 | 0.04 ± 0.01 | 3.09 + 0.30 |
| HB3 | 6.73 ± 0.16 | 8.97 ± 2.75 | 1.79 + 0.27 |
| W2mef | 143.79 ± 13.30 | 17.81 ± 13.46 | 2.29 + 0.22 |

*Each value is ± standard deviation (n = 4 for chloroquine and CNI-0294, and n = 2 for pyrimethamine).

The median inhibitory concentration ($IC_{50}$) for CNI-0294 was calculated to be 1.79–4.00 $\mu$M for a series of cloned parasites which have different sensitivities to chloroquine or pyrimethamine (Table VII).

The Dd2 clone of *P. falciparum*, which was both chloroquine and pyrimethamine resistant, was utilized to compare the antimalarial activity of the remaining CNI compounds (Table VIII).

TABLE VIII

The antimalarial activities of the CNI compounds against the chloroquine- and pyrimethamine-resistant *P. falciparum* clone Dd2. The median inhibitory concentration was determined as described above.

| Compound | $IC_{50}$ ± standard deviation ($\mu$M) |
|---|---|
| 0294 | 3.67 ± 0.57* |
| 1194 | 20.27 ± 1.62 |
| 1594 | 23.73 ± 0.59 |
| 1894 | ≧200** |
| 4594 | 25.11 ± 0.72 |

*n = 4 for all. The CNI-0294 replicates were independent of those shown in Table VII.
**Highest concentration tested.

In independent measurements, CNI-0294 agreed well with the results in Table VII, and CNI-1194 was found to be approximately 5-fold less active. This difference suggested that the heterocyclic methyl group is required for maximal activity. CNI-1594 had an $IC_{50}$ equal to that for CNI-1194 or CNI-4594 demonstrating that loss of one or both of the acetyl groups can have little effect on the antimalarial activity. CNI-1894, however, was inactive at the highest concentration tested.

8.2 The Compounds Have Anti-Malarial Activity In Vivo

8.2.1 Method

The antimalarial activity of CNI-0294 in vivo was assessed by infecting female ND4 Swiss Webster mice with 100 $\mu$l of *Plasmodium berghei* NYU-2 infected mouse erythrocytes (50% parasitemia) by intraperitoneal injection. The animals were subsequently injected intraperitoneally once per day on days 1–4 of the infection with 0.5 ml water or 0.5 ml of 50 mg/kg CNI-0294 in water. Four hours after the final injection, small blood samples were taken from the tail, and thin smears stained with Dif-Quick (Baxter, Miami, Fla.). The parasitemia of control and treated animals was enumerated by inspection of at least 1000 erythrocytes in each animal.

8.2.2 Results

As the CNI-0294 $IC_{50}$ for *P. falciparum* was in the range achieved for approximately one hr following a single i.p. injection of 50 mg/kg in mice, the compound was also screened in vivo in mice infected with *Plasmodium berghei*. Utilizing the four day suppression test, where parasitemia is enumerated following four daily injections of the test compound (in this case 50 mg/kg i.p.), CNI-0294 was found to significantly (P≦0.01) lower the parasitemia by 10-fold (FIG. 9).

8.3 Conclusions

As indicated in Table VII, CNI-0294 was effective against various clones of *P. falciparum*. The consistency in CNI-0294 $IC_{50}$ over such a range of chloroquine and pyrimethamine $IC_{50}$'s suggested that CNI-0294 had a different mechanism of action than either of these established antimalarials.

While daily 50 mg/kg injections i.p., for 4 days, were found to strongly suppress *P. berghei* infection in mice, these animals were not completely cured during this course of treatment. The difference between these in vivo results and the more striking *P. falciparum* in vitro results are likely due to the kinetic and metabolic properties of the compound. In vitro, the parasites are exposed to a constant level of the drug for 48 hr, with no source of host metabolizing enzymes. In the case in vivo, the single, daily i.p. injection only provides therapeutic plasma concentrations for approximately one hour and there is considerable metabolism to compounds which may have reduced anti-plasmodial activity. In light of these observations, one of ordinary skill in the art would be able to further optimize the dosing regimens.

9 EXAMPLE: MECHANISM OF INHIBITION OF HIV-1 NUCLEAR TRANSLOCATION BY COMPOUND NO. 2

The following experiments demonstrate the inhibitory mechanism of compound No. 2 (also known as CNI-0294 or CNI-H0294) on HIV nuclear localization, which is based on the inactivation of the nuclear localization sequence (NLS) of the HIV matrix antigen (MA) in the presence of HIV reverse transcriptase (RT). The results described herein provide a basis for the development of a novel class of antiviral compound that inhibit nuclear localization and that are selective against specific NLS-containing proteins or molecular complexes comprising NLS-containing protein.

9.1 Materials and Methods

Infection with Mutant HIV-1 or HIV-Like Pseudovirions

H9 cells were infected with HIV-1 or HIV-like pseudovirions (Haffar, et al., 1990, J. Virol., 64:2653–2659) at a multiplicity adjusted according to p24 content (50 ng p24 per 106 cells). The MA $NLS^-$ virus contains substitutions of isoleucine residues for lysines in positions 26 and 27 of MA in an NLHX backbone (Westervelt., et al., 1992, J. Virol. 66:2577–2582), thus inactivating the NLS. The $Vpr^-$ virus has the initiating ATG of the vpr gene changed to GTG, thus abolishing expression of this gene. The ΔMA NLS pseudovirions have leucine substituting for lysine in position 28 of MA. This mutation abrogates nuclear translocation of HIV-1 gag RNA in growth-arrested H9 cells infected with pseudovirions. After a 1 hour absorption, excess viruses or pseudovirions were washed away, and cells were incubated for an additional 2–3 hour period at 37° C. prior to analysis.

Preparation of Cytoplasmic Lysates

Cytoplasmic extracts were prepared by lysing cells in cold extraction buffer (10 mM KCl, 10 mM Tris-HCl [pH 7.6], 0.5 MM $MgCl_{21}$ 1 $\mu$g/ml each of leupeptin and aprotinin, and 1 mM phenylmethylsulfonyl fluoride [PMSF]) by 20–30 strokes of a Dounce homogenizer under the control of phase-contrast microscopy. After removal of nuclei, cytoplasmic extract was cleared by centrifugation at 15,000 g for 10 min.

Analysis of Binding of Nucleoprotein Complexes to Karyopherin α

Cytoplasmic extracts prepared from HIV-1-or pseudovirion-infected H9 cells were adjusted to 0.14 M NaCl, 0.1% Tween 20 and precleared with glutathione-Sepharose beads for 30 min. at room temperature. Karyopherin a was expressed as a fusion protein with glutathione S-transferase (GST) which can bind glutathione beads in solution. GST-karyopherin α immobilized on Sepharose beads was then added (about 50 μg of immobilized karyopherin α per extract from 108 infected cells) and the mixture was incubated at room temperature for another 30 min. Beads were then pelleted by centrifugation and washed 3 times with PBS supplemented with 0.1 k Tween 20, 1 μg/ml each of leupeptin and aprotinin, and 1 mM PMSF. HIV-1 DNA was isolated from the beads by SDS-proteinase K treatment with subsequent phenol-chloroform extraction, while pseudovirion gag RNA was isolated by RNazol (Biotecx Laboratories Inc.).

Analysis of CNI-H0294 Interaction with HIV-1 Proteins in Solution 0.28 nanomoles of recombinant MA or RT [p66/p51 dimer were mixed with 20 nmol of [$^{14}$C]CNI-H0294 (specific activity $5\times10^4$ cpm/nmol) and incubated 2 hr at room temperature in 40 μl of binding buffer (PBS supplemented with 1% BSA, 0.1% Tween 20, 1 μg/ml leupeptin, 1 μg/ml aprotinin, 1 mM PMSF). Sheep anti-MA or rabbit anti-RT sera (both obtained from NIH AIDS Research and Reference Reagent Program) or pre-immune control sera were then added (at 1:100 dilution) and incubation continued for another 1 hr at room temperature.

Immune complexes were precipitated with protein G-agarose, washed, and then eluted with 0.1 M glycine, pH 2.8. Radioactivity of the eluate was measured in a scintillation counter.

Analysis of CNI-H0294 Interaction with HIV-1 Pre-Integration Complexes

Cytoplasmic lysates prepared from HIV-1-infected cells were treated with 10 μM of [$^{14}$C]-labeled CNI-H0294 (specific activity $5\times10^4$ cpm/nmol) in 1 ml extraction buffer adjusted to 0.14 M NaCl. Sodium borohydride was then added to a final concentration 10 mM and samples were incubated 1 hr at room temperature prior to immunoprecipitation to reduce double bonds of Schiff bases to an irreversible secondary amine. Immunoprecipitation was performed as described above, but beads were stringently washed three times with PBS supplemented with 0.1% SDS, 1% sodium deoxycholate, 1 μg/ml each of aprotinin and leupeptin, and 1 mM PMSF.

9.2 Results

CNI-H0294 reacts with adjacent lysines in the NLS, thus making it capable of neutralizing NLSs on many different proteins. Interestingly, CNI-H0294 Exhibited remarkably low cytotoxicity in monocyte and T lymphocyte cultures in vitro (50% toxic dose >1 mM) and in vivo in mice (LD50=590 mg/kg, see Table VI). These results suggest that the molecular mechanism of MA NLS inactivation by CNI-H0294 is very specific. Indeed, this compound, did not block nuclear import of nucleoplasmin-coated gold particles, nor of BSA with conjugated NLS peptides that mimic the NLS of SV40 large T antigen.

CNI-H0294 Inhibits Interaction between HIV-1 Pre-Integration Complexes and Karyopherin α, but does not Affect Binding of Karyopherin α to Pseudovirion-Derived Nucleoprotein Complexes.

The initial step in the process of nuclear import is binding of karyopherin α (also termed NLS-receptor/importin) to an NLS. Results presented in FIG. 10A demonstrate that wild-type HIV-1 pre-integration complexes bound to GST-karyopherin α immobilized on glutathione-Sepharose beads (lane 1). Mutant pre-integration complexes that lack Vpr (MA NLS$^+$Vpr$^-$, lane 3) bound with reduced efficiency, while binding of the complexes with mutated MA NLS (MA NLS_Vpr$^+$, lane 2) was even more impaired. Pre-integration complexes that lack Vpr and are mutant in MA NLS (MA NLS_Vpr$^-$) did not bind to karyopherin α (lane 4). These results are consistent with the analysis of MA and Vpr binding to karyopherin α which demonstrated that while Vpr can bind weakly to karyopherin α, its main role is to enhance the MA NLS-karyopherin α interaction.

To facilitate analysis of HIV-1 nuclear translocation and of the mechanism of drug effects on this process, a simplified model of the HIV-1 pre-integration complex was used which comprises a minimal number of non-essential proteins. This model employs gag-env pseudovirions which exhibit an HIV-like core but are composed exclusively of Gag (MA, CA, NC, p6) and Env (gp41 and gp120) proteins. These pseudovirions package HIV-1 gag RNA and translocate this RNA into the nucleus of an infected cell in a manner similar to the behavior of HIV-1 pre-integration complexes. Results presented in FIG. 10B demonstrate that karyopherin α binds nucleoprotein complexes formed in pseudovirion-infected CD4+ T cells (lane 3). Binding required a functional MA NLS as mutation of the NLS (FIG. 10A, lane 1) or pre-treatment of nucleoprotein complexes with polyclonal anti-MA antibodies (lane 2) greatly diminished binding to karyopherin α. Thus, it is concluded that pseudovirion-derived nucleoprotein complexes interact with karyopherin α in a manner similar to HIV-1 pre-integration complexes.

The effect of CNI-H0294 on the interaction between karyopherin α and HIV-1 versus pseudovirion nucleoprotein complexes was examined. It was found that CNI-H0294 inhibited in a dose-dependent manner binding of karyopherin α to HIV-1 pre-integration complexes (FIG. 10C, top panel). Quantitation on a Phosphorimager demonstrated that 0.1 μM and 1 μM of CNI-H0294 reduced karyopherin α/HIV-1 binding 8- and 25-fold, respectively. These results explain the inhibition of HIV-1 nuclear import by the compound and correlate well with the dose response curve obtained when HIV-1-infected monocyte cultures were treated with CNI-H0294. Surprisingly, CNI-H0294 did not inhibit binding of karyopherin α to pseudovirion-derived nucleoprotein complexes (FIG. 10C, bottom panel) or to purified recombinant MA. These results suggest that the mechanism of CNI-0294 inhibition requires a factor(s) present in the HIV-1 pre-integration complex but absent from pseudovirion-derived complexes.

Structure-Activity Relationships within the CNI-H Group of Compounds

To further investigate the mechanism of action of CNI-H0294, the structure-activity relationships within compounds of the invention were examined (Table IX).

Table IX Structure-Function Analysis of Anti-HIV Activity of CNI Compounds

CNI compounds were added at various concentrations (10 pM to 10 nM) to cultures of primary human monocytes together with HIV-$1_{ADA}$ and were present throughout the entire experiment. A 50% inhibitory concentration ($IC_{50}$)

was determined at day 9 after infection. Some compounds did not achieve 50% inhibition at maximal concentration yet exhibited anti-HIV activity; in these cases the results are present as >10 $\mu$M.

| Compound | Structure | $IC_{50}$ |
|---|---|---|
| CNI-H0294 | 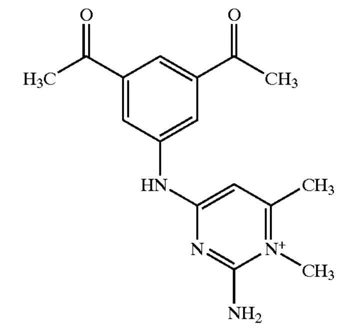 | 50 nM |
| CNI-H1894 | 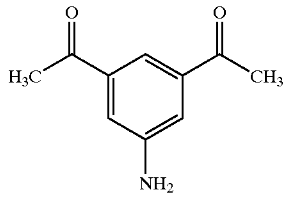 | >10 $\mu$M |
| CNI-H1494 | 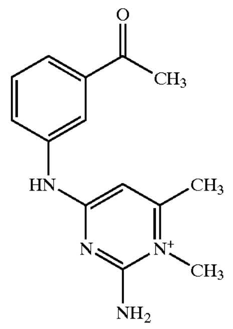 | 1 $\mu$M |
| CNI-H3094 | 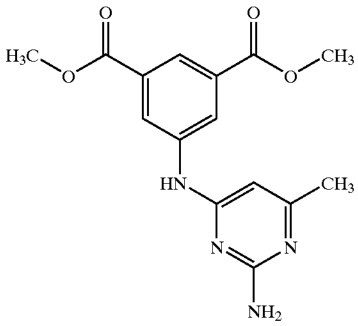 | >10 $\mu$M |

Absence of the reactive carbonyl groups (compounds CNI-H1494 and CNI-H3094) or the pyrimidine side chain (compound CNI-H1894) resulted in a dramatic decrease of the drug's potency. As the carbonyl groups were designed to react with lysine residues within MA NLS, it was not surprising that their absence decreased the drug's activity. In contrast, a role for the pyrimidine side chain was unexpected, and suggested that this side group may be involved in binding CNI-H0294 to the pre-integration complex.

CNI-H0294 Binds to RT

Binding of CNI-H0294 to RT or MA was tested in vitro using [$^{14}$C]-labeled CNI-H0294 and recombinant RT and MA proteins (FIG. 11). Specific immunoprecipitation was used to quantify the amount of bound CNI-H0294. Preliminary experiments showed that both anti-RT and anti-MA reagents specifically recognized and immunoprecipitated RT and MA, respectively. As shown in FIG. 11, about 17,000 cpm, or 0.34 nmol of CNI-H0294 (specific activity 50,000 cpm/nmol) were immunoprecipitable from incubations of drug with 0.28 nmol RT, suggesting that CNI-H0294 binds to RT in a 1:1 molar ratio. The specificity of this interaction was further confirmed by immunoprecipitation experiments using cold CNI-H0294 to compete out precipitable counts associated with labeled drug (FIG. 11). No binding was observed with recombinant MA, and no radioactivity was precipitated by immune sera if the recombinant protein was omitted from the reaction mixture. In similar experiments, the binding of CNI-H0294 to Vpr nor to integrase, two other proteins known to be present within the HIV-1 pre-integration complex, were detected. These experiments established that CNI-H0294 bound directly to RT, but not to other proteins of the HIV-1 pre-integration complex. Of interest, CNI-H0294 did not significantly inhibit reverse transcription of HIV-1 in infected cells, nor did it block in concentrations up to 50 $\mu$M the enzymatic activity of HIV-1 RT in vitro, suggesting that an effect on RT activity cannot account for the anti-viral action of the compound.

Binding to RT is Critical for the Anti-HIV Activity of CHI-H0294

The role of CNI-H0294/RT interaction in the drug's activity was analyzed in experiments with compound CNI-H3094. As CNI-H3094 does not have reactive carbonyl group but contains the active pyrimidine side chain (see Table IX), it could effectively compete with CHI-H0294 for binding to the same site on the HIV-1 pre-integration complex, albeit it did not inhibit nuclear import of HIV-1. FIG. 12A shows that unlabeled CNI-H3094 inhibits binding of [$^{14}$C]-labeled CNI-H0294 to RT in a dose-dependent manner. Likewise, CNI-H3094 restored binding of HIV-1 pre-integration complexes to karyopherin $\alpha$ in the presence CNI-H0294 (FIG. 12B). A 5-fold excess of CNI-H3094 (FIG. 12B, lane 4) reduced significantly the inhibitory effects of CNI-H0294 on binding of HIV-1 pre-integration complexes to karyopherin $\alpha$, and a 10-fold excess (lane 5) completely eliminated the inhibitory effect. In a control experiment, CNI-H3094 did not inhibit binding of HIV-1 pre-integration complexes to karyopherin $\alpha$ (FIG. 12B, lane 1); this correlates with the compound's lack of anti-HIV activity (Table IX). Finally, CNI-H3094 eliminated the inhibitory effect of CNI-H0294 on HIV-1 replication in monocyte cultures (FIG. 12C). These results confirm the critical role of CNI-H0294/RT interaction in the drug's mechanism of action and also show a direct correlation between the drug's binding to RT, inhibition of HIV-1/karyopherin $\alpha$ interaction, and repression of viral replication.

CNI-H0294 Inactivates the NLS of MA without Disrupting MA Association with the HIV-1 Genome The results presented herein indicate a direct role for RT in the anti-HIV effect of CNI-H0294 and provide a molecular explanation for the high specificity of the compound. However, these results do not explain how CNI-H0294 prevents binding of HIV-1 pre-integration complexes to karyopherin $\alpha$, as RT does not bind to directly to karyopherin $\alpha$. One possibility was that binding of CNI-H0294 to RT disrupts the pre-integration complex and causes dissociation of MA from HIV-1 cDNA.

To test this hypothesis, cytoplasmic lysates of HIV-1-infected H9 cells were treated with CNI-H0294 and mixed with immobilized karyopherin α or subjected to immunoprecipitation with antibodies that bind MA. Although CNI-H0294 blocked the interaction of the pre-integration complexes with karyopherin α (FIG. 13A, lane 2), it did not prevent immunoprecipitation of viral DNA with anti-MA serum (FIG. 13A, lane 3); thus MA was still associated with HIV-1 cDNA but lost its ability to bind karyopherin α. As binding of pre-integration complexes to karyopherin α is controlled mainly by the MA NLS (FIGS. 10A and 10B), these results indicate that CNI-H0294 neutralizes the NLS activity of MA, either directly (through chemical modification) or indirectly (e.g. by steric hindrance).

To discriminate between these two possibilities, cytoplasmic extracts of HIV-1-infected cells were treated with [$^{14}$C]-CNI-H0294 and then with sodium borohydride, to reduce the reversible Schiff bases hypothesized to form between the compound and the lysines of MA NLS and convert the attached drug molecules to irreversible adducts. MA was then immunoprecipitated with specific serum in a buffer containing of 0.1% SDS and 1% sodium deoxycholate which disrupts weak protein-drug and protein-protein interactions in the pre-integration complex without disrupting covalent bonds. Under these conditions, a significant amount of radioactivity was immunoprecipitated by anti-MA serum (FIG. 13B), in contrast to results obtained with recombinant MA (FIG. 11). These results corroborated requirement for RT for the drug's effect and suggested that the CNI-H0294 had been covalently linked to MA by borohydride treatment. Without borohydride treatment, no radioactivity was immunoprecipitated with MA. In control experiments, no radioactivity was precipitated by anti-IN serum, or by anti-MA serum from the cytoplasmic extract of cells infected with pseudovirions (FIG. 13B) which lack RT and thus do not bind CNI-H0294 (FIG. 11).

CNI-H0294 Inhibits MA NLS$^-$, but not Vpr-Mediated Binding of HIV-1 Pre-Integration Complexes to Karyopherin α

Because of the role for MA NLS and Vpr in HIV-1 nuclear import, the effects of CNI-H0294 on the interaction between karyopherin α and pre-integration complexes derived from viruses that carry mutations in Vpr (Vpr$^-$), MA NLS (MA NLS$^-$), or both were investigated (FIG. 11). These viruses (except for MA NLS$^-$Vpr$^-$ double mutant which was slightly attenuated) entered target cells and reverse transcribed their genome with similar efficiencies (FIG. 14A). The presence of CNI-H0294 diminished binding of karyopherin α to wild-type (wt) (FIG. 14B, lanes 1, 2) and Vpr$^-$ complexes (lanes 3, 4) by 95% but had no effect on binding to MA NLS$^-$ complexes (lanes 5 and 6) which is only 1–5% of that observed with MA NLS+ complexes. The inability of CNI-H0294 to block binding of MA NLS$^-$ complexes to karyopherin α can be explained by the lack of a consensus NLS in Vpr and that Vpr binds to karyopherin α in an NLS-independent manner.

Results presented hereinabove reveal the molecular mechanism of action of CNI-H0294 that specifically target nuclear import of HIV-1. The mechanism by which CNI-H0294 can inactivate the MA NLS and thus prevent nuclear import of HIV-1 is depicted in FIG. 15. According to the invention, the compound first binds to HIV-1 pre-integration complexes via RT and then forms reversible Schiff bases with contiguous lysines in an adjacent MA NLS. This interaction prevents binding of karyopherin α to the MA NLS and significantly inhibits nuclear translocation of the HIV-1 pre-integration complex. The results with pseudovirion-derived nucleoprotein complexes indicate that formation of the functional complex capable of binding karyopherin α and translocating into the nucleus resides entirely within the HIV-1 Gag proteins. Although other proteins present in the HIV-1 pre-integration complex (e.g. Vpr, IN, RT) may enhance nuclear translocation, they are not necessary for this process. The results indicate that RT and MA NLS are positioned in close proximity within the HIV-1 pre-integration complex as CNI-H0294 is very small yet seems to bind RT and the MA NLS simultaneously. As MA is made from the Gag precursor and RT is made from the Gag-Pol precursor, the ratio of RT to MA in the virion is expected to be 1:50 because the translational frameshift that leads to synthesis of the Gag-Pol precursor (rather than the Gag precursor) occurs about 2% of the time. Interestingly, about 1–2% of the virion MA protein is phosphorylated and only these molecules are incorporated into the HIV-1 pre-integration complex. This leads to an important conclusion that there is roughly an equivalent number of RT and MA molecules per HIV-1 pre-integration complex. Given the efficient inactivation of MA NLS by CNI-H0294, most if not all RT and MA molecules are in close proximity in the pre-integration complex.

The present invention is not to be limited in scope by the specific embodiments described which were intended as single illustrations of individual aspects of the invention, and functionally equivalent methods and components were within the scope of the invention. Indeed, various modifications of the invention, in addition to those shown and described herein will become apparent to those skilled in the art from the foregoing description and accompanying drawings. Such modifications are intended to fall within the scope of the appended claims.

We claim:

1. A compound having the formula:

(I)

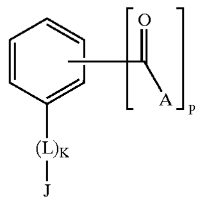

wherein A, independently, =$CH_3$, $CH_2CH_3$, COH, $COCH_3$, $COCH_2CH_3$, $CH_2COCH_3$, $CH_2COCH_2CH_3$, $C(CH_3)_2COCH_3$, or $C(CH_3)_2COCH_2CH_3$; P=1 or 2; L is a linker group containing an O atom; K=1; and wherein J represents (i) a saturated or unsaturated, substituted or unsubstituted, straight or branched acyclic hydrocarbon group; (ii) a saturated or unsaturated, substituted or unsubstituted, straight or branched acyclic group that contains one or more hetero atoms selected from the group consisting of nitrogen, sulfur and oxygen; (iii) a substituted or unsubstituted, saturated or aromatic, mono- or poly-cyclic group having 3 to 20 carbon atoms; or (iv) a substituted or unsubstituted, saturated or aromatic, mono- or poly-heterocyclic group having 3 to 20 atoms, at least one of which is nitrogen, sulfur or oxygen.

2. The compound of claim 1, that is capable of: (a) interacting with a molecule in a complex having a specific docking site which is positioned proximately to a nuclear localization signal of a protein in the complex; and (b) forming stable reversible covalent interactions with basic amino acid residues of the nuclear localization signal of the protein, wherein the protein is derived from a virus.

3. The compound of claim 1, that is capable of: (a) interacting with a molecule in a complex having a specific docking site which is positioned proximately to a nuclear localization signal of a protein in the complex; and (b) forming stable reversible covalent interactions with basic amino acid residues of the nuclear localization signal of the protein, wherein the protein is derived from a human immunodeficiency virus, influenza virus, hepatitis virus, herpes simplex virus, papillomavirus, parvovirus or measles virus.

4. The compound of claim 1, wherein K=1, L is a linker group containing an O atom, and J is (iv) a substituted or unsubstituted, saturated or aromatic, mono- or poly-heterocyclic group having 3 to 20 atoms, at least one of which is nitrogen, sulfur or oxygen.

5. The compound of claim 1, wherein K=1 and L is —O—.

6. The compound of claim 1 wherein K=1, L is a linker group containing an O atom, and J is a substituted or unsubstituted five or six membered ring having 1–4 hetero ring atoms, at least one of which is nitrogen and the remainder of which are selected from the group consisting of nitrogen, oxygen, sulfur, and a combination thereof.

7. The compound of claim 1, wherein K=1, L is a linker group containing an O atom, and J is selected from the group consisting of pyrimidine, pyridine, pyrrole, imidazole, thiazole, isothiazole, isoxazole, furazan, pyrrolidine, piperidine, imidazolidine, piperazine, oxazole, tetrazole, pyrazole, triazole, oxadiazole, and thiodiazole, and may be unsubsituted or substituted with one or more substituents selected from the group consisting of alkyl, alkoxy, phenoxy, alkenyl, alkynyl, phenylalkyl, hydroxyalkyl, haloalkyl, aryl, arylalkyl, alkyloxy, alkylthio, alkenylthio, phenylalkylthio, hydroxyalkylthio, alkylthiocarbamylthio, phenyl, cyclohexyl, pyridyl, piperidinyl, alkylamino, amino, nitro, mercapto, cyano, hydroxyl, halogen, and a combination thereof.

8. The compound of claim 1, wherein K=1, L is —O—, and J is a substituted or unsubstituted pyrimidine group.

9. The compound of claim 1, wherein P=1.

10. The compound of claim 1, wherein P=2.

11. A method of preventing productive infection by a virus of a proliferating population of cells by preventing importation of a complex containing viral nucleic acid or viral protein into the nucleus of a cell in the population, which comprises the administration of an effective amount of a pharmaceutical composition containing a compound according to the formula:

(I)

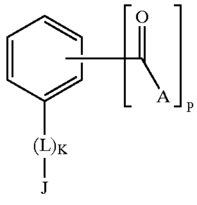

wherein A, independently, $=CH_3$, $CH_2CH_3$, COH, $COCH_3$, $COCH_2CH_3$, $CH_2COCH_3$, $CH_2COCH_2CH_3$, $C(CH_3)_2COCH_3$, or $C(CH_3)_2COCH_2CH_3$; P=1 or 2; L is a linker group containing an O atom; K=1; and wherein J represents (i) a saturated or unsaturated, substituted or unsubstituted, straight or branched acyclic hydrocarbon group; (ii) a saturated or unsaturated, substituted or unsubstituted, straight or branched acyclic group that contains one or more hetero atoms selected from the group consisting of nitrogen, sulfur and oxygen; (iii) a substituted or unsubstituted, saturated or aromatic, mono- or poly-cyclic group having 3 to 20 carbon atoms; or (iv) a substituted or unsubstituted, saturated or aromatic, mono- or poly-heterocyclic group having 3 to 20 atoms, at least one of which is nitrogen, sulfur or oxygen.

12. The method of claim 11, wherein K=1, L is a linker group containing an O atom, and J is (iv) a substituted or unsubstituted, saturated or aromatic, mono- or poly-heterocyclic group having 3 to 20 atoms, at least one of which is nitrogen, sulfur or oxygen.

13. The method of claim 11, wherein K=1 and L is —O—.

14. The method of claim 11, wherein K=1, L is a linker group containing an O atom, and J is a substituted or unsubstituted five or six membered ring having 1–4 hetero ring atoms, at least one of which is nitrogen and the remainder of which are selected from the group consisting of nitrogen, oxygen, sulfur, and a combination thereof.

15. The method of claim 11, wherein K=1, L is a linker group containing an O atom, and J is selected from the group consisting of pyrimidine, pyridine, pyrrole, imidazole, thiazole, isothiazole, isoxazole, furazan, pyrrolidine, piperidine, imidazolidine, piperazine, oxazole, tetrazole, pyrazole, triazole, oxadiazole, and thiodiazole, and may be unsubsituted or substituted with one or more substituents selected from the group consisting of alkyl, alkoxy, phenoxy, alkenyl, alkynyl, phenylalkyl, hydroxyalkyl, haloalkyl, aryl, arylalkyl, alkyloxy, alkylthio, alkenylthio, phenylalkylthio, hydroxyalkylthio, alkylthiocarbamylthio, phenyl, cyclohexyl, pyridyl, piperidinyl, alkylamino, amino, nitro, mercapto, cyano, hydroxyl, halogen, and a combination thereof.

16. The method of claim 11, wherein K=1, L is —O—, and J is a substituted or unsubstituted pyrimidine group.

17. A method for identifying compounds that are capable of targeted inactivation of the nuclear localization signal of a protein comprising:

(a) contacting an immobilized cellular receptor moiety with a protein comprising a nuclear localization signal, and a compound having the formula:

(I)

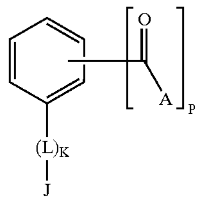

wherein A, independently, $=CH_3$, $CH_2CH_3$, COH, $COCH_3$, $COCH_2CH_3$, $CH_2COCH_3$, $CH_2COCH_2CH_3$, $C(CH_3)_2COCH_3$, or $C(CH_3)_2COCH_2CH_3$; P=1 or 2; L is a linker group containing an O atom; K=1; and wherein J represents (i) a saturated or unsaturated, substituted or unsubstituted, straight or branched acyclic hydrocarbon group; (ii) a saturated or unsaturated, substituted or unsubstituted, straight or branched acyclic group that contains one or more hetero atoms selected from the group consisting of nitrogen, sulfur and oxygen; (iii) a substituted or unsubstituted, saturated or aromatic, mono- or poly-cyclic group having 3 to 20 carbon atoms; or (iv) a substituted or unsubstituted, saturated or aromatic, mono- or poly-heterocyclic group having 3 to 20 atoms, at least one of which is a nitrogen, sulfur or oxygen;

(b) measuring the binding of the protein to the immobilized cellular receptor moiety; and (c) comparing the quantity of the protein bound to the quantity of protein bound in the absence of the compound, where a reduction in the quantity of the bound protein in the presence of the compound is indicative of targeted inactivation of the nuclear localization signal by the compound.

18. The method of claim 17, wherein the protein is in a complex.

19. The method of claim 17, wherein the protein is derived from a human immunodeficiency virus, influenza virus, hepatitis virus, herpes simplex virus, papillomarvirus, parvovirus or measles virus.

20. The method of claim 17, wherein the cellular receptor moiety is karyopherin α.

21. A method for identifying compounds that are capable of targeted inactivation of the nuclear localization signal of a viral nucleoprotein complex comprising:

(a) contacting an immobilized karyopherin α with a viral nucleoprotein complex contained in a cytoplasmic extract, said complex comprising viral nucleic acid and said cytoplasmic extract prepared from cells infected by the virus, and a compound having the formula:

(I)

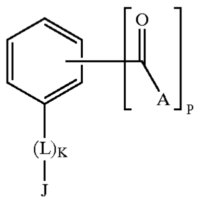

wherein A, independently, $=CH_3$, $CH_2CH_3$, COH, $COCH_3$, $COCH_2CH_3$, $CH_2COCH_3$, $CH_2COCH_2CH_3$, $C(CH_3)_2COCH_3$, or $C(CH_3)_2COCH_2CH_3$; P=1 or 2; L is a linker group containing an O atom; K=1; and wherein J represents (i) a saturated or unsaturated, substituted or unsubstituted, straight or branched acyclic hydrocarbon group; (ii) a saturated or unsaturated, substituted or unsubstituted, straight or branched acyclic group that contains one or more hetero atoms selected from the group consisting of nitrogen, sulfur and oxygen; (iii) a substituted or unsubstituted, saturated or aromatic, mono- or poly-cyclic group having 3 to 20 carbon atoms; or (iv) a substituted or unsubstituted, saturated or aromatic, mono- or polyheterocyclic group having 3 to 20 atoms, at least one of which is a nitrogen, sulfur or oxygen;

(b) measuring the binding of said complex to the immobilized karyopherin α by quantitating the amount of viral nucleic acids associated with said complex; and (c) comparing the quantity of the nucleic acid bound to the quantity of nucleic acid bound in the absence of the compound;

wherein a reduction in the quantity of the bound nucleic acid in the presence of the compound is indicative of targeted inactivation of the nuclear localization signal by the compound.

22. The method of claim 17, wherein K=1, L is a linker group containing an O atom, and J is (iv) a substituted or unsubstituted, saturated or aromatic, mono- or polyheterocyclic group having 3 to 20 atoms, at least one of which is nitrogen, sulfur or oxygen.

23. The method of claim 17, wherein K=1 and L is —O—.

24. The method of claim 17, wherein K=1, L is a linker group containing an O atom, and J is a substituted or unsubstituted five or six membered ring having 1–4 hetero ring atoms, at least one of which is nitrogen and the remainder of which are selected from the group consisting of nitrogen, oxygen, sulfur, and a combination thereof.

25. The method of claim 17, wherein K=1, L is a linker group containing an O atom, and J is selected from the group consisting of pyrimidine, pyridine, pyrrole, imidazole, thiazole, isothiazole, isoxazole, furazan, pyrrolidine, piperidine, imidazolidine, piperazine, oxazole, tetrazole, pyrazole, triazole, oxadiazole, and thiodiazole, and may be unsubsituted or substituted with one or more substituents selected from the group consisting of alkyl, alkoxy, phenoxy, alkenyl, alkynyl, phenylalkyl, hydroxyalkyl, haloalkyl, aryl, arylalkyl, alkyloxy, alkylthio, alkenylthio, phenylalkylthio, hydroxyalkylthio, alkylthiocarbamylthio, phenyl, cyclohexyl, pyridyl, piperidinyl, alkylamino, amino, nitro, mercapto, cyano, hydroxyl, halogen, and a combination thereof.

26. The method of claim 17, wherein K=1, L is —O—, and J is a substituted or unsubstituted pyrimidine group.

27. The method of claim 21, wherein K=1, L is a linker group containing an O atom, and J is (iv) a substituted or unsubstituted, saturated or aromatic, mono- or polyheterocyclic group having 3 to 20 atoms, at least one of which is nitrogen, sulfur or oxygen.

28. The method of claim 21, wherein K=1 and L is —O—.

29. The method of claim 21, wherein K=1, L is a linker group containing an O atom, and J is a substituted or unsubstituted five or six membered ring having 1–4 hetero ring atoms, at least one of which is nitrogen and the remainder of which are selected from the group consisting of nitrogen, oxygen, sulfur, and a combination thereof.

30. The method of claim 21, wherein K=1, L is a linker group containing an O atom, and J is selected from the group consisting of pyrimidine, pyridine, pyrrole, imidazole, thiazole, isothiazole, isoxazole, furazan, pyrrolidine, piperidine, imidazolidine, piperazine, oxazole, tetrazole, pyrazole, triazole, oxadiazole, and thiodiazole, and may be unsubsituted or substituted with one or more substituents selected from the group consisting of alkyl, alkoxy, phenoxy, alkenyl, alkynyl, phenylalkyl, hydroxyalkyl, haloalkyl, aryl, arylalkyl, alkyloxy, alkylthio, alkenylthio, phenylalkylthio, hydroxyalkyithia, alkylthiocarbamylthio, phenyl, cyclohexyl, pyridyl, piperidinyl, alkylamino, amino, nitro, mercapto, cyano, hydroxyl, halogen, and a combination thereof.

31. The method of claim 21, wherein K=1, L is —O—, and J is a substituted or unsubstituted pyrimidine group.

* * * * *